(12) United States Patent
Xu et al.

(10) Patent No.: US 10,526,576 B2
(45) Date of Patent: *Jan. 7, 2020

(54) COMPOSITIONS AND METHODS FOR DIFFERENTIATING STEM CELLS INTO CELL POPULATIONS COMPRISING BETA-LIKE CELLS

(71) Applicant: REGENERATIVE MEDICAL SOLUTIONS, INC., Park Ridge, IL (US)

(72) Inventors: Xiaofang Xu, Park Ridge, IL (US); Jon Odorico, Park Ridge, IL (US); Erik Forsberg, Park Ridge, IL (US); Amber A. Mael, Madison, WI (US)

(73) Assignee: REGENERATIVE MEDICAL SOLUTIONS, INC., Park Ridge, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/199,681

(22) Filed: Nov. 26, 2018

(65) Prior Publication Data

US 2019/0093083 A1 Mar. 28, 2019

Related U.S. Application Data

(63) Continuation of application No. 15/705,896, filed on Sep. 15, 2017, now Pat. No. 10,138,466, which is a continuation of application No. 15/187,345, filed on Jun. 20, 2016, now Pat. No. 9,765,302, which is a continuation of application No. 14/858,465, filed on Sep. 18, 2015, now Pat. No. 9,371,516.

(60) Provisional application No. 62/173,759, filed on Jun. 10, 2015, provisional application No. 62/052,894, filed on Sep. 19, 2014.

(51) Int. Cl.

| | |
|---|---|
| *C12N 5/071* | (2010.01) |
| *A61K 35/39* | (2015.01) |
| *A61K 9/16* | (2006.01) |
| *A61K 45/06* | (2006.01) |
| *A61K 9/50* | (2006.01) |
| *G01N 33/50* | (2006.01) |
| *A61K 35/545* | (2015.01) |

(52) U.S. Cl.
CPC .......... *C12N 5/0676* (2013.01); *A61K 9/1652* (2013.01); *A61K 9/5036* (2013.01); *A61K 35/39* (2013.01); *A61K 45/06* (2013.01); *G01N 33/507* (2013.01); *H05K 999/99* (2013.01); *A61K 35/545* (2013.01); *C12N 2500/05* (2013.01); *C12N 2500/22* (2013.01); *C12N 2500/25* (2013.01); *C12N 2500/38* (2013.01); *C12N 2500/44* (2013.01); *C12N 2500/90* (2013.01); *C12N 2501/01* (2013.01); *C12N 2501/105* (2013.01); *C12N 2501/11* (2013.01); *C12N 2501/115* (2013.01); *C12N 2501/117* (2013.01); *C12N 2501/155* (2013.01); *C12N 2501/16* (2013.01); *C12N 2501/33* (2013.01); *C12N 2501/335* (2013.01); *C12N 2501/385* (2013.01); *C12N 2501/395* (2013.01); *C12N 2501/40* (2013.01); *C12N 2501/727* (2013.01); *C12N 2501/91* (2013.01); *C12N 2501/998* (2013.01); *C12N 2501/999* (2013.01); *C12N 2506/02* (2013.01); *C12N 2506/45* (2013.01)

(58) Field of Classification Search
CPC .............. C12N 5/0676; C12N 2500/05; C12N 2500/22; C12N 2500/25; C12N 2500/38; C12N 2500/44; C12N 2500/90; C12N 2501/01; C12N 2501/105; C12N 2501/11; C12N 2501/115; C12N 2501/117; C12N 2501/155; C12N 2501/16; C12N 2501/33; C12N 2501/335; C12N 2501/385; C12N 2501/395; C12N 2501/40; C12N 2501/727; C12N 2501/91; C12N 2501/998; C12N 2501/999; C12N 2506/02; C12N 2506/45; A61K 9/1652; A61K 9/5036; A61K 35/39; A61K 45/06; A61K 35/545; G01N 33/507; H05K 999/99

See application file for complete search history.

(56) References Cited

U.S. PATENT DOCUMENTS

| | | |
|---|---|---|
| 4,557,264 A | 12/1985 | Hinsch et al. |
| 5,567,612 A | 10/1996 | Vacanti et al. |
| 5,759,830 A | 6/1998 | Vacanti et al. |
| 5,770,417 A | 6/1998 | Vacanti et al. |
| 5,843,780 A | 12/1998 | Thomson et al. |
| 5,914,262 A | 6/1999 | MacMichael et al. |

(Continued)

FOREIGN PATENT DOCUMENTS

| | | |
|---|---|---|
| WO | WO 00/52145 | 9/2000 |
| WO | WO 01/00650 | 1/2001 |

(Continued)

OTHER PUBLICATIONS

Aber et al., "Activin receptor signaling." Growth Factors. Jun. 2004;22(2):105-10.

(Continued)

*Primary Examiner* — Thaian N Ton
(74) *Attorney, Agent, or Firm* — Casimir Jones, S.C.; David Casimir

(57) ABSTRACT

Methods, kits, compositions, and systems are provided for culturing pluripotent stem cells to produce populations of cells comprising beta-like cells (e.g., pancreatic lineage, glucose-responsive, and/or insulin-producing). In particular, culture conditions are provided that result in the generation of beta-like cells from a starting culture of human pluripotent stem cells.

20 Claims, 42 Drawing Sheets

(56) References Cited

U.S. PATENT DOCUMENTS

| | | | |
|---|---|---|---|
| 6,022,743 | A | 2/2000 | Naughton et al. |
| 6,306,424 | B1 | 10/2001 | Vyakarnam et al. |
| 6,333,029 | B1 | 12/2001 | Vyakarnam et al. |
| 6,365,149 | B2 | 4/2002 | Vyakarnam et al. |
| 6,534,084 | B1 | 3/2003 | Vyakarnam et al. |
| 6,599,323 | B2 | 7/2003 | Melican et al. |
| 6,626,950 | B2 | 9/2003 | Brown et al. |
| 6,656,488 | B2 | 12/2003 | Yi et al. |
| 8,785,185 | B2 | 7/2014 | Xu et al. |
| 9,371,516 | B2 | 6/2016 | Xu et al. |
| 9,765,302 | B2 | 9/2017 | Xu et al. |
| 10,138,466 | B2 | 11/2018 | Xu et al. |
| 2004/0062753 | A1 | 4/2004 | Rezania et al. |
| 2010/0068793 | A1 | 3/2010 | Ungrin et al. |
| 2011/0086375 | A1 | 4/2011 | Ungrin et al. |
| 2012/0149051 | A1 | 6/2012 | Kugelmeier et al. |
| 2012/0315697 | A1 | 12/2012 | Pettit et al. |
| 2013/0209421 | A1 | 8/2013 | Efrat et al. |
| 2014/0186953 | A1 | 7/2014 | Rezania et al. |

FOREIGN PATENT DOCUMENTS

| | | |
|---|---|---|
| WO | WO 2012/170853 A1 | 12/2012 |
| WO | WO 2014044646 A1 | 3/2014 |
| WO | WO2016044721 A1 | 3/2016 |

OTHER PUBLICATIONS

Assady et al., "Insulin production by human embryonic stem cells." Diabetes 50, 2001, 1691-1697.

Brolen et al., "Signals from the embryonic mouse pancreas induce differentiation of human embryonic stem cells into insulin-producing β-cell-like cells." Diabetes 54, 2005, 2867-2874.

Chan et al., "Live cell imaging distinguishes bona fide human iPS cells from partially reprogrammed cells." Nat Biotechnol. Nov. 2009;27(11):1033-7.

Chang et al., "Procedures for microencapsulation of enzymes, cells and genetically engineered microorganisms" Mol Biotechnol. 2001, 17: 249-60.

Cheng et al., "Self-renewing endodermal progenitor lines generated from human pluripotent stem cells." Cell Stem Cell. Apr. 6, 2012;10(4):371-84.

Chia et al., "Multi-layered microcapsules for cell encapsulation." Biomaterials. Feb. 2002;23(3):849-56.

Cho et al., "Inhibition of activin/nodal signalling is necessary for pancreatic differentiation of human pluripotent stem cells" Diabetologia, 2012;55(12):3284-3295.

D'Amour et al., "Efficient differentiation of human embryonic stem cells to definitive endoderm." Nat Biotechnol. Dec. 2005;23(12):1534-41.

D'Amour et al., "Production of pancreatic hormone-expressing endocrine cells from human embryonic stem cells." Nat Biotechnol. Nov. 2006;24(11):1392-401.

Dorrell et al., "Isolation of major pancreatic cell types and long-term culture-initiating cells using novel human surface markers." Stem Cell Res. Sep. 2008;1(3):183-94.

Duncanson et al., "Dual factor delivery of CXCL12 and Exendin-4 for improved survival and function of encapsulated beta cells under hypoxic conditions." Biotechnol Bioeng. Aug. 2013;110(8):2292-300.

Dunussi-Joannopoulos et al., "Efficacious immunomodulatory activity of the chemokine stromal cell-derived factor 1 (SDF-1): local secretion of SDF-1 at the tumor site serves as T-cell chemoattractant and mediates T-cell-dependent antitumor responses." Blood. Sep. 1, 2002;100(5):1551-8.

Friedman et al., "A critical role for human CD4+ T-cells in rejection of porcine islet cell xenografts." Diabetes. Dec. 1999;48(12):2340-8.

Guo et al.,"Immunotherapy with nondepleting anti-CD4 monoclonal antibodies but not CD28 antagonists protects islet graft in spontaneously diabetic nod mice from autoimmune destruction and allogeneic and xenogeneic graft rejection." Transplantation. Jun. 15, 2001;71(11):1656-65.

Haase et al., "Growth arrest specific protein (GAS) 6: a role in the regulation of proliferation and functional capacity of the perinatal rat beta cell." Diabetologia. Apr. 2013;56(4):763-73.

Hrvatin et al., "Differentiated human stem cells resemble fetal, not adult, β cells." Proc Natl Acad Sci U S A. Feb. 25, 2014;111(8):3038-43.

Hosoya et al., "Preparation of pancreatic β-cells from human iPS cells with small molecules." Islets. May-Jun. 2012;4(3):249-52.

Jiang et al., "In vitro derivation of functional insulin-producing cells from human embryonic stem cells." Cell Res. Apr. 2007;17(4):333-44.

Jonsson et al., "Insulin-promoter-factor 1 is required for pancreas development in mice"Nature 371, 606-609.

Kroon et al., "Pancreatic endoderm derived from human embryonic stem cells generates glucose-responsive insulin-secreting cells in vivo." Nat Biotechnol. Apr. 2008;26(4):443-52.

Kunisada et al., "Small molecules induce efficient differentiation into insulin-producing cells from human induced pluripotent stem cells." Stem Cell Res. Mar. 2012;8(2):274-84.

Kurohara et al., "Low-dose warfarin functions as an immunomodulator to prevent cyclophosphamide-induced NOD diabetes." Kobe J Med Sci. May 23, 2008;54(1):E1-13.

Leech et al., "Expression of cAMP-regulated guanine nucleotide exchange factors in pancreatic beta-cells." Biochem Biophys Res Commun. Nov. 11, 2000;278(1):44-7.

Liu et al., "Stromal cell-derived factor-1 promotes survival of pancreatic beta cells by the stabilisation of beta-catenin and activation of transcription factor 7-like 2 (TCF7L2)."Diabetologia. Aug. 2009;52(8):1589-98.

Lu et al., "A novel cell encapsulation method using photosensitive poly(allylamine alpha-cyanocinnamylideneacetate)." J Microencapsul. Mar.-Apr. 2000;17(2):245-51.

Lu et al., "Cell encapsulation with alginate and alpha-phenoxycinnamylidene-acetylated poly(allylamine)." Biotechnol Bioeng. Dec. 5, 2000;70(5):479-83.

Nomura et al., "Enhancement of anti-tumor immunity by tumor cells transfected with the secondary lymphoid tissue chemokine EBI-1-ligand chemokine and stromal cell-derived factor-1αchemokine genes" Int J Cancer. Mar. 1, 2001;91(5):597-606.

Papeta et al., "Long-term survival of transplanted allogeneic cells engineered to express a T cell chemorepellent." Transplantation. Jan. 27, 2007;83(2):174-83.

Rajagopal et al., "Insulin staining of ES cell progeny from insulin uptake." Science. Jan. 17, 2003;299(5605):363.

Ravassard et al., "A genetically engineered human pancreatic β cell line exhibiting glucose-inducible insulin secretion." J Clin Invest. Sep. 2011;121(9):3589-97.

Rezania et al., "Maturation of human embryonic stem cell-derived pancreatic progenitors into functional islets capable of treating pre-existing diabetes in mice." Diabetes. Aug. 2012;61(8):2016-29.

Sambanis et al., "Encapsulated islets in diabetes treatment." Diabetes Technol Ther. 2003;5(4):665-8.

Schuldiner et al., "Effects of eight growth factors on the differentiation of cells derived from human embryonic stem cells" Proc Natl Acad Sci U S A. Oct. 10, 2000;97(21):11307-12.

Segev et al., "Differentiation of human embryonic stem cells into insulin-producing clusters." Stem Cells. 2004;22(3):265-74.

Sipione et al., "Insulin expressing cells from differentiated embryonic stem cells are not beta cells" Diabetologia. Mar. 2004;47(3):499-508.

Tanaka et al., "Prevention of glucose toxicity in HIT-T15 cells and Zucker diabetic fatty rats by antioxidants." Proc Natl Acad Sci U S A. Sep. 14, 1999;96(19):10857-62.

Uludag et al., "Technology of mammalian cell encapsulation." Adv Drug Deliv Rev. Aug. 20, 2000;42(1-2):29-64.

Vianello et al., "A CXCR4-dependent chemorepellent signal contributes to the emigration of mature single-positive CD4 cells from the fetal thymus." J Immunol. Oct. 15, 2005;175(8):5115-25.

(56) References Cited

OTHER PUBLICATIONS

Xu et al., "Activin, BMP and FGF pathways cooperate to promote endoderm and pancreatic lineage cell differentiation from human embryonic stem cells." Mech Dev. Sep.-Dec. 2011;128(7-10):412-27.

Yu et al., "Induced pluripotent stem cell lines derived from human somatic cells" Science. Dec. 21, 2007;318(5858):1917-20.

International Search Report dated Feb. 1, 2016, of Co-Pending International patent application No. PCT/US2015/050933. 22 pages.

Comparison of gene expressions between ProgenMixII and ProgenMixIII

ProgenMixIII has Higher Insulin Expression and More PDX1/Insulin co-staining than ProgenMixII PDX1/NKX6.1/C-pep Stage 3 thaw PDX1/insulin/glucagon Stage 4 thaw PDX1/NKX6.1/C-pep
Stage 4 thaw PDX1/insulin/glucagon
Stage 5 thaw

FIG. 35

GSIS (2.5 mM to 25 mM glucose)

| | SI | Std dev. | |
|---|---|---|---|
| Forumla B (Transwell) | 1.3 | 0.2 | n=10 |
| ProGenMix III (ILCs) | 2.2 | 0.7 | n=4 |
| Human islets | 1.7 | 0.2 | n=5 |

Mouse study #2

PDX1/Glucagon/insulin

ITSNNR to ITSEK

PDX1/
insulin/
glucagon

ITSNNR to ITSEK

PDX1/NKX6.1

COMPOSITIONS AND METHODS FOR DIFFERENTIATING STEM CELLS INTO CELL POPULATIONS COMPRISING BETA-LIKE CELLS

This application is a continuation of U.S. patent application Ser. No. 15/705,896, filed Sep. 15, 2017, now U.S. Pat. No. 10,138,466, which is a continuation of U.S. patent application Ser. No. 15/187,345, filed Jun. 20, 2016, now U.S. Pat. No. 9,765,302, which is a continuation of U.S. patent application Ser. No. 14/858,465, filed Sep. 18, 2015, now U.S. Pat. No. 9,371,516, which claims priority to provisional application No. 62/052,894, filed Sep. 19, 2014 and 62/173,759, filed Jun. 10, 2015, each of which is herein incorporated by reference in its entirety.

FIELD

Methods, kits, compositions, and systems are provided for culturing pluripotent stem cells to produce populations of cells comprising beta-like cells (e.g., pancreatic lineage, glucose-responsive, monohormonal, and/or insulin-producing). In particular, culture conditions are provided that result in the generation of beta-like cells from a starting culture of human pluripotent stem cells.

BACKGROUND

Type I diabetes is an autoimmune disease of humans caused by destruction of pancreatic islet β cells. Transplantations of whole pancreas or isolated islet cells are effective treatments for Type I diabetes to restore insulin independence, when combined with immunosuppressive therapy Successful transplantation of isolated islets from human cadaver donors is a proof-in-principle that a cell-based therapy for human diabetes can be successful. However, the lack of available organs and islet cells has restricted this therapy to very few patients. The amount of islet cells which can be harvested from human cadavers is extremely limited. Therefore, technologies capable of producing significant quantities of cells of the pancreatic lineage are highly desirable.

Stem cells are cells that are capable of differentiating into many cell types. Embryonic stem cells are derived from embryos and are potentially capable of differentiation into all of the differentiated cell types of a mature body. Certain types of stem cells are "pluripotent," which refers to their capability of differentiating into many cell types. One type of pluripotent stem cell is the human embryonic stem cell (hESC), which is derived from a human embryonic source. Human embryonic stem cells are capable of indefinite proliferation in culture, and therefore, are an invaluable resource for supplying cells and tissues to repair failing or defective human tissues in vivo.

Similarly, induced pluripotent stem (iPS) cells, which may be derived from non-embryonic sources, can proliferate without limit and differentiate into each of the three embryonic germ layers. It is understood that iPS cells behave in culture essentially the same as ESCs. Human iPS cells and ES cells express one or more pluripotent cell-specific markers, such as Oct-4, SSEA-3, SSEA-4, Tra 1-60, Tra 1-81, and Nanog (Yu et al. Science, Vol. 318. No. 5858, pp. 1917-1920 (2007); herein incorporated by reference in its entirety). Also, recent findings of Chan, suggest that expression of Tra 1-60, DNMT3B, and REX1 can be used to positively identify fully reprogrammed human iPS cells, whereas alkaline phosphatase, SSEA-4, GDF3, hTERT, and NANOG are insufficient as markers of fully reprogrammed human iPS cells. (Chan et al., Nat. Biotech. 27:1033-1037 (2009); herein incorporated by reference in its entirety). Subsequent references herein to hESCs and the like are intended to apply with equal force to iPS cells.

Under nonselective culture conditions, it has been previously demonstrated that a wide variety of stem cells, including mouse embryonic stem cells and hESCs, differentiate spontaneously into cells of many lineages including the pancreatic lineage. Such differentiated cells can express the pancreatic duodenal homeobox 1 (PDX1) gene, a transcription factor specifying the pancreatic lineage, and can also express insulin. However, without selective conditions, stem cells will spontaneously and simultaneously differentiate in the same culture dish into a wide variety of different lineages with only a small proportion of the cells being differentiated towards any particular lineage.

Culture systems that allow the spontaneous differentiation of hESCs into insulin-staining cells have been reported (Assady, S. et al., Insulin production by human embryonic stem cells. Diabetes 50, 1691-1697 (2001); and Segev, H. et al., Differentiation of human embryonic stem cells into insulin-producing clusters. Stem Cells 22, 265-274 (2004); herein incorporated by reference in their entireties). However, these studies neither investigated endoderm marker expression nor demonstrated development of cells possessing stereotypical characteristics of β cells: simultaneous expression of C-peptide and PDX1, which is required for pancreas formation and co-activates the insulin promoter (Jonsson, J. et al., Insulin-promoter-factor 1 is required for pancreas development in mice. Nature 371, 606-609 (1994); herein incorporated by reference in its entirety). Because non-β cells such as neuronal cells, may express insulin (Sipione, S. et al., Insulin expressing cells from differentiated embryonic stem cells are not β cells. Diabetologia 47, 499-508 (2004); herein incorporated by reference in its entirety), and insulin present in the culture media may be taken up into other cell types under certain conditions in vitro (Rajagopal, J. et al., Insulin staining of ES cell progeny from insulin uptake. Science 299, 363 (2003); herein incorporated by reference in its entirety), it is important that the endoderm and pancreatic origin of insulin-staining cells derived from hESCs be ascertained.

Spontaneous differentiation of hESCs has produced PDX1$^+$/FOXA2$^+$ cells and co-transplantation of these differentiated cells with mouse dorsal pancreas (E13.5) produced PDX1$^+$/insulin$^+$ cells, and co-staining of insulin and C-peptide was observed (Brolen, G. K. et al., Signals from the embryonic mouse pancreas induce differentiation of human embryonic stem cells into insulin-producing β-cell-like cells. Diabetes 54, 2867-2874 (2005); herein incorporated by reference in its entirety). Thus, pancreatic lineage cells can be induced from spontaneously differentiating hESCs by signals emanating from the embryonic pancreas. However, the experimental methods used to reach such observations would be impractical to adopt into a high-throughput culture protocol. Moreover, the nature of the molecular signals was not revealed by the study. In addition, unselected stem cell populations are tumorigenic, meaning that they will generate non-malignant tumors, known as teratomas, in immunodeficient animals like undifferentiated ES cells do.

Several studies have evaluated the effects of growth factors on hESC differentiation to endoderm (Schuldiner, M. et al., Proc Natl Acad Sci USA 97, 11307-11312 (2000) and D'Amour, K. A. et al. Nat. Biotechnol. 23, 1534-1541 (2005); herein incorporated by reference in their entireties).

However, highly efficient differentiation to pancreatic precursors and islet cells has not been achievable. Furthermore, insulin producing cells generated using previously reported methods are less responsive to glucose, in that, they appear less functionally mature than adult human β cells and are believed to possess a phenotype more like immature β cells.

SUMMARY

Methods, kits, compositions, and systems are provided for culturing pluripotent stem cells to produce populations of cells comprising beta-like cells (e.g., pancreatic lineage, glucose-responsive, and/or insulin-producing). In particular, culture conditions are provided that result in the generation of beta-like cells from a starting culture of human pluripotent stem cells.

In some embodiments, provided herein are methods of culturing pluripotent stem cells (e.g., human cells) to produce cells of the pancreatic lineage (e.g., beta-like cells or a cell population comprising beta-like cells) comprising: (a) culturing the stem cells in a chemically defined medium, fibroblast growth factor (e.g., FGF2 (basic fibroblast growth factor (bFGF)), FGF4, FGF7, FGF10, etc.), Activin A, and bone morphogenetic protein (e.g., BMP4 (e.g., a high concentration of BMP4)); (b) culturing the cells from step (a) in the presence of chemically defined medium comprising insulin, transferrin, selenium, a fibroblast growth factor (e.g., FGF2, FGF4, FGF7, FGF10, etc.) and nicotinamide; (c) culturing the cells from step (b) in the presence of a chemically defined medium comprising insulin, transferrin, and selenium; retinoic acid; a bone morphogenetic protein (e.g., BMP4) inhibitor (e.g., Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin, and analogues thereof) (e.g., high concentration (e.g., >200 ng/ml); and nicotinamide; and (d) culturing the cells from step (c) in the presence of a serum-free medium (e.g., B27), an insulin-like growth factor (e.g., both IGF I and IGF II), fibroblast growth factor (e.g., FGF2, FGF4, FGF7, FGF10, etc.), insulin, nicotinamide, exendin-4 and/or GLP-1, a transforming growth factor (TGF)-beta receptor (e.g., actin-like kinase 5) inhibitor (e.g., ALK5i, ALK5i II, GW-6004, A 83-01, D 4476, GW 788388, LY 365947, RepSox, SB 431542, SB 525334, SD 208, etc. (See, e.g., Tocris Bioscience), and one or more agents that increase cAMP (e.g., forskolin, glucagon, IBMX, GLP-1/gastrin dual peptide, glucagon/GLP-1 dual peptide, glucagon/GLP-1 dual peptide, etc.). In some embodiments, agents increase cAMP by activating adenyl cyclase, while other compounds inhibit cAMP degradation. In some embodiments, methods further comprise: (e) maintaining the cells of the pancreatic lineage (e.g., for 1 day, 2 days, 4 days, 5 days, 6 days, 7 days, 8 days, 9 days, 10 days, 15 days, 20 days, 25 days, 30 days, 35 days, 40 days, 50 days, 60 days, 70 days, 80 days, 90 days, 100 days, or lengths or ranges therein) by culturing the cells from step (d) in the presence of a serum-free medium (e.g., B27), an insulin-like growth factor (e.g., IGF I), fibroblast growth factor (e.g., FGF2, FGF7, etc.), insulin, nicotinamide, exendin-4 and/or GLP-1, and one or more agents that increase cAMP (e.g., forskolin, glucagon, IBMX, GLP-1/gastrin dual peptide, glucagon/GLP-1 dual peptide, etc.). In some embodiments, step (e) comprises maintaining the cells of the pancreatic lineage (e.g., for 1-14 days) in the presence of a serum-free medium (e.g., B27), an insulin-like growth factor (e.g., IGF I), fibroblast growth factor (e.g., FGF2, FGF7, etc.), insulin, nicotinamide, exendin-4 and/or GLP-1, and forskolin, followed by a period (e.g., for 1-14 days) where forskolin is combined with, or substituted with, one or more of IBMX, zinc ($ZnSO_4$), high glucose, glucosamine, thyroid hormone, betatrophin, PUGNAc, glutathione, N-acetyl-L-cysteine, vitamin C, and vitamin E, and/or caerulein (TANAKA, et. Al., Proc Natl Acad Sci USA. 1999 Sep. 14; 96(19):10857-62; herein incorporated by reference in its entirety). In some embodiments, during step (e), cells are transferred from Transwells to AggreWells (e.g., U.S. Pub. No. 2011/0086375; U.S. Pub. No. 2010/0068793; U.S. Pub. No. 2012/0149051; herein incorporated by reference in their entireties). In some embodiments, provided herein are methods of culturing pluripotent stem cells (e.g., human cells) to produce cells of the pancreatic lineage (e.g., beta-like cells or a cell population comprising beta-like cells) comprising: (a) culturing the stem cells in a chemically defined medium, basic fibroblast growth factor, Activin A, and BMP4; (b) culturing the cells from step (a) in the presence of chemically defined ITS medium FGF7, and nicotinamide; (c) culturing the cells from step (b) in the presence of a chemically defined ITS medium; retinoic acid; Noggin; and nicotinamide; and (d) culturing the cells from step (c) in the presence of a B27 serum-free medium, IGF I, IGF II, FGF7, insulin, nicotinamide, exendin-4, an ALK5i II, and forskolin. In some embodiments, methods further comprise: (e) maintaining the cells of the pancreatic lineage (e.g., for 1 day, 2 days, 4 days, 5 days, 6 days, 7 days, 8 days, 9 days, 10 days, 15 days, 20 days, 25 days, 30 days, 35 days, 40 days, 50 days, 60 days, 70 days, 80 days, 90 days, 100 days, or lengths or ranges therein) by culturing the cells from step (d) in the presence of B27 serum-free medium, IGF I, FGF7, insulin, nicotinamide, exendin-4, and forskolin. In some embodiments, step (e) comprises maintaining the cells of the pancreatic lineage (e.g., for 1-14 days) in the presence of a serum-free medium (e.g., B27), an insulin-like growth factor (e.g., IGF I), fibroblast growth factor (e.g., FGF7), insulin, nicotinamide, exendin-4 and/or GLP-1, and forskolin, followed by a period (e.g., for 1-14 days) where forskolin is combined with, or substituted with, by one or more of IBMX, zinc ($ZnSO_4$), high glucose, glucosamine, thyroid hormone, betatrophin, PUGNAc, glutathione, N-acetyl-L-cysteine, vitamin C, vitamin E, and/or caerulein (TANAKA, et. Al., Proc Natl Acad Sci USA. 1999 Sep. 14; 96(19): 10857-62; herein incorporated by reference in its entirety). In some embodiments, during step (e), cells are transferred from Transwells to Aggrewells.

In some embodiments, the stem cells are human pluripotent stem cells. In some embodiments, the stem cells are selected from the group consisting of human embryonic stem cells and human induced pluripotent stem cells. In some embodiments, the chemically defined medium is serum free.

In some embodiments, the chemically defined medium of step (a) comprises DMEM/F12 (Invitrogen 11330-057), nonessential amino acids (Invitrogen, 11140), L-glutamine (Invitrogen, 25030-081), and 2-mercaptoethanol (Invitrogen, 21985). In some embodiments, the chemically defined medium of step (a) comprises a final concentration of 0.1-10 mM (e.g., 0.1 . . . 0.2 . . . 0.5 . . . 1 . . . 2 . . . 5 . . . 10, or ranges or values therein) nonessential amino acids (Invitrogen, 11140), 0.1-10 mM (e.g., 0.1 . . . 0.2 . . . 0.5 . . . 1 . . . 2 . . . 5 . . . 10, or ranges or values therein) L-glutamine (Invitrogen, 25030-081), and 0.01-1.0 mM (e.g., 0.01 . . . 0.02 . . . 0.05 . . . 0.1 . . . 0.2 . . . 0.5 . . . 1.0, or ranges or values therein) 2-mercaptoethanol (Invitrogen, 21985) in DMEM/F12 (Invitrogen 11330.057). In some embodiments, the chemically defined medium of step (a) comprises a final concentration of 8-12 mM nonessential amino acids (Invitrogen, 11140), 0.8-1.2 mM L-glutamine (Invitrogen, 25030-081), and 0.08-0.12 mM 2-mercaptoethanol (Invitrogen, 21985) in DMEM/F12 (Invitrogen 11330.057). In some embodiments, the chemically defined medium of step (a) comprises a final concentration of about 1 mM nonessential amino acids (Invitrogen, 11140), about 2 mM L-glutamine (Invitrogen, 25030-081), and about 0.11 mM 2-mercaptoethanol (Invitrogen, 21985) in DMEM/F12 (Invitrogen 11330.057). In some embodiments, the chemically defined medium of step (a) comprises a final concentration of 1 mM nonessential amino acids (Invitrogen, 11140), 2 mM L-glutamine (Invitrogen, 25030-081), and 0.11 mM 2-mercaptoethanol (Invitrogen, 21985) in DMEM/F12 (Invitrogen 11330.057).

In some embodiments, step (a) comprises culturing the stem cells in a chemically defined medium (e.g., above) along with 10-1000 ng/ml (e.g., 10 . . . 20 . . . 50 . . . 100 . . . 200 . . . 500 . . . 1000, or ranges or values therein) fibroblast growth factor (e.g., FGF2), 10-1000 ng/ml (e.g., 10 . . . 20 . . . 50 . . . 100 . . . 200 . . . 500 . . . 1000, or ranges or values therein) Activin A, and 0.5-50 ng/ml (e.g., 5 . . . 10 . . . 20 . . . 50 . . . 100 . . . 200 . . . 500, or ranges or values therein) bone morphogenetic protein (e.g., BMP4). In some embodiments, step (a) comprises culturing the stem cells in a chemically defined medium (e.g., above) along with 80-120 ng/ml fibroblast growth factor (e.g., FGF2), 80-120 ng/ml Activin A, and 30-50 ng/ml bone morphogenetic protein (e.g., BMP4). In some embodiments, step (a) comprises culturing the stem cells in a chemically defined medium (e.g., above) along with about 100 ng/ml fibroblast growth factor (e.g., FGF2), about 100 ng/ml Activin A, and about 50 ng/ml bone morphogenetic protein (e.g., BMP4). In some embodiments, step (a) comprises culturing the stem cells in a chemically defined medium (e.g., above) along with 100 ng/ml fibroblast growth factor (e.g., FGF2), 100 ng/ml Activin A, and 50 ng/ml bone morphogenetic protein (e.g., BMP4).

In some embodiments, the fibroblast growth factor of step (a) is basic fibroblast growth factor (bFGF). In some embodiments, the fibroblast growth factor of step (a) is FGF2. In some embodiments, the fibroblast growth factor of step (a) is FGF4. In some embodiments, the fibroblast growth factor of step (a) is FGF10.

In some embodiments, the bone morphogenetic protein of step (a) is BMP4.

In some embodiments, step (a) comprises culturing the stem cells for at least 12 hours. In some embodiments, step (a) comprises culturing the stem cells for less than 14 days. In some embodiments, the stem cells are cultured under step (a) conditions for 1-5 days (e.g., 1 day, 2 days, 3 days, 4 days, 5 days, and ranges therein). In some embodiments, the stem cells are cultured under step (a) conditions for 1-5 days (e.g., 2-4 days, 3 days, etc.). In some embodiments, medium is changed periodically (e.g., daily, twice daily, semi-daily, etc.) during the culture period. In some embodiments, step (a) comprises culturing the stem cells for a duration of three (3) days, and the medium is changed daily (e.g., once daily).

In some embodiments, step (b) comprises culturing cells in the presence of chemically defined medium comprising insulin, transferrin, and selenium (1000× dilution of ITS premix, BD Biosciences, 354351), a 5-100 ng/ml (e.g., 5 . . . 10 . . . 20 . . . 50 . . . 100 . . . 200 . . . 500, or ranges or values therein) fibroblast growth factor (e.g., FGF7) and 1-100 mM (e.g., 1 . . . 2 . . . 5 . . . 10 . . . 20 . . . 50 . . . 100, or ranges or values therein) nicotinamide. In some embodiments, step (b) comprises culturing cells in the presence of chemically defined medium comprising insulin, transferrin, and selenium (1000× dilution of ITS premix, BD Biosciences, 354351), a 40-60 ng/ml fibroblast growth factor (e.g., FGF7) and 8-12 mM nicotinamide. In some embodiments, step (b) comprises culturing cells in the presence of chemically defined medium comprising insulin, transferrin, selenium (1000× dilution of ITS premix, BD Biosciences, 354351), about 50 ng/ml fibroblast growth factor (e.g., FGF7) and about 10 mM nicotinamide. In some embodiments, step (b) comprises culturing cells in the presence of chemically defined medium comprising insulin, transferrin, and selenium (1000× dilution of ITS premix, BD Biosciences, 354351), a 50 ng/ml fibroblast growth factor (e.g., FGF7) and 10 mM nicotinamide.

In some embodiments, the fibroblast growth factor of step (b) is FGF7.

In some embodiments, step (b) comprises culturing the stem cells for at least 12 hours. In some embodiments, step (b) comprises culturing the stem cells for less than 14 days. In some embodiments, the stem cells are cultured under step (b) conditions for 1-6 days (e.g., 1 day, 2 days, 3 days, 4 days, 5 days, 6 days, and ranges therein). In some embodiments, the stem cells are cultured under step (b) conditions for 1-5 days (e.g., 2-4 days, 3 days, etc.). In some embodiments, medium is changed periodically (e.g., daily, twice daily, semi-daily, etc.) during the culture period. In some embodiments, step (b) comprises culturing the stem cells for a duration of three (3) days, and the medium is changed daily (e.g., once daily).

In some embodiments, step (c) comprises culturing cells in the presence of a chemically defined medium comprising insulin, transferrin and selenium (1000× dilution of ITS premix, BD Biosciences, 354351), 0.2-20 µM (e.g., 0.2 . . . 0.5 . . . 1 . . . 2 . . . 5 . . . 10 . . . 20, or ranges or values therein) retinoic acid, 200-3000 ng/ml (e.g., 200 . . . 300 . . . 500 . . . 1000 . . . 3000, or ranges or values therein) of a bone morphogenetic protein (e.g., BMP4) inhibitor (e.g., Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin, and analogues thereof), and 1-100 mM (e.g., 1 . . . 2 . . . 5 . . . 10 . . . 20 . . . 50 . . . 100, or ranges or values therein) nicotinamide. In some embodiments, step (c) comprises culturing cells in the presence of a chemically defined medium comprising insulin, transferrin and selenium (1000× dilution of ITS premix, BD Biosciences, 354351), 1-10 µM retinoic acid, 240-360 ng/ml of a bone morphogenetic protein (e.g., BMP4) inhibitor (e.g., Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin, and analogues thereof), and 8-12 mM nicotinamide. In some embodiments, an amount of a bone morphogenetic protein (e.g., BMP4) inhibitor (e.g., Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin, and analogues thereof) is used that produces a similar effect to >200 ng/ml Noggin (e.g., 240-360 ng/ml). In some embodiments, step (c) comprises culturing cells in the presence of a chemically defined medium comprising insulin, transferrin and selenium (1000× dilution of ITS premix, BD Biosciences, 354351), about 2 µM retinoic acid, about 300 ng/ml of a bone morphogenetic protein (e.g., BMP4) inhibitor (e.g., Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin, and analogues thereof), and about 10 mM nicotinamide. In some embodiments, step (c) comprises culturing cells in the presence of a chemically defined medium comprising insulin, transferrin and selenium (1000× dilution of ITS premix, BD Biosciences, 354351), 2 µM retinoic acid, 300 ng/ml of a bone morphogenetic protein (e.g., BMP4) inhibitor (e.g., Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin, and analogues thereof), and 10 mM nicotinamide.

In some embodiments, the bone morphogenetic protein of step (c) is a BMP4 inhibitor. In some embodiments, the bone morphogenetic protein of step (c) is Noggin.

In some embodiments, step (c) comprises culturing the stem cells for at least 12 hours. In some embodiments, step (c) comprises culturing the stem cells for less than 14 days. In some embodiments, the stem cells are cultured under step (b) conditions for 1-10 days (e.g., 1 day, 2 days, 3 days, 4 days, 5 days, 6 days, 7 days, 8 days, 9 days, 10 days, and ranges therein). In some embodiments, the stem cells are cultured under step (b) conditions for 1-6 days (e.g., 3-5 days, 4 days, etc.). In some embodiments, medium is changed periodically (e.g., daily, twice daily, semi-daily, etc.) during the culture period. In some embodiments, step (c) comprises culturing the stem cells for a duration of four (4) days, and the medium is changed daily (e.g., once daily).

In some embodiments, step (d) comprises culturing cells in the presence of a serum-free medium (e.g., 50× dilution of B27, Gibco, 05-1295A), 15-1500 ng/ml (e.g., 15 . . . 50 . . . 100 . . . 200 . . . 500 . . . 1000 . . . 1500, or ranges or values therein) insulin-like growth factor I, 80-8000 ng/ml (e.g., 80 . . . 100 . . . 200 . . . 500 . . . 1000 . . . 2000 . . . 8000, or ranges or values therein) insulin-like growth factor II, 1-100 ng/ml (e.g., 1 . . . 2 . . . 5 . . . 10 . . . 20 . . . 50 . . . 100, or ranges or values therein) fibroblast growth factor (e.g., FGF7), 0.4-40 ng/ml (e.g., 0.4 . . . 1 . . . 2 . . . 5 . . . 10 . . . 20 . . . 40, or ranges or values therein) insulin, 1-100 mM (e.g., 1 . . . 2 . . . 5 . . . 10 . . . 20 . . . 50 . . . 100, or ranges or values therein) nicotinamide, 1-100 nM (e.g., 1 . . . 2 . . . 5 . . . 10 . . . 20 . . . 50 . . . 100, or ranges or values therein) exendin-4 and/or GLP-1, 0.1-10 µM (e.g., 0.1 . . . 0.2 . . . 0.5 . . . 1 . . . 2 . . . 5 . . . 10, or ranges or values therein) of a TGF-beta receptor (e.g., actin-like kinase 5) inhibitor (e.g., ALK5i, ALK5i II, GW-6004, A 83-01, D 4476, GW 788388, LY 365947, RepSox, SB 431542, SB 525334, SD 208, etc. (See, e.g., Tocris Bioscience)), and 2.5-250 µM (e.g., 2.5 . . . 5 . . . 10 . . . 20 . . . 50 . . . 100 . . . 250, or ranges or values therein) of one or more agents that increase cAMP (e.g., forskolin, glucagon, IBMX, GLP-1/gastrin dual peptide, glucagon/GLP-1 dual peptide, etc.). In some embodiments, step (d) comprises culturing cells in the presence of a serum-free medium (e.g., 50× dilution of B27, Gibco, 05-1295A), 135-165 ng/ml insulin-like growth factor I, 80-8000 ng/ml insulin-like growth factor II, 8-12 ng/ml fibroblast growth factor (e.g., FGF7), 3.2-4.8 ng/ml insulin, 8-12 mM nicotinamide, 8-12 nM exendin-4 and/or GLP-1, 0.8-1.2 µM of a TGF-beta receptor (e.g., actin-like kinase 5) inhibitor (e.g., ALK5i, ALK5i II, GW-6004, A 83-01, D 4476, GW 788388, LY 365947, RepSox, SB 431542, SB 525334, SD 208, etc. (See, e.g., Tocris Bioscience)), and 10-30 µM of one or more agents that increase cAMP (e.g., forskolin, glucagon, IBMX, GLP-1/gastrin dual peptide, glucagon/GLP-1 dual peptide, etc.). In some embodiments, an amount of one or more agents that increase cAMP (e.g., forskolin, glucagon, IBMX, GLP-1/gastrin dual peptide, glucagon/GLP-1 dual peptide, etc.) is used that produces a similar effect to 20-30 µM of forskolin. In some embodiments, an amount of a TGF-beta receptor (e.g., actin-like kinase 5) inhibitor (e.g., ALK5i, ALK5i II, GW-6004, A 83-01, D 4476, GW 788388, LY 365947, RepSox, SB 431542, SB 525334, SD 208, etc. (See, e.g., Tocris Bioscience)) is used that produces a similar effect to 0.8-1.2 µM of ALK5i II. In some embodiments, step (d) comprises culturing cells in the presence of a serum-free medium (e.g., 50× dilution of B27, Gibco, 05-1295A), about 150 ng/ml insulin-like growth factor I, about 800 ng/ml insulin-like growth factor II, about 10 ng/ml fibroblast growth factor (e.g., FGF7), about 4 ng/ml insulin, about 10 mM nicotinamide, about 10 nM exendin-4 and/or GLP-1, about 1 µM of a TGF-beta receptor (e.g., actin-like kinase 5) inhibitor (e.g., ALK5i, ALK5i II, GW-6004, A 83-01, D 4476, GW 788388, LY 365947, RepSox, SB 431542, SB 525334, SD 208, etc. (See, e.g., Tocris Bioscience)), and about 25 µM of one or more agents that increase cAMP (e.g., forskolin, glucagon, IBMX, GLP-1/gastrin dual peptide, glucagon/GLP-1 dual peptide, etc.). In some embodiments, the concentration of agents that increase cAMP is one that produces an equivalent effect to about 25 µM forskolin. In some embodiments, step (d) comprises culturing cells in the presence of a serum-free medium (e.g., 50× dilution of B27, Gibco, 05-1295A), 150 ng/ml insulin-like growth factor I, 800 ng/ml insulin-like growth factor II, 10 ng/ml fibroblast growth factor (e.g., FGF7), 4 ng/ml insulin, 10 mM nicotinamide, 10 nM exendin-4 and/or GLP-1, 1 µM of a TGF-beta receptor (e.g., actin-like kinase 5) inhibitor (e.g., ALK5i, ALK5i II, GW-6004, A 83-01, D 4476, GW 788388, LY 365947, RepSox, SB 431542, SB 525334, SD 208, etc. (See, e.g., Tocris Bioscience)), and 25 µM of one or more agents that increase cAMP (e.g., forskolin, glucagon, IBMX, GLP-1/gastrin dual peptide, glucagon/GLP-1 dual peptide, etc.). In some embodiments, one or more agents that increase cAMP are included in a concentration that produces an equivalent effect to 25 µM (e.g., 100 µM IBMX).

In some embodiments, the fibroblast growth factor of step (d) is FGF7. In some embodiments, the TGF beta inhibitor of step (d) is ALK5i II.

In some embodiments, step (d) comprises culturing the stem cells for at least 2 days. In some embodiments, step (d) comprises culturing the stem cells for less than 20 days. In some embodiments, cells are cultured under step (d) conditions for 4-14 days (e.g., 4 days, 5 days, 6 days, 7 days, 8 days, 9 days, 10 days, 11 days, 12 days, 13 days, 14 days, and ranges therein). In some embodiments, cells are cultured under step (d) conditions for 6-10 days (e.g., 7-9 days, 8 days). In some embodiments, medium is changed periodically (e.g., daily, twice daily, semi-daily, etc.) during the culture period. In some embodiments, step (d) comprises culturing the stem cells for a duration of eight (8) days, and the medium is changed daily (e.g., once daily).

In some embodiments, cells remain in the culture conditions of one or more of the above steps (e.g., step (a), step (b), step (c), step (d)) for up to 100 days (e.g., 5 days, 10 days, 15 days, 20 days, 25 days, 30 days, 40 days, 50 days, 60 days, 70 days, 80 days, 90 days, 100 days, and ranges and durations therein).

In some embodiments, embodiment, cells are cultured in steps (a)-(d) for a combined 8-30 days (e.g., about 8 days, about 10 days, about 12 days, about 14 days, about 16 days, about 18 days, about 20 days, about 22 days, about 24 days, about 26 days, about 28 days, about 30 days, and ranges therein).

In some embodiments, provided herein are methods of culturing pluripotent stem cells (e.g., human cells) to produce cells of the pancreatic lineage (e.g., beta-like cells or a cell population comprising beta-like cells) comprising: (A) culturing pluripotent stem cells under a first set of conditions (e.g., conditions from step (a) above to produce definitive endoderm cells; (B) culturing the definitive endoderm cells from step (A) under a second set (e.g., conditions from step (b) above) and third set (e.g., conditions from step (c) above) of conditions to produce posterior foregut cells and pancreatic epithelium cells or pancreatic progenitors (e.g., as defined by expression profile; and (C) culturing the posterior foregut cells from step (B) under a fourth set of conditions to produce a population of cells enriched for endocrine β cells. In some embodiments, step (A) produces an anterior primitive streak. In some embodiments, during step (A) cells progress cells go through the following process: (1) embryonic stem cells/pluripotent stem cells; (2) anterior primitive streak; (3) mesendoderm; (4) definitive endoderm. In some embodiments, posterior foregut cells from step (B) are pancreatic epithelium cells.

In some embodiments, the method further comprises the step of (e) maintaining the cells of the pancreatic lineage for 1-50 days by culturing the cells from step (d) in the presence of a serum-free medium, B27, ALK5, Forskolin, $ZnSO_4$, T3, heparin, and antioxidant, and a P13 kinase inhibitor. In some embodiments, the P13 kinase inhibitor is LY294002 (e.g., at a concentration of 1-50 µM (e.g., 5-25 µM, 10-20 µM, 10-15 µM, etc.)), and the antioxidant is glutathione. In some embodiments, antioxidants include, but are not limited to, N-acetyl-L-cysteine (NAC), aminoguanidine (AG), AGI-1067, vitamin C, vitamin E, or a-lipoic acid. In some embodiments, the P13 kinase inhibitor is one or more of, for example, wortmannin, piceatannol, hypericin, Akt Inhibito, IC-87114, myricetin, PIK-75, free base, TG100-115, XL-147 derivative 2, toyocamycin, WHI-P 154, GSK2126458, fisetin, 7β-hydroxy Wortmannin, miltefosine, BAG 956, SF1126, CH5132799, CAY10505, quercetin, 3',4',7-Trihydroxyisoflavone, compound 15e, PI 3-Kβ Inhibitor VI, TGX-221, PIK-90, PIK-294, LY-294,002 hydrochloride, GSK 1059615, PF-04691502, PP121, PI 3-Kα Inhibitor VIII, PIK-293, BYL719, PI3K/HDAC Inhibitor, demethoxyviridiol, viridiol, TG 100713, PX-866, BIP-135, PF-05212384, XL-147 derivative 1, or GDC-0941. In some embodiments, the method further comprises the step of treating the cells with a dissociating agent prior to the maintaining (e.g., EDTA or a protease (e.g., Dispase or Accutase)). In some embodiments, the method generates islet-like clusters (e.g., cultured in suspension).

Further embodiments provide a method of culturing human pluripotent stem cells to produce a cell population comprising pancreatic β-like cells comprising: (a) culturing the stem cells for 2-4 days in a chemically defined medium, basic fibroblast growth factor, Activin A, BMP4, LY294002, and Matrigel; (b) culturing the cells from step (a) for 2-4 days in the presence of chemically defined ITS medium, FGF7, nicotinamide, and Matrigel; (c) culturing the cells from step (b) for 3-5 days in the presence of a chemically defined ITS medium, retinoic acid, Noggin, nicotinamide, and Matrigel; (d) culturing the cells from step (c) for 6-10 days in the presence of a B27 serum-free medium, IGF I, IGF II, FGF7, insulin, Noggin, nicotinamide, exendin-4, ALK5i II, forskolin, and Matrigel; and (e) maintaining the cells of the pancreatic lineage for 1-50 days by culturing the cells from step (d) in the presence of a serum-free medium, ALK5, Forskolin, ZnSO4, T3, B27, heparin, and antioxidant, and a P13 kinase inhibitor. In some embodiments, step (c) is performed in two steps (e.g., a first step of culturing in the presence of chemically defined ITS medium; retinoic acid; and Noggin for 2 days and then a second step of culturing in the presence of chemically defined ITS medium, EGF, and FGF7 for two days). In some embodiments, step (d) further comprises EGF. In some embodiments, step (e) further comprises the addition of Warfarin.

Additional embodiments provide a method of culturing human pluripotent stem cells to produce a cell population comprising pancreatic β-like cells comprising: (a) culturing the stem cells for 2-4 days in a chemically defined medium, basic fibroblast growth factor, Activin A, BMP4, LY294002, and Matrigel; (b) culturing the cells from step (a) for 2-4 days in the presence of chemically defined ITS medium, FGF7, nicotinamide, and Matrigel; (c) culturing the cells from step (b) for 2 days in the presence of a chemically defined ITS medium, retinoic acid, Noggin, nicotinamide, and Matrigel; (d) culturing the cell of step (c) for 2 days in the presence of chemically defined ITS medium, EGF, and FGF7; (e) culturing the cells from step (d) for 6-10 days in the presence of a B27 serum-free medium, IGF I, IGF II, FGF7, insulin, Noggin, nicotinamide, exendin-4, ALK5i II, forskolin, and Matrigel; and (f) maintaining the cells of the pancreatic lineage for 1-50 days by culturing the cells from step (e) in a suspension culture in the presence of a serum-free medium, ALK5, Forskolin, ZnSO4, T3, B27, heparin, and antioxidant, Warfarin, and a P13 kinase inhibitor.

In some embodiments, kits for culturing pluripotent stem cells (e.g., human cells) to produce cells of the pancreatic lineage (e.g., beta-like cells or a cell population comprising beta-like cells) are provided. A kit may comprise reagents for performing one or more culture steps (e.g., as set for in the methods above). In some embodiments, reagents for performing a culture step (see, e.g., step (a), step (b), step (c), or step (d) above) are provided in a single container (e.g., tube, vial, etc.). In some embodiments, gents for performing a culture step (see, e.g., step (a), step (b), step (c), and step (d) above) are provided in a two or more containers (e.g., tubes, vials, etc.) that are packaged together (e.g., in an envelope, in a box, etc.). In some embodiments, a kit comprises reagents for performing two or more culture steps (e.g., as set for in the methods above). In some embodiments, reagents for separate steps are in separate containers and/or packaging (e.g., one container per step, multiple containers per step).

In some embodiments, a kit comprises all the reagents needed to perform the methods described herein, or a step thereof. In some embodiments, in addition to the kits provided herein a user provides one or more reagents for performing the methods described herein.

In some embodiments, a kit for performing step (a), as described above, is provided. In some embodiments, a kit is provided that comprises fibroblast growth factor (e.g., bFGF, etc.), Activin A, and bone morphogenetic protein (e.g., BMP4). In some embodiments, fibroblast growth factor (e.g., bFGF, etc.), Activin A, and bone morphogenetic protein (e.g., BMP4) are provided in a single container (e.g., tube, vial, etc.). In some embodiments, two or more of fibroblast growth factor (e.g., bFGF, etc.), Activin A, and bone morphogenetic protein (e.g., BMP4) are provided in a single container (e.g., tubes, vials, etc.). In some embodiments, two or more of fibroblast growth factor (e.g., bFGF, etc.), Activin A, and bone morphogenetic protein (e.g., BMP4) are provided in separate containers (e.g., tubes, vials, etc.). In some embodiments, multiple containers containing separate reagents for performing step (a), as described above are contained within the same packaging (e.g., box).

In some embodiments, a kit comprises one or more of fibroblast growth factor (e.g., bFGF, etc.), Activin A, and bone morphogenetic protein (e.g., BMP4). In some embodiments, fibroblast growth factor (e.g., bFGF, etc.) is provided in a volume between 40 µl and 4 ml (40 µl . . . 100 µl . . . 200 µl . . . 400 µl . . . 1 ml . . . 2 ml . . . 4 ml, and values and ranges therein) and/or at a concentration of between 10 µg/ml and 1 mg/ml (e.g., 10 µg/ml . . . 20 µg/ml . . . 50 µg/ml . . . 100 µg/ml . . . 200 µg/ml . . . 500 µg/ml . . . 1 mg/ml, and values and ranges therein). In some embodiments, Activin A is provided in a volume between 40 µl and 4 ml (40 µl . . . 100 µl . . . 200 µl . . . 400 µl . . . 1 ml . . . 2 ml . . . 4 ml, and values and ranges therein) and/or at a concentration of between 1 µg/ml and 100 µg/ml (e.g., 1 µg/ml . . . 2 µg/ml . . . 5 µg/ml . . . 10 µg/ml . . . 20 µg/ml . . . 50 µg/ml . . . 100 µg/ml, and values and ranges therein). In some embodiments, bone morphogenetic protein (e.g., BMP4) is provided in a volume between 20 µl and 2 ml (20 µl . . . 40 µl . . . 100 µl . . . 200 µl . . . 400 µl . . . 1 ml . . . 2 ml, and values and ranges therein) and/or at a concentration of between 1 µg/ml and 100 µg/ml (e.g., 1 µg/ml . . . 2 µg/ml . . . 5 µg/ml . . . 10 µg/ml . . . 20 µg/ml . . . 50 µg/ml . . . 100 µg/ml, and values and ranges therein).

In some embodiments, a kit (e.g., comprising reagents for step (a) above, comprising reagents for methods described herein, etc.) further comprises defined culture medium or reagents for making defined culture medium (e.g., DMEM/F12, nonessential amino acids, L-glutamine, 2-mercaptoethanol, etc.). In some embodiments, a kit does not contain defined culture medium or reagents for making defined culture medium (e.g., DMEM/F12, nonessential amino acids, L-glutamine, 2-mercaptoethanol, etc.), and such reagents are separately provided by a user. In some embodiments, one or more reagents are provided is a dry or powdered form (e.g., lyophilized). In some embodiments, one or more reagents are provided as a liquid (e.g., in solution).

In some embodiments, a kit for performing step (b), as described above, is provided. In some embodiments, a kit is provided that comprises chemically defined medium comprising insulin, transferrin, and selenium (ITS); fibroblast growth factor (e.g., FGF7, bFGF, etc.), and nicotinamide. In some embodiments, chemically defined medium comprising insulin, transferrin, and selenium (ITS); fibroblast growth factor (e.g., FGF7, bFGF, etc.), and nicotinamide are provided in a single container (e.g., vial, tube, etc.). In some embodiments, two or more of ITS, fibroblast growth factor (e.g., FGF7, bFGF, etc.), and nicotinamide are provided in a single container (e.g., tubes, vials, etc.). In some embodiments, two or more of ITS, fibroblast growth factor (e.g., FGF7, bFGF, etc.), and nicotinamide are provided in separate containers (e.g., tubes, vials, etc.). In some embodiments, multiple containers containing separate reagents for performing step (b), as described above, are contained within the same packaging (e.g., box).

In some embodiments, ITS is provided in a volume between 4 µl and 400 µl (4 µl . . . 10 µl . . . 20 µl . . . 40 µl . . . 100 µl . . . 200 µl . . . 400 µl, and values and ranges therein) at a concentration for reconstitution in a volume of 0.5 to 50 ml (e.g., 0.5 ml . . . 1 ml . . . 2 ml . . . 5 ml . . . 10 ml . . . 20 ml . . . 50 ml, and values and ranges therein). In some embodiments, fibroblast growth factor (e.g., FGF7, bFGF, etc.) is provided in a volume between 20 µl and 2 ml (20 µl . . . 40 µl . . . 100 µl . . . 200 µl . . . 400 µl . . . 1 ml . . . 2 ml, and values and ranges therein) and/or at a concentration of between 10 µg/ml and 1 mg/ml (e.g., 10 µg/ml . . . 20 µg/ml . . . 50 µg/ml . . . 100 µg/ml . . . 200 µg/ml . . . 500 µg/ml . . . 1 mg/ml, and values and ranges therein). In some embodiments, nicotinamide is provided in a volume between 40 µl and 4 ml (40 µl . . . 100 µl . . . 200 µl . . . 400 µl . . . 1 ml . . . 2 ml . . . 4 ml, and values and ranges therein) and/or at a concentration of between 100 mM and 10 M (e.g., 100 mM . . . 200 mM . . . 500 mM . . . 1M . . . 2M . . . 5M . . . 10M, and values and ranges therein).

In some embodiments, a kit for performing step (c), as described above, is provided. In some embodiments, a kit is provided that comprises chemically defined medium comprising insulin, transferrin, and selenium (ITS); retinoic acid; a bone morphogenetic protein (e.g., BMP4) inhibitor (e.g., Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin, and analogues thereof); and nicotinamide. In some embodiments, chemically defined medium comprising insulin, transferrin, and selenium (ITS); retinoic acid; a bone morphogenetic protein (e.g., BMP4) inhibitor (e.g., Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin, and analogues thereof); and nicotinamide are provided in a single contained (e.g., tube, vial, etc.). In some embodiments, two or more of ITS, retinoic acid, a bone morphogenetic protein (e.g., BMP4) inhibitor (e.g., Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin, and analogues thereof), and nicotinamide are provided in a single container (e.g., tubes, vials, etc.). In some embodiments, two or more of ITS, retinoic acid, a bone morphogenetic protein (e.g., BMP4) inhibitor (e.g., Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin, and analogues thereof), and nicotinamide are provided in separate containers (e.g., tubes, vials, etc.). In some embodiments, multiple containers containing separate reagents for performing step (c), as described above, are contained within the same packaging (e.g., box).

In some embodiments, ITS is provided in a volume between 4 µl and 400 µl (4 µl . . . 10 µl . . . 20 µl . . . 40 µl . . . 100 µl . . . 200 µl . . . 400 µl, and values and ranges therein) at a concentration for reconstitution in a volume of 0.5 to 50 ml (e.g., 0.5 ml . . . 1 ml . . . 2 ml . . . 5 ml . . . 10 ml . . . 20 ml . . . 50 ml, and values and ranges therein). In some embodiments, nicotinamide is provided in a volume between 40 µl and 4 ml (40 µl . . . 100 µl . . . 200 µl . . . 400 µl . . . 1 ml . . . 2 ml . . . 4 ml, and values and ranges therein) and/or at a concentration of between 100 mM and 10 M (e.g., 100 mM . . . 200 mM . . . 500 mM . . . 1M . . . 2M . . . 5M . . . 10M, and values and ranges therein). In some embodiments, retinoic acid is provided in a volume between 1 µl and 100 µl (1 µl . . . 2 µl . . . 5 µl . . . 10 µl . . . 20 µl . . . 50 µl . . . 100 µl, and values and ranges therein) and/or at a concentration of between 3 mg/ml and 300 mg/ml (e.g., 3 mg/ml . . . 5 mg/ml . . . 10 mg/ml . . . 30 mg/ml . . . 50 mg/ml . . . 100 mg/ml . . . 300 mg/ml, and values and ranges therein). In some embodiments, a bone morphogenetic protein (e.g., BMP4) inhibitor (e.g., Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin, and analogues thereof) is provided in a volume between 75 µl and 7.5 ml (75 µl . . . 100 µl . . . 350 µl . . . 750 µl . . . 1 ml . . . 3.5 ml . . . 7.5 ml, and values and ranges therein) and/or at a concentration of between 2 µg/ml and 200 µg/ml (e.g., 2 µg/ml . . . 5 µg/ml . . . 10 µg/ml . . . 20 µg/ml . . . 50 µg/ml . . . 100 µg/ml . . . 200 µg/ml, and values and ranges therein).

In some embodiments, a kit for performing step (d), as described above, is provided. In some embodiments, a kit is provided that comprises an insulin-like growth factor (e.g., IGFi and/or IGFII), B27, insulin, fibroblast growth factor (e.g., FGF7, bFGF, etc.), exendin-4, nicotinamide, ALK5i II, and forskolin. In some embodiments, an insulin-like growth factor (e.g., IGFi and/or IGFII), B27, insulin, fibroblast growth factor (e.g., FGF7, bFGF, etc.), exendin-4, nicotinamide, ALK5i II, and forskolin are provided in a single container (e.g., tube, vial, etc.). In some embodiments, two or more of an insulin-like growth factor (e.g., IGFi and/or IGFII), B27, insulin, fibroblast growth factor (e.g., FGF7, bFGF, etc.), exendin-4, nicotinamide, ALK5i II, and forskolin are provided in a single container (e.g., tubes, vials, etc.). In some embodiments, two or more of an insulin-like growth factor (e.g., IGFi and/or IGFII, B27, insulin, fibroblast growth factor (e.g., FGF7, bFGF, etc.), exendin-4, nicotinamide, ALK5i II, and forskolin are provided in separate containers (e.g., tubes, vials, etc.). In some embodiments, multiple containers containing separate reagents for performing step (d), as described above, are contained within the same packaging (e.g., box).

In some embodiments, IGFI is provided in a volume between 6 µl and 600 µl (6 µl . . . 10 µl . . . 20 µl . . . 67.5 µl . . . 100 µl . . . 200 µl . . . 600 µl, and values and ranges therein) and/or at a concentration of between 10 µg/ml and 1000 µg/ml+(e.g., 10 µg/ml . . . 20 µg/ml . . . 50 µg/ml . . . 100 µg/ml . . . 200 µg/ml . . . 500 µg/ml . . . 1000 µg/ml, and values and ranges therein). In some embodiments, IGFII is provided in a volume between 36 µl and 3.6 ml (36 µl . . . 50 µl . . . 100 µl . . . 200 µl . . . 1 ml . . . 3.6 ml, and values and ranges therein) and/or at a concentration of between 10 µg/ml and 1000 µg/ml (e.g., 10 µg/ml . . . 20 µg/ml . . . 50 µg/ml . . . 100 µg/ml . . . 200 µg/ml . . . 500 µg/ml . . . 1000 µg/ml, and values and ranges therein). In some embodiments, B27 is provided in a volume between 90 µl and 9 ml (90 µl . . . 200 µl . . . 500 µl . . . 900 µl . . . 2 ml . . . 5 ml . . . 9 ml, and values and ranges therein) and/or at a concentration of between 5× and 500× (e.g., 5× . . . 10× . . . 20× . . . 50× . . . 100× . . . 200× . . . 500×, and values and ranges therein). In some embodiments, fibroblast growth factor (e.g., FGF7, bFGF, etc.) is provided in a volume between 4.5 µl and 4.5 ml (4.5 µl . . . 10 µl . . . 20 µl . . . 45 µl . . . 100 µl . . . 200 µl . . . 450 µl . . . 1 ml . . . 2 ml . . . 4.5 ml, and values and ranges therein) and/or at a concentration of between 10 µg/ml and 1 mg/ml (e.g., 10 µg/ml . . . 20 µg/ml . . . 50 µg/ml . . . 100 µg/ml . . . 200 µg/ml . . . 500 µg/ml . . . 1 mg/ml, and values and ranges therein). In some embodiments, insulin is provided in a volume between 500 µl and 50 ml (500 µl . . . 1 ml . . . 2 ml . . . 5 ml . . . 10 ml . . . 20 ml . . . 50 ml, and values and ranges therein) or between 4.5 µl and 40 µl (e.g., 4.5 µl . . . 10 µl . . . 20 µl . . . 45 µl . . . 100 µl . . . 200 µl . . . 450 µl, or values and ranges therein), and/or at a concentration of between 400 µg/ml and 40 mg/ml (e.g., 400 µg/ml . . . 1 mg/ml . . . 2 mg/ml . . . 4 mg/ml . . . 10 mg/ml . . . 20 mg/ml . . . 40 mg/ml, and values and ranges therein) or between 0.4 µg/ml and 400 µg/ml (e.g., 0.4 µg/ml . . . 10 µg/ml . . . 20 µg/ml . . . 40 µg/ml . . . 100 µg/ml . . . 200 µg/ml . . . 400 µg/ml, or values and ranges therein). In some embodiments, nicotinamide is provided in a volume between 40 µl and 4 ml (40 µl . . . 100 µl . . . 200 µl . . . 400 µl . . . 1 ml . . . 2 ml . . . 4 ml, and values and ranges therein) and/or at a concentration of between 100 mM and 10 M (e.g., 100 mM . . . 200 mM . . . 500 mM . . . 1M . . . 2M . . . 5M . . . 10M, and values and ranges therein). In some embodiments, Exendin-4 is provided in a volume between 1.9 µl and 190 µl (19 µl . . . 50 µl . . . 100 µl . . . 190 µl . . . 500 µl . . . 1 ml . . . 1.9 ml, and values and ranges therein) and/or at a concentration of between 10 µg/ml and 1 mg/ml (e.g., 10 µg/ml . . . 20 µg/ml . . . 50 µg/ml . . . 100 µg/ml . . . 200 µg/ml . . . 500 µg/ml . . . 1 mg/ml, and values and ranges therein). In some embodiments, ALK5i II is provided in a volume between 10 µl and 1 ml (10 µl . . . 20 µl . . . 50 µl . . . 100 µl . . . 200 µl . . . 500 µl . . . 1 ml, and values and ranges therein) and/or at a concentration of between 200 µg/ml and 20 mg/ml (e.g., 200 µg/ml . . . 500 µg/ml . . . 1 mg/ml . . . 2 mg/ml . . . 5 mg/ml . . . 10 mg/ml . . . 20 mg/ml, and values and ranges therein). In some embodiments, forskolin is provided in a volume between 4.5 µl and 4.5 ml (4.5 µl . . . 10 µl . . . 20 µl . . . 45 µl . . . 100 µl . . . 200 µl . . . 450 and values and ranges therein) and/or at a concentration of between 1 mg/ml and 100 mg/ml (e.g., 1 mg/ml . . . 2 mg/ml . . . 5 mg/ml . . . 10 mg/ml . . . 20 mg/ml . . . 50 mg/ml . . . 100 mg/ml, and values and ranges therein).

In some embodiments, a kit for performing step (e), as described above, is provided. In some embodiments, a kit is provided that comprises an insulin-like growth factor (e.g., IGFi), B27, insulin, fibroblast growth factor (e.g., FGF7, bFGF, etc.), exendin-4, nicotinamide, and forskolin. In some embodiments, an insulin-like growth factor (e.g., IGFi), B27, insulin, fibroblast growth factor (e.g., FGF7, bFGF, etc.), exendin-4, nicotinamide, and forskolin are provided in a single container (e.g., tube, vial, etc.). In some embodiments, two or more of an insulin-like growth factor (e.g., IGFi), B27, insulin, fibroblast growth factor (e.g., FGF7, bFGF, etc.), exendin-4, nicotinamide, and forskolin are provided in a single container (e.g., tubes, vials, etc.). In some embodiments, two or more of an insulin-like growth factor (e.g., IGFi), B27, insulin, fibroblast growth factor (e.g., FGF7, bFGF, etc.), exendin-4, nicotinamide, and forskolin are provided in separate containers (e.g., tubes, vials, etc.). In some embodiments, multiple containers containing separate reagents for performing step (e), as described above, are contained within the same packaging (e.g., box). In some embodiments, a kit for performing step (e) may further comprise one or more of IBMX, zinc (ZnSO$_4$), high glucose, glucosamine, thyroid hormone, betatrophin, PUG-NAc, glutathione, N-acetyl-L-cysteine, vitamin C, vitamin E, and/or caerulein (TANAKA, et. Al., Proc Natl Acad Sci USA. 1999 Sep. 14; 96(19):10857-62; herein incorporated by reference in its entirety).

In some embodiments, IGFI is provided in a volume between 6 µl and 600 µl (6 µl . . . 10 µl . . . 20 µl . . . 67.5 µl . . . 100 µl . . . 200 µl . . . 600 and values and ranges therein) and/or at a concentration of between 10 µg/ml and 1000 µg/ml+(e.g., 10 µg/ml . . . 20 µg/ml . . . 50 µg/ml . . . 100 µg/ml . . . 200 µg/ml . . . 500 µg/ml . . . 1000 µg/ml, and values and ranges therein). In some embodiments, B27 is provided in a volume between 90 µl and 9 ml (90 µl . . . 200 µl . . . 500 µl . . . 900 µl . . . 2 ml . . . 5 ml . . . 9 ml, and values and ranges therein) and/or at a concentration of between 5× and 500× (e.g., 5× . . . 10× . . . 20× . . . 50× . . . 100× . . . 200× . . . 500×, and values and ranges therein). In some embodiments, fibroblast growth factor (e.g., FGF7, bFGF, etc.) is provided in a volume between 4.5 µl and 4.5 ml (4.5 µl . . . 10 µl . . . 20 µl . . . 45 µl . . . 100 µl . . . 200 µl . . . 450 µl . . . 1 ml . . . 2 ml . . . 4.5 ml, and values and ranges therein) and/or at a concentration of between 10 µg/ml and 1 mg/ml (e.g., 10 µg/ml . . . 20 µg/ml . . . 50 µg/ml . . . 100 µg/ml . . . 200 µg/ml . . . 500 µg/ml . . . 1 mg/ml, and values and ranges therein). In some embodiments, insulin is provided in a volume between 500 µl and 50 ml (500 µl . . . 1 ml . . . 2 ml . . . 5 ml . . . 10 ml . . . 20 ml . . . 50 ml, and values and ranges therein) or between 4.5 µl and 40 µl (e.g., 4.5 µl . . . 10 µl . . . 20 µl . . . 45 µl . . . 100 µl . . . 200 µl . . . 450 µl, or values and ranges therein), and/or at a concentration of between 400 µg/ml and 40 mg/ml (e.g., 400 µg/ml . . . 1 mg/ml . . . 2 mg/ml . . . 4 mg/ml . . . 10 mg/ml . . . 20 mg/ml . . . 40 mg/ml, and values and ranges therein) or between 0.4 µg/ml and 400 µg/ml (e.g., 0.4 µg/ml . . . 10 µg/ml . . . 20 µg/ml . . . 40 µg/ml . . . 100 µg/ml . . . 200 µg/ml . . . 400 µg/ml, or values and ranges therein). In some embodiments, nicotinamide is provided in a volume between 40 µl and 4 ml (40 µl . . . 100 µl . . . 200 µl . . . 400 µl . . . 1 ml . . . 2 ml . . . 4 ml, and values and ranges therein) and/or at a concentration of between 100 mM and 10 M (e.g., 100 mM . . . 200 mM . . . 500 mM . . . 1M . . . 2M . . . 5M . . . 10M, and values and ranges therein). In some embodiments, Exendin-4 is provided in a volume between 1.9 µl and 190 µl (19 µl . . . 50 µl . . . 100 µl . . . 190 µl . . . 500 µl . . . 1 ml . . . 1.9 ml, and values and ranges therein) and/or at a concentration of between 10 µg/ml and 1 mg/ml (e.g., 10 µg/ml . . . 20 µg/ml . . . 50 µg/ml . . . 100 µg/ml . . . 200 µg/ml . . . 500 µg/ml . . . 1 mg/ml, and values and ranges therein). In some embodiments, forskolin is provided in a volume between 4.5 µl and 4.5 ml (4.5 µl . . . 10 µl . . . 20 µl . . . 45 µl . . . 100 µl . . . 200 µl . . . 450 µl, and values and ranges therein) and/or at a concentration of between 1 mg/ml and 100 mg/ml (e.g., 1 mg/ml . . . 2 mg/ml . . . 5 mg/ml . . . 10 mg/ml . . . 20 mg/ml . . . 50 mg/ml . . . 100 mg/ml, and values and ranges therein).

Kits may comprise solutions in water, DMSO, buffer, media, etc. Kits may also comprise dry reagents. In some embodiments, reagents in kits are reconstituted, dissolved, or diluted prior to use.

Kits may also comprise controls (e.g., control cells, control reagent (e.g., negative control buffers), etc.), cells, buffers, salts, tubes, plates (e.g, 12-well, 24 well, 96-well, 384 well, etc.), Transwell plates, cluster-forming vessels, solid supports (e.g., for cell culture), instructions, etc.

In some embodiments, the kits and/or kit components described herein are used to culture stem cells. In some embodiments, the kits and/or kit components described herein are used to generate pancreatic lineage cells (e.g., populations comprising one or more of beta-like cells, insulin-secreting cells, glucose-responsive cells, etc.) In some embodiments, kits comprise reagents and/or components for testing nature, properties, and/or quality of differentiated cells (e.g., pancreatic lineage cells generated by the methods described herein (e.g., beta-like cells or a cell population comprising beta-like cells)). For example, reagents for testing biomarkers (e.g., pdx1 (or the protein encoded thereby), nkx6.1 (or the protein encoded thereby), glucagon, and insulin) of pancreatic lineage cells may be provided. Suitable testing reagents may include antibodies, primers, probes, etc. Testing reagents may also include those suitable for testing glucose response of cells.

In some embodiments, compositions are provided comprising cells (e.g., pluripotent stem cells, pancreatic lineage cells (e.g., beta-like cells or a cell population comprising beta-like cells), intermediate differentiated cells, etc.) and one or more of the reagents described herein (e.g., all of the reagents of one step (e.g., (a)-(d) of the methods described herein.

In some embodiments, methods and/or cells are provided for testing an agent for its effect(s) on pancreatic lineage cells (e.g., beta-like cells or a cell population comprising beta-like cells) such as by exposing a cell generated by methods provided herein with said agent and assaying for the effect on said cell.

In some embodiments, methods are provided for testing a library of compounds comprising for effect on pancreatic β-like cells comprising: (a) receiving a plurality of reaction vessels, each vessel containing the cells generated by methods provided herein; (b) exposing each of the plurality of reaction vessels to a compound from the library of compounds; and (c) detecting the effect of the compounds on the pancreatic β-like cells. In some embodiments, the plurality of reaction vessels are in one or more multiwell plates. In some embodiments, the testing comprises high throughput screening. In some embodiments, the high throughput screening is automated.

In some embodiments, provided herein are methods of testing a library of compounds comprising for effect on pancreatic β-like cells comprising: (a) placing pluripotent stem cells in a plurality of reaction vessels; (b) generating pancreatic lineage cells by the methods described herein; (c) exposing the pancreatic lineage cells in each of the plurality of reaction vessels to a compound from the library of compounds; and (d) detecting the effect of the compounds on the pancreatic lineage cells. In some embodiments, the plurality of reaction vessels are in one or more multiwell plates. In some embodiments, the testing comprises high throughput screening. In some embodiments, the high throughput screening is automated.

In some embodiments, provided herein are compositions comprising microencapsulated cells generated by the methods herein. In some embodiments, the cells are microencapsulated in alginate hydrogel or another suitable polymer. In some embodiments, compositions further comprise an immune modulating agent. In some embodiments, the immune modulating agent is a T-cell chemorepellent and/or a pro-survival factor. In some embodiments, the cells are present as an islet-like cell cluster. In some embodiments, provided herein are methods of treating a subject, comprising implanting a composition of one of microencapsulated cells into the subject.

In some embodiments, provided herein are method of shipping (e.g., live cell transport) pancreatic lineage cells (e.g., beta-like cells or a cell population comprising beta-like cells) comprising: (a) removing an upper compartment of a Transwell plate from the Transwell plate, wherein the upper compartment contains the pancreatic lineage cells (e.g., cells are on (e.g., adhered to) the upper surface of the membrane (or filter) that forms the bottom of the upper compartment); (b) placing the upper compartment in a shipping media comprising a serum-free medium, an insulin-like growth factor, fibroblast growth factor, insulin, nicotinamide, exendin-4 and/or GLP-1, and an agent that increase cAMP, wherein the cells are exposed to the media; and (c) shipping the cells in the media, while maintaining the cells at room temperature. In some embodiments, methods further comprise the step of removing bubbles from the media. In some embodiments, the shipping occurs in under 48 hours. In some embodiments, the cells are produced by methods described herein (e.g., generated from pluripotent stem cells). In some embodiments, post-shipment cells have >90% of pre-shipment viability (>90%, >95%, >98%, >99%, >99.8%, >99.9%). In some embodiments, shipping methods apply to pluripotent stem cells (e.g., iPSC, ESC, etc.), pancreatic lineage cells (e.g., beta-like cells) generated with methods herein, islet-like clusters, and any intermediate cells types generated during methods described herein. In some embodiments, a single well (e.g., Transwell upper compartment) is shipped. In other embodiments, all the upper compartments (e.g., 12 wells, 24 wells, 96 wells, etc.) of a Transwell plate are shipped.

In some embodiments, provided herein are islet-like clusters comprising cells generated by methods described herein. In some embodiments, cells produced by methods described herein are transferred (e.g., from a transwell plate) to a device for the production of ell aggregates (e.g., U.S. Pub. No. 2011/0086375; U.S. Pub. No. 2010/0068793; U.S. Pub. No. 2012/0149051; herein incorporated by reference in their entireties). For example, such an aggregation device may comprise a microwell device with a high density of microwells with limited spacing between the microwells. The high density forces cells into the wells and not outside on the plate. Such a device is characterized by wells having at least one non-vertical sidewall, preferably all of the sidewalls are non-vertical and have a substantially constant slope that converge to a point, such that for a microwell of given dimensions, any number of cells from two up to the volumetric capacity of the microwell will, when deposited in the microwell (e.g., via gravity or centrifugation), be forced into contact with one another. Therefore, in some embodiments, an aggregation device (e.g., AggreWell) is designed such that a broad continuum of aggregate sizes can be generated from microwells of a single size, with the aggregate size depending only on the number of cells deposited into each microwell. In some embodiments, the aggregation device comprises: (a) a body comprising an upper region defining an upper plane; (b) a plurality of wells extending downwardly from the upper plane into the body; (c) each of the wells comprising an axis extending perpendicularly to the upper plane; and (d) each of the wells comprising a sidewall, the sidewall of at least one of the wells having at least one wall component extending inwardly towards the axis. In some embodiments, at least one wall component is at an angle of less than 90° with respect to the upper plane, more preferably the angle is between 20° and 80°, most preferably between 50° and 60°.

In some embodiments, islet-like clusters are placed into suspension (e.g., for storage, for shipping, for expansion, etc.). In some embodiments, islet-like clusters are transferred from an aggregation device to an appropriate dynamic culture system, such as a disposable plastic, reusable plastic, stainless steel or glass vessel (e.g., a spinner flask or an Erlenmeyer flask). In some embodiments, islet-like clusters are further cultured in such a system. In some embodiments, islet-like clusters are shipped in such a system.

In some embodiments, provided herein are methods of characterizing pancreas lineage cells (e.g., beta-like cells or a cell population comprising beta-like cells) generated from pluripotent stem cells comprising transplanting the cells into an organism. In some embodiments, the pancreas lineage cells are present in an islet-like cluster (e.g., formed via an aggregation device (e.g., U.S. Pub. No. 2011/0086375; U.S. Pub. No. 2010/0068793; U.S. Pub. No. 2012/0149051; herein incorporated by reference in their entireties)). In some embodiments, the pancreatic lineage cells are monohormonal, glucose-responsive, insulin-secreting, pdx1-expressing, etc. In some embodiments, the pancreas lineage cells are encapsulated.

BRIEF DESCRIPTION OF THE DRAWINGS

FIG. 35 shows the percentage of cells differentiated using the methods described herein. are insulin+/PDX1+ or insulin+/NKX6.1+.

DEFINITIONS

Figure 1:
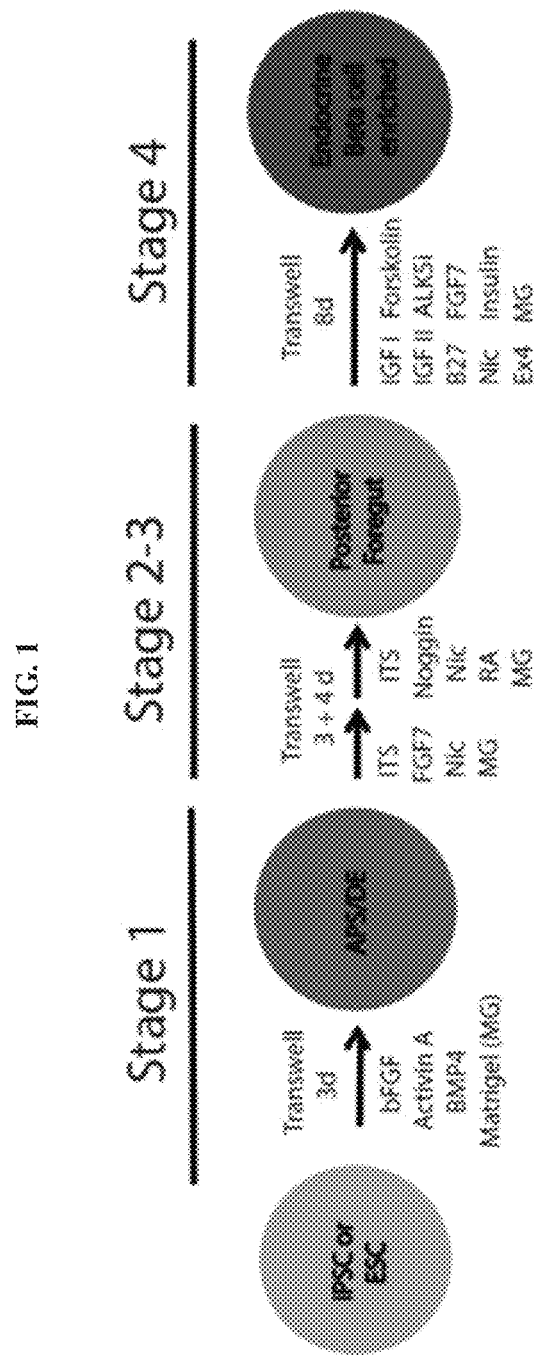
FIG. 1 shows an exemplary (ProgenMix III) pancreatic lineage differentiation protocol. A four stage protocol for culturing human ESCs or iPSCs on Transwell membranes for 18 days without manipulation using mediation formulation as described. Abbreviations: APS=anterior primitive streak, DE=definitive endoderm, Ex4=Exendin4, Nic=Nicotinamide, ITS=insulin-transferrin-selenium, RA=all-trans-retinoic acid. Stage 5 culture maintains the phenotype for an additional 7 days in the stage 4 media without IGF II and ALK5i.
Figure 2:
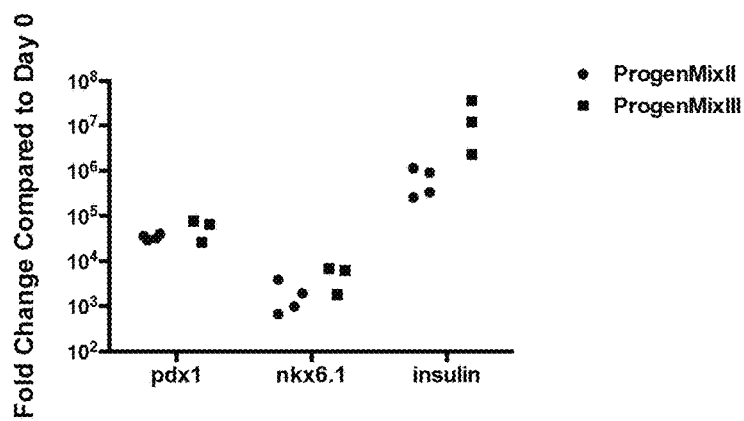
FIG. 2 shows a graph comparing expression of pdx1 nkx6.1, and insulin using an exemplary (ProgenMix III) pancreatic lineage differentiation protocol versus a previous protocol.
Figure 3:
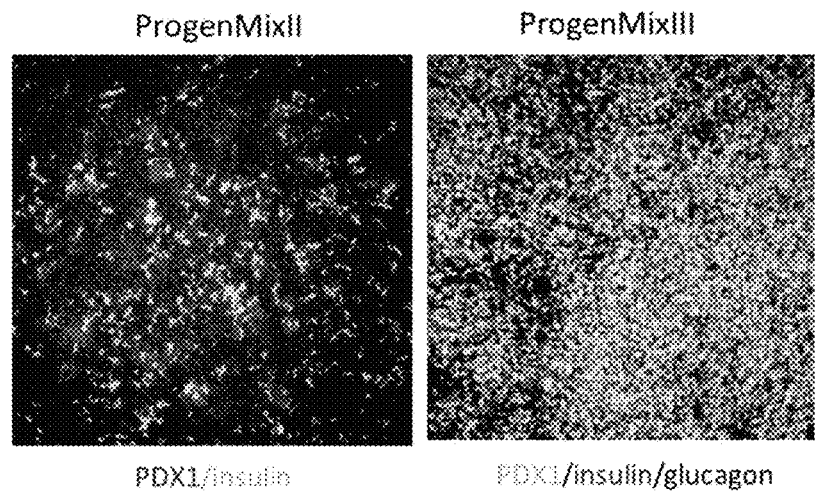
FIG. 3 shows in image demonstrating increased insulin expression with an exemplary (ProgenMix III) pancreatic lineage differentiation protocol versus a previous protocol.
Figure 4:
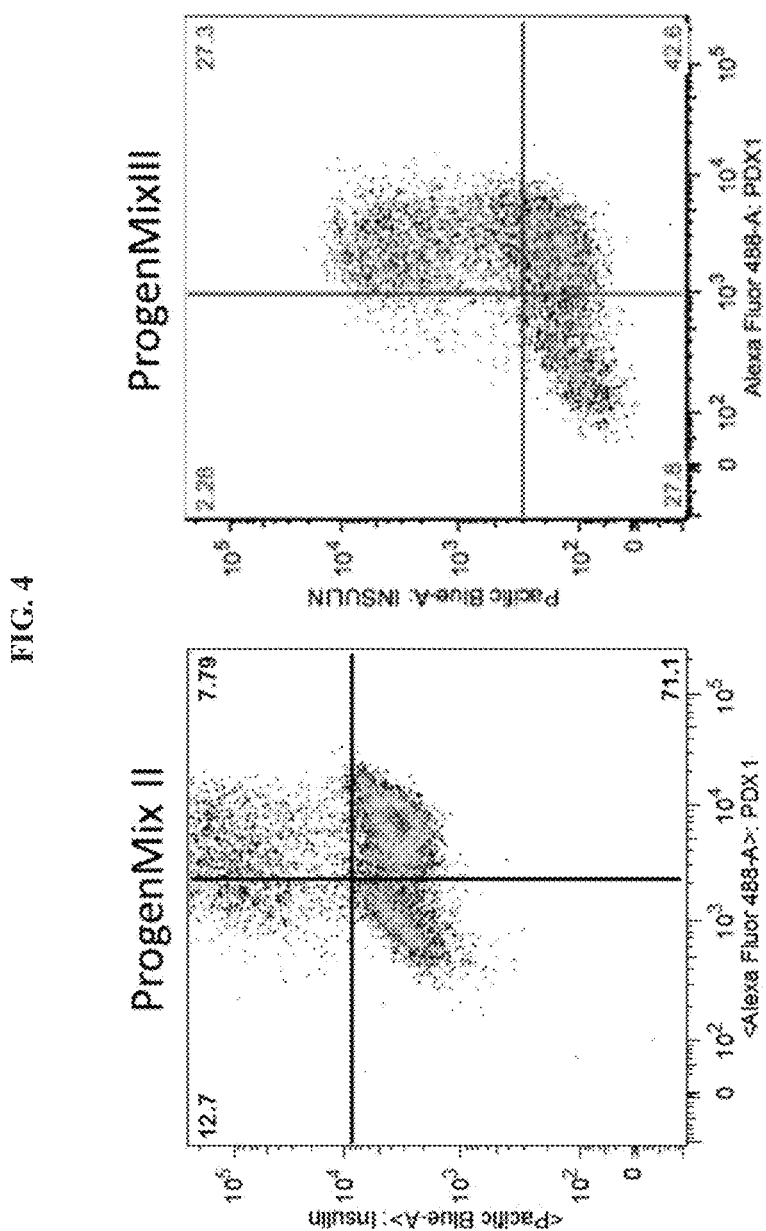
FIG. 4 shows in image demonstrating increased PDX1/insulin co-staining with an exemplary (ProgenMix III) pancreatic lineage differentiation protocol versus a previous protocol.

As used herein the term "stem cell" ("SC") refers to cells that can self-renew and differentiate into multiple lineages. A stem cell is a developmentally pluripotent or multipotent cell. A stem cell can divide to produce two daughter stem cells, or one daughter stem cell and one progenitor ("transit") cell, which then proliferates into the tissue's mature, fully formed cells. Stem cells may be derived, for example, from embryonic sources ("embryonic stem cells") or derived from adult sources. For example, U.S. Pat. No. 5,843,780 to Thompson describes the production of stem cell lines from human embryos. PCT publications WO 00/52145 and WO 01/00650 describe the use of cells from adult humans in a nuclear transfer procedure to produce stem cell lines.

Examples of adult stem cells include, but are not limited to, hematopoietic stem cells, neural stem cells, mesenchymal stem cells, and bone marrow stromal cells. These stem cells have demonstrated the ability to differentiate into a variety of cell types including adipocytes, chondrocytes, osteocytes, myocytes, bone marrow stromal cells, and thymic stroma (mesenchymal stem cells); hepatocytes, vascular cells, and muscle cells (hematopoietic stem cells); myocytes, hepatocytes, and glial cells (bone marrow stromal cells) and, indeed, cells from all three germ layers (adult neural stem cells).

As used herein, the term "totipotent cell" refers to a cell that is able to form a complete embryo (e.g., a blastocyst).

As used herein, the term "pluripotent cell" or "pluripotent stem cell" refers to a cell that has complete differentiation versatility, e.g., the capacity to grow into any of the mammalian body's approximately 260 cell types. A pluripotent cell can be self-renewing, and can remain dormant or quiescent within a tissue. Unlike a totipotent cell (e.g., a fertilized, diploid egg cell), a pluripotent cell, even a pluripotent embryonic stem cell, cannot usually form a new blastocyst.

As used herein, the term "induced pluripotent stem cells" ("iPSCs") refers to a stem cell induced from a somatic cell, e.g., a differentiated somatic cell, and that has a higher potency than said somatic cell. iPS cells are capable of self-renewal and differentiation into mature cells.

As used herein, the term "multipotent cell" refers to a cell that has the capacity to grow into a subset of the mammalian body's approximately 260 cell types. Unlike a pluripotent cell, a multipotent cell does not have the capacity to form all of the cell types.

As used herein, the term "progenitor cell" refers to a cell that is committed to differentiate into a specific type of cell or to form a specific type of tissue.

As used herein, the term "embryonic stem cell" ("ES cell" or ESC") refers to a pluripotent cell that is derived from the inner cell mass of a blastocyst (e.g., a 4- to 5-day-old human embryo), and has the ability to yield many or all of the cell types present in a mature animal.

As used herein the term "feeder cells" refers to cells used as a growth support in some tissue culture systems. Feeder cells may be embryonic striatum cells or stromal cells.

As used herein, the term "chemically defined media" refers to culture media of known or essentially-known chemical composition, both quantitatively and qualitatively. Chemically defined media is free of all animal products, including serum or serum-derived components (e.g., albumin).

As used herein, the term "serum-free media" refers to culture media that is devoid of serum, but not necessarily of other undefined components.

As used herein, the terms "pancreatic lineage cells" or "cells of the pancreatic lineage" refer to any endocrine (e.g., alpha cells, beta cells, delta cells, PP cells, epsilon cells, etc.) or exocrine cells that comprise the pancreas, or the precursor cells (e.g., progenitor cells, intermediate development cells, etc.) that are committed to a pancreatic cell lineage.

As used herein, the terms "pancreatic beta cells," "islet beta cells," or "beta cells" refer to monohormonal, pancreatic lineage, endocrine cells located in the islets of Langerhans of the pancreas. Beta cells are capable of secreting insulin in response to elevated glucose concentrations (e.g., glucose-responsive) and express markers, including, but not limited to, insulin and pdx1.

As used herein, the terms "beta-like cells" or "induced beta cells" refer to cells generated from pluripotent stem cells by human manipulation that exhibit characteristics of beta cells, including, but not limited to, glucose responsiveness, insulin secretion, monohormonal, and/or expressing beta cell markers (e.g., insulin, pdx1). In some embodiments, beta-like cells are characterized based on their similarity, in terms of a particular characteristic (e.g., those described herein) to primary beta cells (e.g., isolated from a human pancreas).

DETAILED DESCRIPTION

Methods, kits, compositions, and systems are provided for culturing pluripotent stem cells to produce populations of cells comprising beta-like cells (e.g., pancreatic lineage, glucose-responsive, and/or insulin-producing). In particular, culture conditions are provided that result in the generation of beta-like cells from a starting culture of human pluripotent stem cells.

The pancreatic cell lineage forms from the embryonic foregut and is of endodermal origin. In nature, pancreatic development begins the formation of a ventral and dorsal buds. Each structure communicates with the foregut through a duct. The dorsal pancreatic bud forms the head, body and tail, whereas the ventral pancreatic bud forms the uncinate process. Differential rotation and fusion of the ventral and dorsal pancreatic buds results in the formation of the definitive pancreas. As the duodenum rotates to the right, it carries with it the ventral pancreatic bud and common bile duct. Upon reaching its final destination, the ventral pancreatic bud fuses with the much larger dorsal pancreatic bud. At this point of fusion, the main ducts of the ventral and dorsal pancreatic buds fuse, forming the main pancreatic duct. The duct of the dorsal bud regresses, leaving the main pancreatic duct. Differentiation of cells of the pancreas proceeds through two different pathways, corresponding to the dual endocrine and exocrine functions of the pancreas. In progenitor cells of the exocrine pancreas, important molecules that induce differentiation include follistatin, fibroblast growth factors, and activation of the Notch receptor system. Development of the exocrine acini progresses through three successive stages. These include the predifferentiated, protodifferentiated, and differentiated stages, which correspond to undetectable, low, and high levels of digestive enzyme activity, respectively. Progenitor cells of the endocrine pancreas arise from cells of the protodifferentiated stage of the exocrine pancreas. Under the influence of neurogenin-3 and Isl-1, but in the absence of notch receptor signaling, these cells differentiate to form committed endocrine precursor cells. Influenced by Pax-6, beta cells (β-) and delta cells (δ-) which secrete insulin and somatostatin, respectively, are produced.

In some embodiments, provided herein are systems, kits, and methods for the generation of pancreatic lineage cells (e.g., beta-like cells or a cell population comprising beta-like cells) from stem cells. Methods are provided for directed in vitro differentiation of pluripotent stem cells. For example, pluripotent stem cells may be directed to differentiate into cells of the pancreatic lineage. In some embodiments, the methods involve culturing the stem cells in the presence of an effective amount of the appropriate factors/reagents (e.g., fibroblast growth factor (e.g., bFGF, etc.), Activin A, and bone morphogenetic protein (e.g., BMP4) to induce differentiation, resulting in primitive streak and definitive endodermal cells. In some embodiments, these cells are subsequently cultured in the presence of an effective amount of the appropriate factors/reagents (e.g., ITS, FGF7, nicotinamide, etc.; ITS, Noggin, nicotinamide, retinoic acid, etc.) to result in the formation of progenitor foregut cells. In some embodiments, these progenitor foregut cells are further cultured in the presence of an effective amount of the appropriate factors/reagents (e.g., IGF I, IGF II, B27, nicotinamide, exendin-4, forskolin, Alk5i II, insulin, etc.) to result in the formation of pancreatic lineage endocrine cells (e.g., β cells). By utilizing defined medium components that promote pancreatic cell differentiation, the described methods provide a simple, reproducible approach to enable large-scale production of pancreatic cell types (e.g., β cells) for research, diagnostic, and/or therapeutic uses. In some embodiments, one or more culture steps are performed on Matrigel or the like.

Differentiation Factors

Various growth factors and other chemical signals may initiate differentiation of hESCs or hiPSs into progeny cell cultures of one or more particular lineage (e.g., beta-like cells or a cell population comprising beta-like cells).

One of these differentiation factors is known as bone morphogenetic protein (BMP). BMPs are members of the transforming growth factor-β (TGFβ) superfamily of secreted signaling molecules, which play extensive pleiomorphic roles in almost all aspects of embryonic development. BMP4 and other BMP family members, such as BMP2, BMP5, and BMP7, bind BMP type II receptor BRII, which recruits type I receptor BR1A (ALK3) or BR1B (ALK6). Upon ligand activation, the intracellular kinase domain of the type I receptors phosphorylates Smad1, -5, and -8, which are then escorted by a common Smad4 to enter the nucleus and activate target genes. The relative expression level of BMPs, receptors, and Smads within the cell is an important determinant of BMP-induced responses. BMP signaling, and disruption thereof by BMP inhibitors, affects the body plan of developing embryos. For example, along with activin, BMP4 synergistically promote formation of definitive endoderm in human embryonic stem cells. Subsequently, blocking of BMP4 action by BMP4 inhibitors favors pancreatic lineage differentiation over, for example liver induction. Known BMP4 inhibitors include Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin.

Fibroblast growth factor (FGF) also plays a role in mesoderm formation. There are several different FGF subfamilies, the member ligands of which include FGF1-FGF23. Of the known FGF ligands, all show some degree of overlap of receptor binding, with the exception of FGF11-FGF14. (FGF Signaling in Vertebrate Development. Pownall M E, Isaacs H V. San Rafael (Calif.): Morgan & Claypool Life Sciences; 2010; herein incorporated by reference in its entirety).

Transforming growth factor beta (TGF-β) is a protein that controls proliferation, cellular differentiation, and other functions in most cells. TGF-β is part of a superfamily of proteins known as the transforming growth factor beta superfamily, which includes inhibins, anti-müllerian hormone, activin, bone morphogenetic protein, decapentaplegic and Vg-1 and TGF-β. The TGF-β signaling pathway is involved in many cellular processes in both adult organisms and the developing embryos, including cell growth, cell differentiation, apoptosis, cellular homeostasis and other cellular functions. In the TGFβ signaling pathway, a TGFβ superfamily ligand binds to a type II receptor, which recruits and phosphorylates a type I receptor. The type I receptor then phosphorylates receptor-regulated SMADs (R-SMADs) which binds a coSMAD. R-SMAD/coSMAD complexes then accumulate in the nucleus where they act as transcription factors and participate in the regulation of target gene expression. The cellular effect of TGF-β and other TGF-β superfamily members is regulated by inhibitors. Known TGF-β inhibitors include ALK5i, ALK5i II, GW-6004, A 83-01, D 4476, GW 788388, LY 365947, RepSox, SB 431542, SB 525334, SD 208, etc. (See, e.g., Tocris Bioscience).

Activin is a member of the TGF-β superfamily and has various effects on diverse biological systems (Abe Y, et al. Growth Factors 2004 June; 22(2):105-10; herein incorporated by reference in its entirety). Activin A has been reported to have a role in the induction of definitive endoderm from hESCs (D'Amour, K. A., et al. (2005); herein incorporated by reference in its entirety). However, results testing Activin A (at 5 ng/ml, 50 ng/ml, or 100 ng/ml) in serum-free medium indicate that this treatment alone cannot induce pancreatic cell differentiation.

Adenyl cyclase catalyzes the conversion of ATP to 3',5'-cyclic AMP (cAMP) and pyrpphosphate. Experiments have indicated that increased cAMP levels play a role in regulation of pancreatic beta-cell growth and differentiation (Leech et al. Biochem Biophys Res Commun. 2000 Nov. 11; 278(1):44-7; herein incorporated by reference in its entirety). Agonists of the adenyl cyclase system are agents that result in increased levels of cAMP, by directly acting upon adenyl cyclase (e.g., forskolin or other adenyl cyclase agonists), or by acting upstream of adenyl cyclase (e.g., glucagon binding to the glucogon receptor results in a conformational change in the receptor, activation of G-proteins, and the subsequent activation of adenyl cyclase).

A phosphodiesterase (PDE) is any enzyme that breaks a phosphodiester bond; specifically a cyclic nucleotide phosphodiesterase is an enzyme that degrades the phosphodiester bond in the second messenger molecules cAMP and cGMP. Inhibiters of cyclic nucleotide phosphodiesterases prevent degradation of cAMP and/or cGMP, thereby increasing the concentration of cAMP and/or cGMP in a system or solution or prolonging the effect of cAMP and/or cGMP. For example, methylated xanthenes (e.g., caffeine, aminophylline, IBMX, paraxanthine, pentoxifylline, theobromine, theophylline, etc.) inhibit cyclic nucleotide phosphodiesterases that degrade cAMP and/or cGMP, thereby increasing intracellular cAMP and/or cGMP concentration and activating cAMP- and/or cGMP dependent enzymes and pathways.

Experiments conducted during development of embodiments of the present invention have identified additional factors and reagents useful for the differentiation of human pluripotent stem cells into cells of the pancreatic cell lineage (e.g., β-like cells). See protocols described herein, for examples.

Chemically Defined Media

A concern in the culture of human ES cells is to remove, to the extent possible, undefined constituents and constituents of animal origin from ES cell culture conditions. Standardizing culture conditions minimizes the normal variations in biological materials to which the cells are exposed. Further, by avoiding the use of materials, cells, exudates or constituents of animal origin, one can avoid possible cross-species viral transmission through the culture system. Thus, utilization of chemically defined media (CDM) that avoid the use of animal products provides a baseline culture condition upon which differentiation factors may be added with predictable effects.

CDM (e.g., for hESCs) may include a basal medium containing salts, vitamins, glucose and amino acids. The basal medium can be any of a number of commercially available media. For example, a combination of Dulbecco's Modified Eagle Medium and Hams F12 medium, sold as a combination (DMEM/F12; Invitrogen) may be utilized. To that combination may be added glutamine, β-mercaptoethanol, and non-essential amino acids. Other possible additives include antioxidants such as glutathione, N-acetyl-L-cysteine, vitamin C, vitamin E and lipids (TANAKA, et. Al., Proc Natl Acad Sci USA. 1999 Sep. 14; 96(19):10857-62; herein incorporated by reference in its entirety). A protein constituent of the medium is a serum substitute product. Albumin or purified albumin products, like the commercial product ALBUMAX (Invitrogen) may be used. Alternatively or in addition, a defined protein product made up of albumin, insulin and transferrin may be used. Human proteins are preferred but not essential so long as uncharacterized animal products are excluded.

FAB medium, for example, includes FGF, Activin A, and BMP in DMEM/F12 supplemented with 2% BSA (or alternatively HSA), 1 mM L-glutamine, 1% nonessential amino acids, and 0.1 mM 2-mercaptoethanol. Effective amounts of BMP, for example, BMP4, may range from about 1-50 ng/ml, or from about 10 ng/ml to about 50 ng/ml, or about 20 ng/ml to about 80 ng/ml, or about 15 ng/ml or about 25 ng/ml, or about 50 ng/ml, or about 75 ng/ml, or about 100 ng/ml. Effective amounts of FGF, for example, bFGF, may range from about 10 ng/ml to about 200 ng/ml, or from about 10 ng/ml to about 100 ng/ml, or about 20 ng/ml to about 80 ng/ml, or about 15 ng/ml, or about 25 ng/ml, or about 50 ng/ml, or about 75 ng/ml, or about 100 ng/ml, or about 120 ng/ml, or about 140 ng/ml or about 160 ng/ml, or about 180 ng/ml or about 200 ng/ml. Further, effective amounts of Activin A may range from about 10 ng/ml to about 200 ng/ml, or from about 10 ng/ml to about 100 ng/ml, or about 20 ng/ml to about 80 ng/ml, or about 15 ng/ml, or about 25 ng/ml, or about 50 ng/ml, or about 75 ng/ml, or about 100 ng/ml, or about 120 ng/ml, or about 140 ng/ml or about 160 ng/ml, or about 180 ng/ml or about 200 ng/ml. In one embodiment, FAB medium contains 11 ng/ml bFGF, 100 ng Activin A, and 50 ng BMP4.

ITS medium may include about 5 μg/ml insulin, about 5 μg/ml transferrin, about 5 ng/ml selenous acid, and about 20 to about 100 ng/ml bFGF.

ITSFINE media may include about 5 μg/ml insulin, about 5 μg/ml transferrin, about 5 ng/ml selenous acid (selenium), about 10 ng/ml to about 100 ng/ml FGF7 (R&D), about 50 nM to about 500 nM INGAP (PSN-4765), about 10 mM nicotinamide (Sigma), about 1 nM to about 100 nM exendin-4 (Sigma), about 4 μg/ml to about 15 μg/ml insulin (Gibco), and about 2 g/L BSA (Sigma).

I'IIBEFINE media may include about 150 ng/ml IGF I, about 800 ng/ml IGF II, B27 (50× dilution), about 4 ng/ml insulin, about 10 ng/ml FGF7, about 10 nM exendin-4, and about 10 mM nicotinamide. In some embodiments, 10 uM forskolin and 1 uM ALK5i are included with I'IIBEFINE media.

Extracellular Matrix Components

Growth-factor depleted Matrigel (BD) may be used in the present disclosure as one example of an extracellular matrix that may help cells form three dimensional structures to promote cell-cell contact and create a more islet-like environment. Other extracellular matrix components that form an extracellular matrix gel may be used, including combinations of extracellular matrix components, gelling agents, proteins, and optionally growth factors. For example, combinations of laminins (for example, laminin-411 and laminin-511), collagen IV, entactin, and other polymeric materials may be used. Further, extracellular matrices contemplated may include growth factors such as bFGF, epidermal growth factor, insulin-like growth factor 1, platelet derived growth factor, nerve growth factor, and TGF-β.

Culture Conditions

Provided herein are multistep cell culture procedures for differentiating stem cells into cell populations comprising pancreatic beta-like cells. In some embodiments, cells are placed in a series of culture conditions (e.g., Stages 1-5), for proscribed time periods. In some embodiments, culture media is changed regularly (e.g., hourly, four-times daily, twice daily, daily, etc.). In some embodiments, culture media is continuously replenished. In some embodiments, cell culture is carried out at room temperature (e.g., 18° C., 19° C., 20° C., 21° C., 22° C., 23° C., 24° C., or ranges therein). In some embodiments, reagents used in culture media are sterilized. In some embodiments, devices (e.g., chambers, vessels, bottles, flasks, tubes, etc.) used in culturing are sterilized.

In some embodiments, appropriate devices are selected for containing cells and media during the various stages of culturing (e.g., Transwell) and/or post-culturing shipping (e.g., conical tube, etc.), clustering (etc., AggreWell), expansion (e.g., Spinner flask, etc.), etc. One commercially available device that finds use in some embodiments described herein are Transwell cell culture chambers, or Transwell plates (e.g., available from Costar Corp., Cambridge, Md., USA). Each chamber of a Transwell plate comprises a flat-bottomed, open-topped, lower compartment with impermeable bottom and sides, and an open-topped, upper compartment with a microporous membrane which forms the bottom of the upper compartment. This assembly is typically covered by a removable lid. In use, cells are placed on the upper surface of the microporous membrane within the upper compartment. The upper compartment is inserted into the lower compartment. Due to the permeability of the membrane, media, nutrients, factors, etc. are able to traverse the membrane.

Exemplary components of the multistage culture mediums are described in the experimental section below. In some embodiments, differentiation comprises the steps of: (a) culturing the stem cells in a chemically defined medium, fibroblast growth factor, Activin A, and bone morphogenetic protein; (b) culturing the cells from step (a) in the presence of chemically defined medium comprising insulin, transferrin, and selenium, a fibroblast growth factor and nicotinamide; (c) culturing the cells from step (b) in the presence of a chemically defined medium comprising insulin, transferrin, and selenium; retinoic acid; a bone morphogenetic protein inhibitor; and nicotinamide; and (d) culturing the cells from step (c) in the presence of a serum-free medium, an insulin-like growth factor, insulin, nicotinamide, exendin-4 and/or GLP-1, a TGF-beta inhibitor, and an agent that increase cAMP; and optionally (e) maintaining the cells of the pancreatic lineage for 1-50 days by culturing the cells from step (d) in the presence of a serum-free medium, an insulin-like growth factor, fibroblast growth factor, insulin, nicotinamide, exendin-4 and/or GLP-1, and an agent that increase cAMP.

In some embodiments, differentiation comprises the steps of (a) culturing the stem cells for 2-4 days in a chemically defined medium, basic fibroblast growth factor, Activin A, BMP4, LY294002, and Matrigel; (b) culturing the cells from step (a) for 2-4 days in the presence of chemically defined ITS medium, FGF7, nicotinamide, and Matrigel; (c) culturing the cells from step (b) for 3-5 days in the presence of a chemically defined ITS medium, retinoic acid, Noggin, nicotinamide, and Matrigel; (d) culturing the cells from step (c) for 6-10 days in the presence of a B27 serum-free medium, IGF I, IGF II, FGF7, insulin, Noggin, nicotinamide, exendin-4, ALK5i II, forskolin, and Matrigel; and (e) maintaining the cells of the pancreatic lineage for 1-50 days by culturing the cells from step (d) in the presence of a serum-free medium, ALK5, Forskolin, ZnSO4, T3, B27, heparin, and antioxidant, and a P13 kinase inhibitor. In some embodiments, step (c) is performed in two steps (e.g., a first step of culturing in the presence of chemically defined ITS medium; retinoic acid; and Noggin for 2 days and then a second step of culturing in the presence of chemically defined ITS medium, EGF, and FGF7 for two days). In some embodiments, step (d) further comprises EGF. In some embodiments, step (e) further comprises the addition of Warfarin.

In some embodiments, differentiation comprises the steps of: (a) culturing the stem cells for 2-4 days in a chemically defined medium, basic fibroblast growth factor, Activin A, BMP4, LY294002, and Matrigel; (b) culturing the cells from step (a) for 2-4 days in the presence of chemically defined ITS medium, FGF7, nicotinamide, and Matrigel; (c) culturing the cells from step (b) for 2 days in the presence of a chemically defined ITS medium, retinoic acid, Noggin, nicotinamide, and Matrigel; (d) culturing the cell of step (c) for 2 days in the presence of chemically defined ITS medium, EGF, and FGF7; (e) culturing the cells from step (d) for 6-10 days in the presence of a B27 serum-free medium, IGF I, IGF II, FGF7, insulin, Noggin, nicotinamide, exendin-4, ALK5i II, forskolin, and Matrigel; and (f) maintaining the cells of the pancreatic lineage for 1-50 days by culturing the cells from step (e) in a suspension culture in the presence of a serum-free medium, ALK5, Forskolin, ZnSO4, T3, B27, heparin, an antioxidant, Warfarin, and a P13 kinase inhibitor.

Transplantation

Provided herein are methods and systems for treating a patient suffering from, or at risk of developing, a conditions or disease (e.g., Type 1 diabetes, Type 2 diabetes, etc.). In certain embodiments, the method involves culturing pluripotent stem cells, differentiating the pluripotent stem cells in vitro into a beta-like cell lineage, and implanting the beta-like cells into the patient.

If appropriate, cells are co-administered with one or more pharmaceutical agents or bioactives that facilitate the survival and function of the transplanted cells. These agents may include, for example, insulin, members of the TGF-.beta. family, including TGF-.beta.1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -7, -8, -10, -15), vascular endothelial cell-derived growth factor (VEGF), pleiotrophin, endothelin, among others. Other pharmaceutical compounds can include, for example, nicotinamide, glucagon like peptide-I (GLP-I) and II, GLP-1 and GLP-2 mimetibody, Exendin-4, retinoic acid, parathyroid hormone, MAPK inhibitors, etc.

Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, for example, the materials disclosed in U.S. Pat. Nos. 5,770,417, 6,022,743, 5,567,612, 5,759,830, 6,626,950, 6,534,084, 6,306,424, 6,365,149, 6,599,323, 6,656,488, U.S. Published Application 2004/0062753 A1, U.S. Pat. Nos. 4,557,264 and 6,333,029.

Cells generated with methods and reagents herein may be implanted as dispersed cells or formed into implantable clusters. In some embodiments, cells are provided in biocompatible degradable polymeric supports; porous, permeable, or semi-permeable non-degradable devices; or encapsulated (e.g., to protect implanted cells from host immune response, etc.). Cells may be implanted into an appropriate site in a recipient. Suitable implantation sites may include, for example, the liver, natural pancreas, renal subcapsular space, omentum, peritoneum, subserosal space, intestine, stomach, or a subcutaneous pocket.

In some embodiments, cells or cell clusters are encapsulated for transplantation into a subject. Encapsulation techniques are generally classified as microencapsulation, involving small spherical vehicles, and macroencapsulation, involving larger flat-sheet and hollow-fiber membranes (Uludag, H. et al. Technology of mammalian cell encapsulation. Adv Drug Deliv Rev. 2000; 42: 29-64, herein incorporated by reference in its entirety).

Methods of preparing microcapsules include those disclosed by Lu M Z, et al. Biotechnol Bioeng. 2000, 70: 479-83; Chang T M and Prakash S, Mol Biotechnol. 2001, 17: 249-60; and Lu M Z, et al., J. Microencapsul. 2000, 17: 245-51; herein incorporated by reference in their entireties. For example, microcapsules may be prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56; herein incorporated by reference in its entirety). In some embodiments, microcapsules are based on alginate, a marine polysaccharide (Sambanis, Diabetes Technol. Ther. 2003, 5: 665-8; herein incorporated by reference in its entirety) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

In some embodiments, cells generated using methods and reagents described herein are microencapsulated for transplantation into a subject (e.g., to prevent immune destruction of the cells). Microencapsulation of cells (e.g., pancreatic lineage cells, beta-like cells, etc.) provides local protection of implanted/transplanted cells from immune attack (e.g., along with or without the use of systemic immune suppressive drugs). In some embodiments, cells and/or cell clusters are microencapsulated in a polymeric, hydrogel, or other suitable material, including but not limited to: poly(orthoesters), poly(anhydrides), poly(phosphoesters), poly(phosphazenes), polysaccharides, polyesters, poly(lactic acid), poly (L-lysine), poly(glycolic acid), poly(lactic-co-glycolic acid), poly(lactic acid-co-lysine), poly(lactic acid-graft-lysine), polyanhydrides, poly(fatty acid dimer), poly(fumaric acid), poly(sebacic acid), poly(carboxyphenoxy propane), poly (carboxyphenoxy hexane), poly(anhydride-co-imides), poly (amides), poly(ortho esters), poly(iminocarbonates), poly (urethanes), poly(organophasphazenes), poly(phosphates), poly(ethylene vinyl acetate), poly(caprolactone), poly(carbonates), poly(amino acids), poly(acrylates), polyacetals, poly(cyanoacrylates), poly(styrenes), poly(vinyl chloride), poly(vinyl fluoride), poly(vinyl imidazole), chlorosulfonated polyolefins, polyethylene oxide, polystyrene, polysaccharides, alginate, hydroxypropyl cellulose (HPC), N-isopropylacrylamide (NIPA), polyethylene glycol, polyvinyl alcohol (PVA), polyethylenimine, chitosan (CS), chitin, dextran sulfate, heparin, chondroitin sulfate, gelatin, etc., and their derivatives, co-polymers, and mixtures thereof. In some embodiments, cell are microencapsulated in an encapsulant comprising or consisting of alginate. Cells may be embedded in a material or within a particle (e.g., nanoparticle, microparticle, etc.) or other structure (e.g., matrix, nanotube, vesicle, globule, etc.). In some embodiments, microencapsulating structures are modified with immune-modulating or immunosuppressive compounds to reduce or prevent immune response to encapsulated cells. For example, pancreatic lineage cells are encapsulated within an encapsulant material (e.g., alginate hydrogel) that has been modified by attachment of an immune-modulating agent (e.g., the immune modulating chemokine, CXCL12 (also known as SDF-1). In some embodiments, such an immune modulating agent is a T-cell chemorepellent and/or a pro-survival factor.

In some embodiments, cells generated using methods and reagents described herein are macroencapsulated for transplantation into a subject. Macroencapsulation of cells (e.g., pancreatic lineage cells, beta-like cells, etc.), for example, within a permeable or semi-permeable chamber, provides local protection of implanted/transplanted cells from immune attack (e.g., along with or without the use of systemic immune suppressive drugs), prevents spread of cells to other tissues or areas of the body, and/or allows for efficient removal of cells. Suitable devices for macroencapsulation include those described in, for example, U.S. Pat. No. 5,914,262; Uludag, et al., Advanced Drug Delivery Reviews, 2000, pp. 29-64, vol. 42, herein incorporated by reference in their entireties.

Other encapsulation (micro or macro) devices and methods may find use in embodiments described herein. For example, methods and devices described in U.S. Pub No. 20130209421, U.S. Pat. No. 8,785,185, each of which are herein incorporated by reference in their entireties, are within the scope of embodiments described herein.

Islet-Like Clusters The islets of Langerhans are the regions of the pancreas that contain the endocrine (e.g., hormone-producing) cells (e.g., beta cells). In some embodiments, provided herein are islet-like clusters (ILCs) comprising pancreas lineage cells (e.g., beta-like cells or a cell population comprising beta-like cells) generated from pluripotent stems cells by methods, systems, and/or reagents described herein. In some embodiments, cells (e.g., cells generated by methods herein) are transferred from culture (e.g., in a Transwell plate) to an aggregation or cluster forming vessel (e.g., conical well (e.g., AggreWell (e.g., U.S. Pub. No. 2011/0086375; U.S. Pub. No. 2010/0068793; U.S. Pub. No. 2012/0149051; herein incorporated by reference in their entireties)), etc.). In some embodiments, aggregation or cluster forming vessels comprise Matrigel or a similar component. In some embodiments, aggregation or cluster forming vessels do not comprise Matrigel or a similar component. In some embodiments, cells are cultured and/or maintained in the aggregation or cluster forming vessel. In some embodiments, culturing and/or maintenance of cells generated by methods herein, in the absence of an aggregation or cluster forming vessel, results in the formation of islet-like clusters. In some embodiments, upon cluster formation, cells generate by methods herein behave more similarly to naturally-occurring islets of Langerhans (e.g., obtained from cadaver) than ICLs produced by other previous methods (e.g., >50% insulin production compared to naturally-occurring islets of Langerhans (e.g., >60%, >70%, >80%, >90%, >95%, >99%, or approaching or exceeding naturally-occurring islets of Langerhans (e.g., obtained from cadaver)), >50% PDX1 expression compared to naturally-occurring islets of Langerhans (e.g., >60%, >70%, >80%, >90%, >95%, >99%, or approaching or exceeding naturally-occurring islets of Langerhans (e.g., obtained from cadaver)), >50% NKX6.1 expression compared to naturally-occurring islets of Langerhans (e.g., >60%, >70%, >80%, >90%, >95%, >99%, or approaching or exceeding naturally-occurring islets of Langerhans (e.g., obtained from cadaver)), etc.). In some embodiments, cluster are uniform in size (e.g., <50% difference in size of clusters (e.g., <40%, <30%, <20%, <15%, <10%, <5%, etc.)).

Suspension Culturing/Expansion

In some embodiments, post-clustering/post-aggregation cells/clusters are transferred (e.g., from static cultures) to an appropriate dynamic culture system, such as a disposable plastic, reusable plastic, stainless steel or glass vessel (e.g., a spinner flask or an Erlenmeyer flask) for suspension culturing and/or expansion of islet-like. In some embodiments, cells are transferred while still expanding (e.g., day 10, day 11, day 12, day 13, day 14, and ranges therein). Methods of suspension culturing are described, for example in WO 2014/106141, herein incorporated by reference in its entirety.

Applications

The methods, reagents, and kits described herein, as well as the pancreatic lineage cells generated therewith, find use in various research, diagnostic, clinical, and therapeutic applications.

For example, populations of pancreatic lineage cells (e.g., beta-like cells or a cell population comprising beta-like cells) may be used to prepare antibodies and cDNA libraries that are specific for the differentiated phenotype. General techniques used in raising, purifying and modifying antibodies, and their use in immunoassays and immunoisolation methods are described in Handbook of Experimental Immunology (Weir & Blackwell, eds.); Current Protocols in Immunology (Coligan et al., eds.); and Methods of Immunological Analysis (Masseyeff et al., eds., Weinheim: VCH Verlags GmbH). General techniques involved in preparation of mRNA and cDNA libraries are described in RNA Methodologies: A Laboratory Guide for Isolation and Characterization (R. E. Farrell, Academic Press, 1998); cDNA Library Protocols (Cowell & Austin, eds., Humana Press); and Functional Genomics (Hunt & Livesey, eds., 2000). Relatively homogeneous cell populations are particularly suited for use in drug screening and therapeutic applications.

In some embodiments, the pancreatic lineage cells generated by methods provided herein (e.g., beta-like cells or a cell population comprising beta-like cells) are used to screen for agents (e.g., small molecule drugs, peptides, polynucleotides, and the like) or environmental conditions (such as culture conditions or manipulation) that affect the cells. Particular screening applications relate to the testing of pharmaceutical compounds in drug research. Assessment of the activity of candidate pharmaceutical compounds generally involves combining the cells with the candidate compound, determining any change in the morphology, marker phenotype, or metabolic activity of the cells that is attributable to the compound (compared with untreated cells or cells treated with an inert compound), and then correlating the effect of the compound with the observed change. Any suitable assays for detecting changes associated with test agents may find use in such embodiments. The screening may be done, for example, either because the compound is designed to have a pharmacological effect on pancreatic cell types, because a compound designed to have effects elsewhere may have unintended side effects, or because the compound is part of a library screen for a desired effect. Two or more drugs can be tested in combination (by combining with the cells either simultaneously or sequentially), to detect possible drug-drug interaction effects. In some applications, compounds are screened for cytotoxicity.

In some embodiments, methods and systems are provided for assessing the safety and efficacy of drugs that act upon insulin-producing pancreatic β cell, or drugs that might be used for another purpose but may have unintended effects upon pancreatic cells. In some embodiments, cells described herein (e.g., glucose-responsive cells) find use in high throughput screening (HTS) applications. In some embodiments, a HTS screening platform is provided (e.g., cells and plates) that allows for the rapid testing of large number (e.g., $1\times10^3$, $1\times10^4$, $1\times10^5$, $1\times10^6$ or more) of agents (e.g., small molecule compounds, peptides, etc.).

In some embodiments, pancreatic lineage cells generated using methods and reagents described herein (e.g., beta-like cells or a cell population comprising beta-like cells) are utilized for therapeutic delivery to a subject (e.g., with diabetes). Cells may be placed directly in contact with subject tissue or may be otherwise sealed or encapsulated (e.g., to avoid direct contact). In embodiments in which cells are encapsulated, exchange of factors (e.g., glucose, insulin, etc.), nutrients, gases, etc. between the encapsulated cells and the subject tissue is allowed. In some embodiments, cells are implanted/transplanted on a matrix or other delivery platform.

In some embodiments, pancreatic lineage cells (e.g., beta-like cells or a cell population comprising beta-like cells) are used for direct transplantation into a subject (e.g., for the treatment of diabetes (e.g., type I diabetes), etc.).

In some embodiments, pancreatic lineage cells generated by methods herein (e.g., beta-like cells or a cell population comprising beta-like cells) are useful for diagnostic, prognostic, and/or therapeutic uses.

In some embodiments, the methods and kits described herein are useful for identifying additional factors, reagents, and methods for the generation or pancreatic lineage cells or other cell types. The methods used herein may be used to screen factors, reagents and/or conditions for their effect of differentiation. In some embodiments, any screening performed in this or other embodiments discussed herein may be high-throughput screening.

In some embodiments, methods and reagents described herein and the pancreatic lineage cells generated therewith find use in the commercial or industrial production of various cell-derived factors (e.g., non-recombinant insulin).

EXPERIMENTAL

Example 1

Exemplary Culture Media

Experiments were conducted during development of embodiments described herein to develop a multistage set of culture media for generation of pancreatic lineage cells from human stem cells.

Stage 1 Culture Medium
  CDM (Chemical Defined Medium)
  100 ng/ml bFGF (Invitrogen PHG0021)
  100 ng/ml Activin A (R&D 338-AC-050)
  50 ng/ml BMP4 (R&D 314-BP)
CDM:
  100 ml DMEM/F12 (Invitrogen, 11330-057)
  1 ml nonessential amino acids (1% final conc., 1 mM, Invitrogen, 11140)
  1 ml L-glutamine (1% final conc. 2 mM, Invitrogen, 25030-081)
  200 ul 2-mercaptoethanol (final conc. 0.11 mM, Invitrogen, 21985)
Stage 2 Culture Medium (DMEM/F12 (Invitrogen, 11330-057))
  ITS (1000× dilution, BD, 354351)
  50 ng/ml FGF7 (R&D 251-KG-050)
  10 mM Nicotinamide (Sigma, N0636-100 g)
Stage 3 Culture Medium (DMEM/F12 (Invitrogen, 11330-057))
  ITS (1000× dilution, BD, 354351)
  2 uM Retinoic Acid (Sigma, R2625-50 MG)
  300 ng/ml Noggin (R&D 6057-NG-100)
  10 mM Nicotinamide (Sigma, N0636-100 g)
Stage 4 Culture Medium (I'IIBFINE+ALK5i+Forskolin (DMEM/F12 (Invitrogen, 11330-057)))
  150 ng/ml IGF I (Invitrogen, PHG0078)
  800 ng/ml IGF II (Invitrogen, PHG0084)
  B27 (50× dilution, Gibco, 05-01295A)
  4 ng/ml Insulin (1,000,000× dilution, Gibco, 12585-014)
  10 ng/ml FGF7 (R&D 251-KG-050)
  10 nM exendin-4 (Sigma, E7144-0.1 MG)
  10 mM Nicotinamide (Sigma, N0636-100 g)
  1 uM ALK5i II (Calbiochem, 616452)
  25 uM forskolin (Tocris, 1099)
Stage 5 Culture Medium
  150 ng/ml IGF I (Invitrogen, PHG0078)
  10 ng/ml FGF7 (R&D 251-KG-050)
  B27 (50× dilution, Gibco, 05-01295A)
  4 ng/ml Insulin (1,000,000× dilution, Gibco, 12585-014)
  10 nM exendin-4 (Sigma, E7144-0.1 MG)
  10 mM Nicotinamide (Sigma, N0636-100 g)
  25 uM forskolin (Tocris, 1099)

Example 2

Preparation of Exemplary Culture Media from Exemplary Kits

Stage 1 Medium
  Reconstitute
    Activin A (R&D 338-AC): 50 ug/5 ml 0.1% BSA/PBS
    BMP4 (R&D 314-BP): 50 ug/5 ml 0.1% BSA/PBS
    bFGF (Invitrogen PHG0021): 100 ug/10 ml 0.1% BSA/PBS
  For 40 ml Stage 1 (Base medium: CDM)

| Reagent | Kit (1000 ul) | ×6.5 |
| --- | --- | --- |
| Activin A | 400 ul | 2.6 ml |
| BMP4 | 200 ul | 3 ml |
| bFGF | 400 ul | 2.6 ml |

Stage 2 Medium
  Reconstitute
    ITS (BD 354351) 5 ml distilled water
    FGF7 (R&D 251-kg): 50 ug/5 ml 0.1% BSA/PBS
    Nicotinamide (Sigma N0636-100 g): 1M stock 3.663 g/30 ml DPBS
  For 40 ml Stage 2 (base media: DMEM/F12, Invitrogen: 11330-057)

| Reagent | Kit (650 ul) | ×6.5 |
| --- | --- | --- |
| ITS | 40 ul | 260 ul |
| FGF7 | 200 ul | 1.3 ml |
| Nicotinamide | 400 ul | 2.6 ml |

Stage 3 Medium
  Reconstitute
    ITS (BD354351) above
    Retinoic acid (Sigma R2625-50 mg): 50 mg/1.5 ml DMSO (do a 1:10 dilution with 100 ul for kit, rest is frozen at 110 mM)
    Noggin (R&D, 6057-NG-100): 100 ug/5 ml 0.1% BSA/PBS
    Nicotinamide (as above)
  For 50 ml Stage 3 (base media: DMEM/F12, Invitrogen: 11330-057)

| Reagent | Kit (1309 ul) | ×6.5 |
| --- | --- | --- |
| ITS | 50 ul | 325 ul |
| Retinoic acid | 9 ul | 58.5 ul |
| Noggin | 750 ul | 4.875 ml |
| Nicotinamide | 500 ul | 3.25 ml |

Stage 4 Medium
  Reconstitute
    IGFI (Invitrogen, PHG0078): 100 ug/1 ml 0.1% BSA/PBS
    IGFII (R&D, 292-G2-250): 250 ug/2.5 ml sterile PBS
    B27 (Gibco, 05-01295A)
    FGF7 (R&D 251-KG-050): 50 ug/5 ml 0.1% BSA/PBS
    Insulin (Gibco, 12585-014): provided 5 ml of a 4 mg/ml stock; Make a 1:1000 dilution: 1 ul/1 ml DMEM/F12

Nicotinamide (Sigma, N0636-100 g): 3.663 g/30 ml PBS (1M)

Exendin-4: (Sigma E7144-0.1 mg): 0.1 mg/1 ml 0.1% BSA/PBS (24 uM)

ALK5i II (Calbiochem, 616452): 2 mg/1 ml DMSO (7 mM)

Forskolin: (Tocris, 1099): 10 mg/974.4 ul DMSO (25 mM)

For 45 ml Stage 4 (base media: DMEM/F12, Invitrogen: 11330-057)

| Reagent (final conc.) | Kit (1938 ul) | ×6.5 (12597 ul) |
|---|---|---|
| IGFI (150 ng/ml) | 67.5 μl | 438.75 μl |
| IGFII (800 ng/ml) | 360 μl | 2340 μl |
| B27 (1x) | 0.9 ml | 5.85 ml |
| FGF7 (10 ng/ml) | 45 μl | 292.5 μl |
| Insulin (4 ng/ml) | 45 μl | 292.5 μl |
| Nicotinamide (10 mM) | 0.45 ml | 2.925 ml |
| Exendin-4 (10 nM) | 19 μl | 123.5 μl |
| ALK5i II (1 uM) | 6.43 μl | 41.975 μl |
| Forskolin (25 uM) | 45 μl | 292.5 μl |

Stage 5 Medium
Reconstitute

IGFI (Invitrogen, PHG0078): 100 ug/1 ml 0.1% BSA/PBS

FGF7 (R&D 251-KG-050): 50 ug/5 ml 0.1% BSA/PBS

B27 (Gibco, 05-01295A)

Insulin (Gibco, 12585-014): provided 5 ml of a 4 mg/ml stock; Make a 1:1000 dilution: 1 ul/1 ml DMEM/F12

Nicotinamide (Sigma, N0636-100 g): 3.663 g/30 ml PBS (1M)

Exendin-4: (Sigma E7144-0.1 mg): 0.1 mg/1 ml 0.1% BSA/PBS (24 uM)

Forskolin: (Tocris, 1099): 10 mg/974.4 ul DMSO (25 mM)

For 45 ml Stage 4 (base media: DMEM/F12, Invitrogen: 11330-057)

| Reagent (final conc.) | Kit (1938 ul) | ×6.5 (12597 ul) |
|---|---|---|
| IGFI (150 ng/ml) | 67.5 μl | 438.75 μl |
| FGF7 (10 ng/ml) | 45 μl | 292.5 μl |
| B27 (1x) | 0.9 ml | 5.85 ml |
| Insulin (4 ng/ml) | 45 μl | 292.5 μl |
| Nicotinamide (10 mM) | 0.45 ml | 2.925 ml |
| Exendin-4 (10 nM) | 19 μl | 123.5 μl |
| Forskolin (25 uM) | 45 μl | 292.5 μl |

Example 3

Exemplary Protocol

Experiments were conducted during development of embodiments described herein to develop a simple four-stage protocol to differentiate human embryonic stem cells and (hESCs) and human induced pluripotent stem cells (hiPSCs) into cells that adopt pancreatic fates. The 18-day protocol (ProgenMix III) employs adherent culturing throughout via a Matrigel-coated Transwell platform. To generate definitive endoderm, Stage 1 culture is based on bFGF/Activin A/BMP4 (FAB) treatment of undifferentiated cells in chemically defined, serum-free (3 days of culture with medium changed daily). Subsequently, in stage 2, cells are cultured with insulin-transferrin-selenium (ITS)/FGF7/nicotinamide (3 days of culture with medium changed daily). To promote expansion of pancreatic progenitors, Stage 3 medium is supplemented with ITS/noggin/nicotinamide/retinoic acid (ITSNR; 4 days of culture with medium changed daily). As cell-to-cell contact intensifies, in Stage 4 cells are treated with a cocktail of ITS/IGFI/IGFII/B27/FGF7/insulin/nicotinamide/exendin4 (ITIIBFINE) plus ALK5i II and forskolin (FIG. 1). Cells are then maintained in a media comprising ITS, IGFI, IGFII, B27, insulin, nicotinamide, exendin4, and forskolin.

The above protocol is distinct from other published protocols, and produces superior results (D'Amour et al. Nat Biotechnol. 2006; 24(11):1392-401; Kunisada et al. Stem Cell Res. 2012; 8(2):274-84; Kroon et al. Nat Biotechnol. 2008; 26(4):443-52; Jiang et al. Cell Res. 2007; 17(4):333-44; herein incorporated by reference in their entireties). For example, the protocol is more efficient, yielding pancreatic progenitor cells with 15-75% greater purity, determined by the output of PDX1+/insulin− cells, which is attributable, in part, to a more reproducible induction of endoderm using FAB (FGF, Activin A and BMP4) compared to Activin alone (Xu et al. Mech Dev. 2011; 128(7-10):412-27; Cho et al. Diabetologia. 2012; 55(12):3284-3295; herein incorporated by reference in their entireties). In addition, based on direct head-to-head comparison, the above protocol produced considerably more PDX1 (8-fold), NKX6.1 (6.5-fold), and insulin (1.7-fold) positive cells following differentiation than the Betalogics protocol (Rezania et al. Diabetes. 2012; 61(8):2016-29; herein incorporated by reference in its entirety). Another method, while reporting in vivo maturation of hESC-derived progenitor cells into functional β cells, did not achieve in vitro glucose stimulated insulin secretion (GSIS) (D'Amour K a, Bang A G, Eliazer S, et al. Nat Biotechnol. 2006; 24(11):1392-401; herein incorporated by reference in its entirety). Cho et al. (Diabetologia. 2012; 55(12):3284-3295; herein incorporated by reference in its entirety) demonstrated GSIS (c-peptide) from hESC-derived insulin-expressing cells, but attempts to repeat these results have been unsuccessful (see FIG. 9). While Cheng et al. (Cell Stem Cell. 2012; 10(4):371-84; herein incorporated by reference in its entirety) showed GSIS from pancreatic progenitors derived from the H9 hESCs, the in vitro derivation of reproducibly and robustly glucose-responsive, insulin-secreting cells from hPSCs has yet to be demonstrated. Indeed, Hrvatin et al. (*Proc Natl Acad Sci USA*. 2014; 111(8):3038-43; herein incorporated by reference in its entirety) recently demonstrated that hPSC-derived beta cells behave more like fetal, than adult beta cells and were not only double positive for hormones insulin and glucagon but also showed poor secretory responses to glucose stimulation. The differentiation strategies described herein, utilize a specialized defined media formulation and unique Transwell platform, making it possible to achieve a high yield of insulin+ cells (~20%), the majority of which are monohormonal (insulin+glucagon−) that exhibit significant GSIS. Additionally, the method is reproducible using multiple pluripotent stem cells lines and when performed by different users.

Example 4

Preparation of Undifferentiated Cells and Matrigel Coated Plates

Undifferentiated human embryonic stem cells (hESCs) or human induced pluripotent stem cells (hiPSCs) are cultured under standard conditions in stem cell media. Cells should be cultured in a 6 well plate in mTeSR media on Matrigel (1 mg/6 well). Cells are ready for Stage 1 when ~80-90% confluent.

On the day of splitting, a Matrigel coated plate is prepared. One aliquot of growth factor-reduced Matrigel (1 mg/tube) is thawed and diluted with 3 ml cold (4° C.) DMEM/F12. 0.15 ml of diluted Matrigel is added to the plate. The plate sits at room temperature for at least one hour prior to use. Before adding cells, any remaining Matrigel solution is aspirated from the inserts and washed once with PBS. PBS is aspirated and 0.5 ml of mTeSR is added to the lower compartment. The upper compartment is filled with cell suspension.

When undifferentiated ES cells are 80-90% confluent, they are detached by adding 1 ml of 2 mg/ml dispase to each well. The cells are incubated at 25° C. and observed under microscope until the edges of colonies begin to fold. Dispase is then carefully aspirated. Cells are washed once with PBS.

The cells are collected into a 15 ml conical tube by gently rinsing and scraping with 2 ml of mTeSR. The well is rinsed with an additional 2 ml of mTeSR. The cells are allowed to settle at room temperature to pellet cells. Supernatant is carefully aspirated, and 4 ml mTeSR is added to the pellet and pipet to disperse. Size of clusters/colonies should be ~200-500 um. 0.3 ml of cell suspension is added to the Matrigel coated inserts (prepared above). To distribute the cells evenly the plate is quickly shaken several times in the x and y planes, without swirling. Cells are cultured overnight at 37° C. on incubator rack.

The cells are then examined by microscopy 24 hours after passaging. Two wells of a 6-well plate should be sufficient to create a confluent monolayer of cells in the inserts. If there is poor attachment, mTeSR media is changed daily until cells reach 80% confluence.

Example 5

Stage 1 (Days 0-2)

Spent media is aspirated from both the upper and lower compartments. 0.5 ml of Stage 1 media (CDM, bFGF, Activin A, and BMP4) is added to the lower compartment and 0.3 ml Stage 1 media is added to the upper compartment. Media is exchanged daily and cells are cultured at 37° C. on incubator rack.

Example 6

Stage 2 (Days 3-5)

On day 3, Stage 2 media (ITS, FGF7, and nicotinamide) is prepared and brought to room temperature. Spent media is aspirated from both the upper and lower compartments. 0.5 ml of Stage 2 media to the lower compartment and 0.3 ml of Stage 2 media is added to the upper compartment. Media is exchanged daily, and between media changes cells are cultured at 37° C. on incubator rack.

Example 7

Stage 3 (Days 6-9)

On day 6, Stage 3 media (ITS, retinoic acid, Noggin, and nicotinamide) is prepared and brought to room temperature. Spent media is aspirated from both the upper and lower compartments. 0.5 ml of Stage 3 media to the lower compartment and 0.3 ml of Stage 3 media is added to the upper compartment. Media is exchanged daily, and between media changes cells are cultured at 37° C. on incubator rack.

Example 8

Stage 4 (Days 10-18)

On day 10, Stage 4 media (IGF I, IGF II, B27, insulin, FGF7, exendin-4, nicotinamide, ALK5i II, and forskolin) is prepared and brought to room temperature. Spent media is aspirated from both the upper and lower compartments. 0.5 ml of Stage 4 media to the lower compartment and 0.3 ml of Stage 4 media is added to the upper compartment. Media is exchanged daily, and between media changes cells are cultured at 37° C. on incubator rack.

Example 9

Stage 5 (Days 19+)

On day 19, Stage 5 media (IGF I, IGF II, B27, insulin, exendin-4, nicotinamide, and forskolin) is prepared and brought to room temperature. Spent media is aspirated from both the upper and lower compartments. 0.5 ml of Stage 5 media to the lower compartment and 0.3 ml of Stage 5 media is added to the upper compartment. Media is exchanged daily, and between media changes cells are cultured at 37° C. on incubator rack.

Example 10

Results

Figure 5:
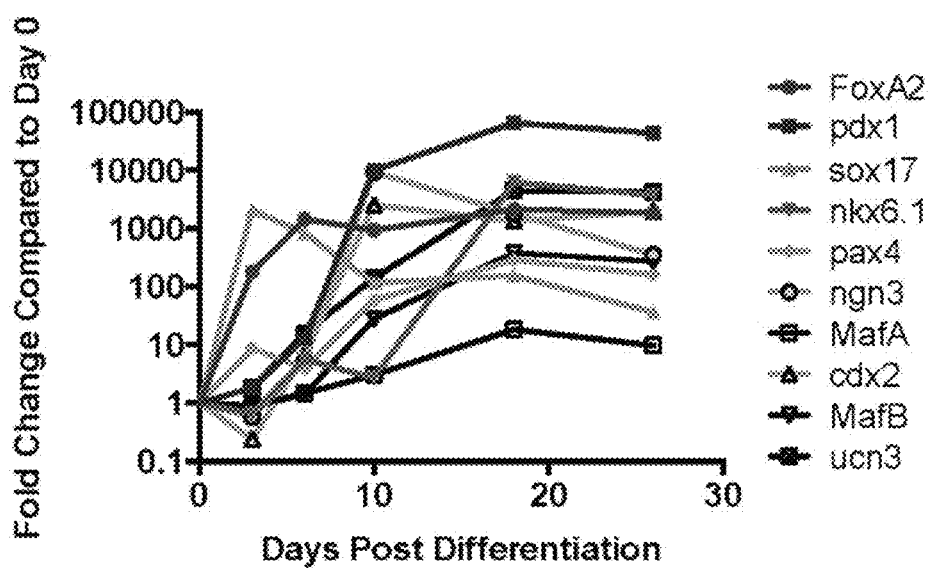
FIG. 5 shows a graph demonstrating increased gene expression of insulin, PDX1, PAX4, and urocortin 3 (UCN3) by day 18, well-accepted markers of β cells. MAFA: typical marker of mature "adult" β cells. MAFB: typical marker of immature β cells. Urocortin 3 (ucn3): marker of mature β cells. Sox17: marker of endoderm which would be expected to decline. FoxA2 is expressed in endoderm and adult beta cells. These in vitro expression patterns are very similar to in human islet measurements
Figure 6:
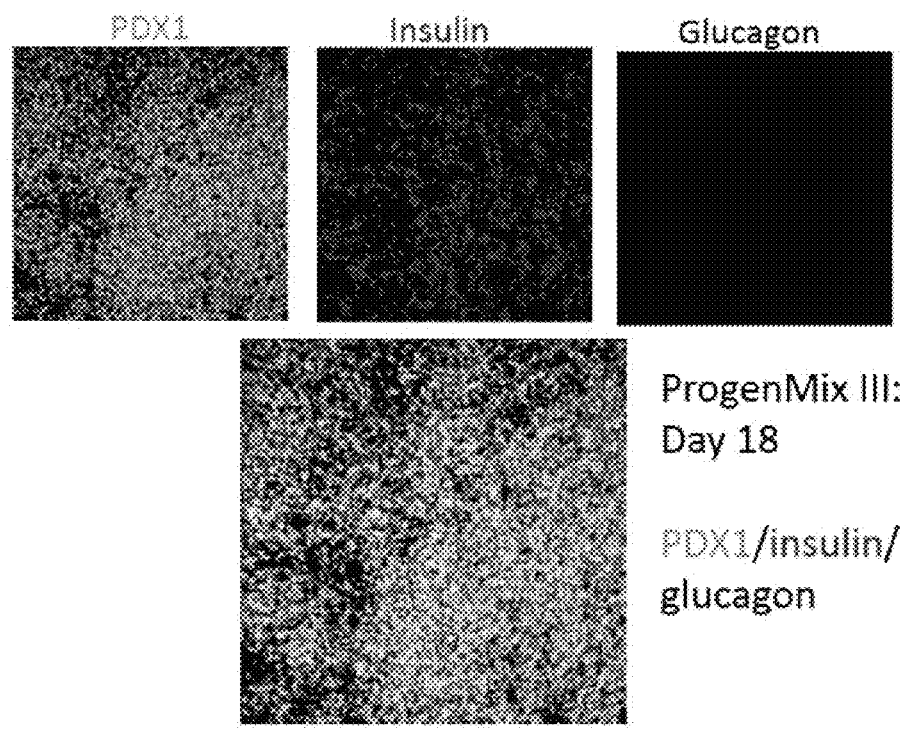
FIG. 6 shows immunostaining of insulin, PDX1 and glucagon (day 18). The bottom image is an overlay of the 3 panels at top.
Figure 7:
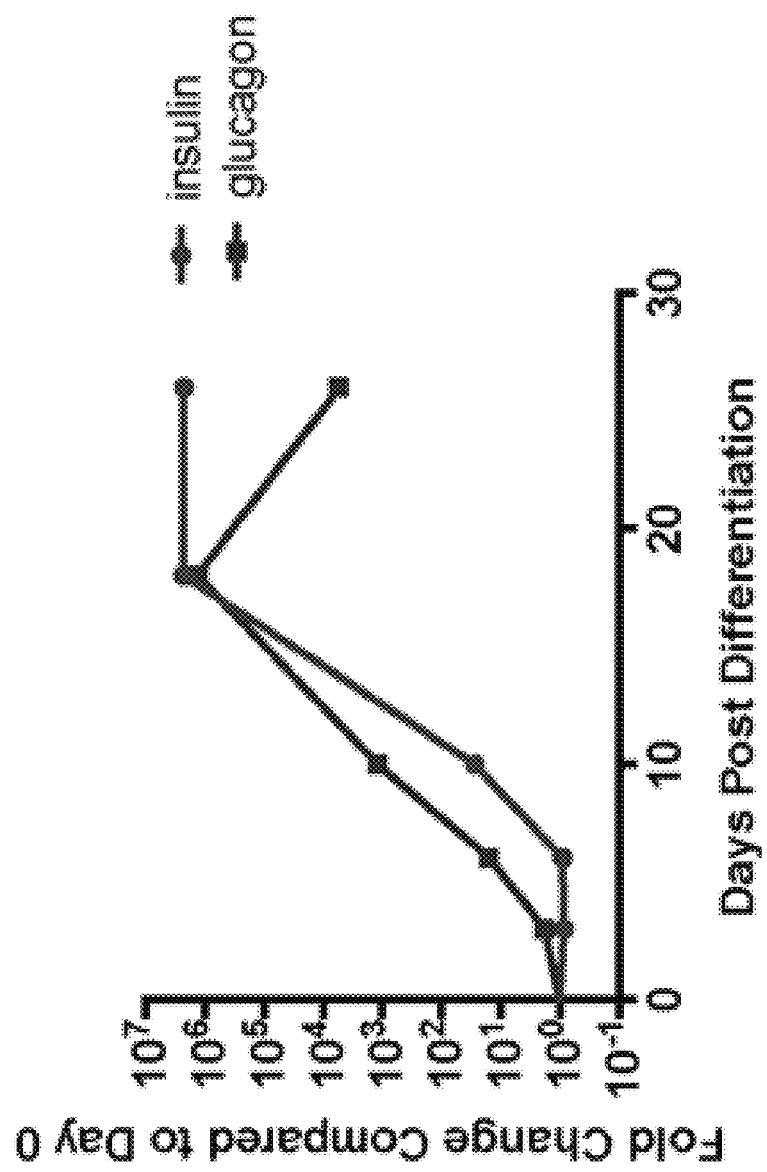
FIG. 7 shows a graph depicting insulin and glucagon expression (measured by qPCR) as a function of days post-differentiation.

Kits and method described herein provide a stepwise differentiation process (see FIG. 1) that converts human pluripotent stem cells into β-like cells that exhibit classical characteristics of mature human β cells including typical β cell gene expression patterns and significant GSIS (measured as c-peptide, by ELISA, Millipore #EZHCP-20K). Using the human embryonic stem cell line H1, cells successfully increased gene expression of insulin, PDX1, PAX4, and urocortin 3 (UCN3) by day 18, well-accepted markers of β cells (FIG. 5). Gene expression was maintained from day 18 to day 25 for key mature β cell markers, PDX1, UCN3, and NKX6.1 (FIG. 5). Increased co-expression of insulin and PDX1 was observed in the absence of significant glucagon expression (as measured by immunostaining) (FIG. 6), which was consistent with qPCR results (FIG. 7).

Figure 8:
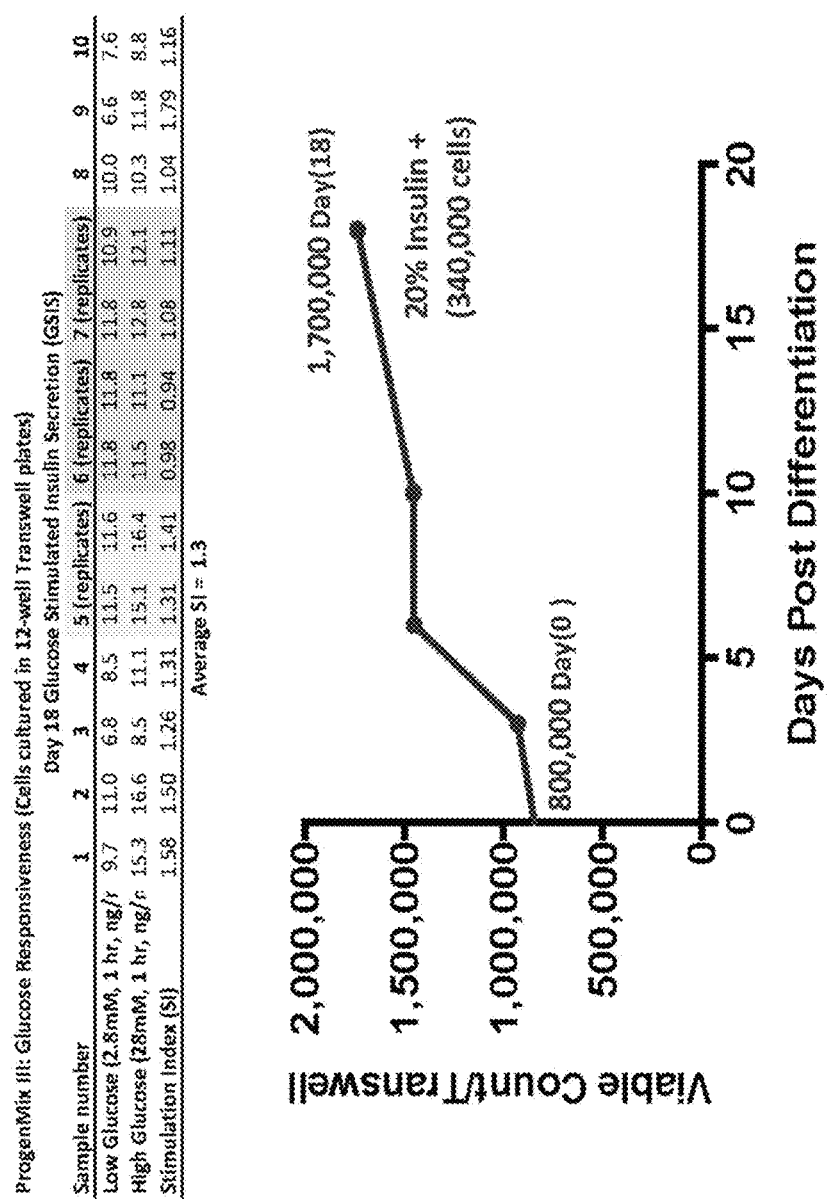
FIG. 8 shows a chart and graph of glucose responsiveness as a function of days post-differentiation.

Cell number increased more than two-fold, of which 20% were insulin positive (FIG. 8). The cells also exhibited significant GSIS (measured as c-peptide) (FIG. 8). Overall, the methods and kits described herein generate an expanded population of insulin monohormonal cells (20%) with improved pancreatic marker expression extending beyond 20 days and a Stimulation Index (SI) averaging 1.3 (with SI's above 2).

Example 11

Differentiation of hiPSC Lines, H1 hES Cells

Figure 9:
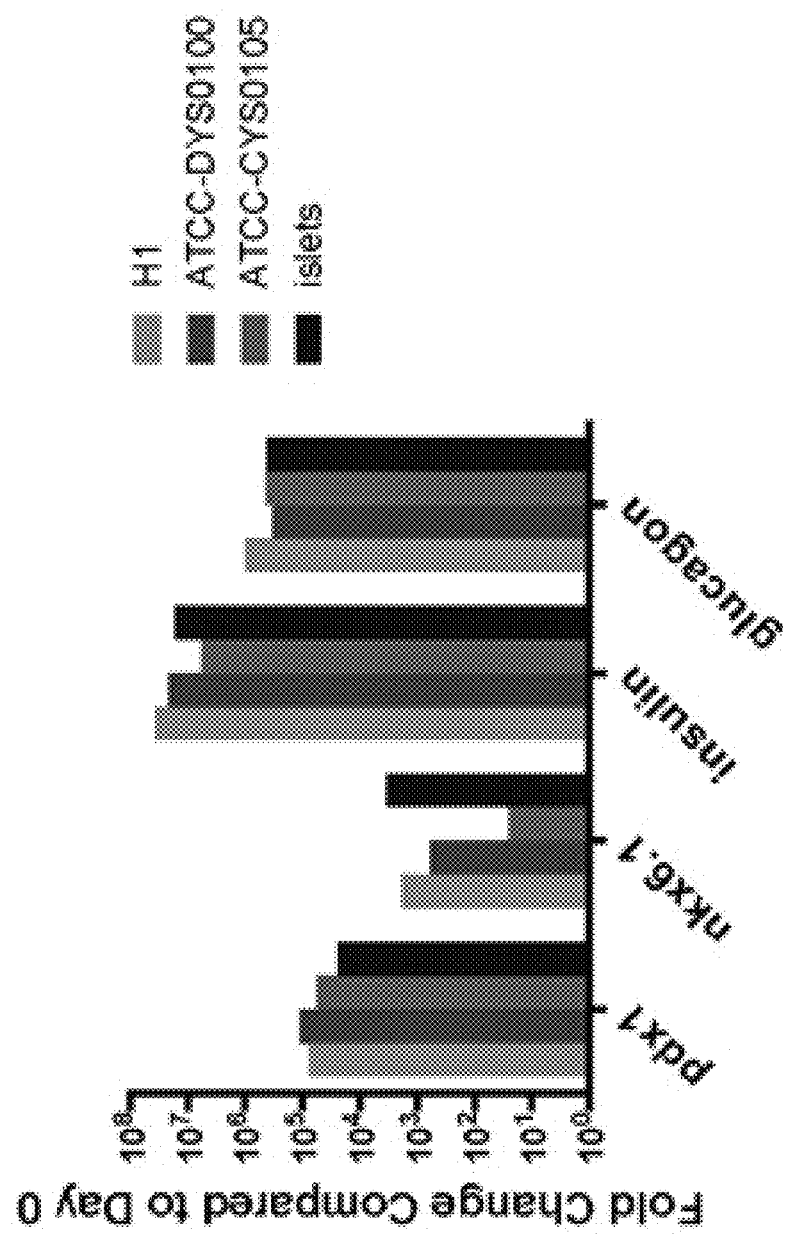
FIG. 9 shows a graph depicting gene expression in β-like cells from three pluripotent stem cell lines.

Methods described herein were used to induce pancreatic differentiation of two hiPSC lines obtained from ATCC and the H1 hES cell line to day 18. PDX1, NKX6.1, insulin and glucagon gene expression were analyzed by qPCR and compared to results with cadaver sourced human islet cells. FIG. 9 demonstrates that both ATCC cell lines showed similar PDX1, insulin and glucagon gene expression compared to H1 cells and human islets.

Figure 10:
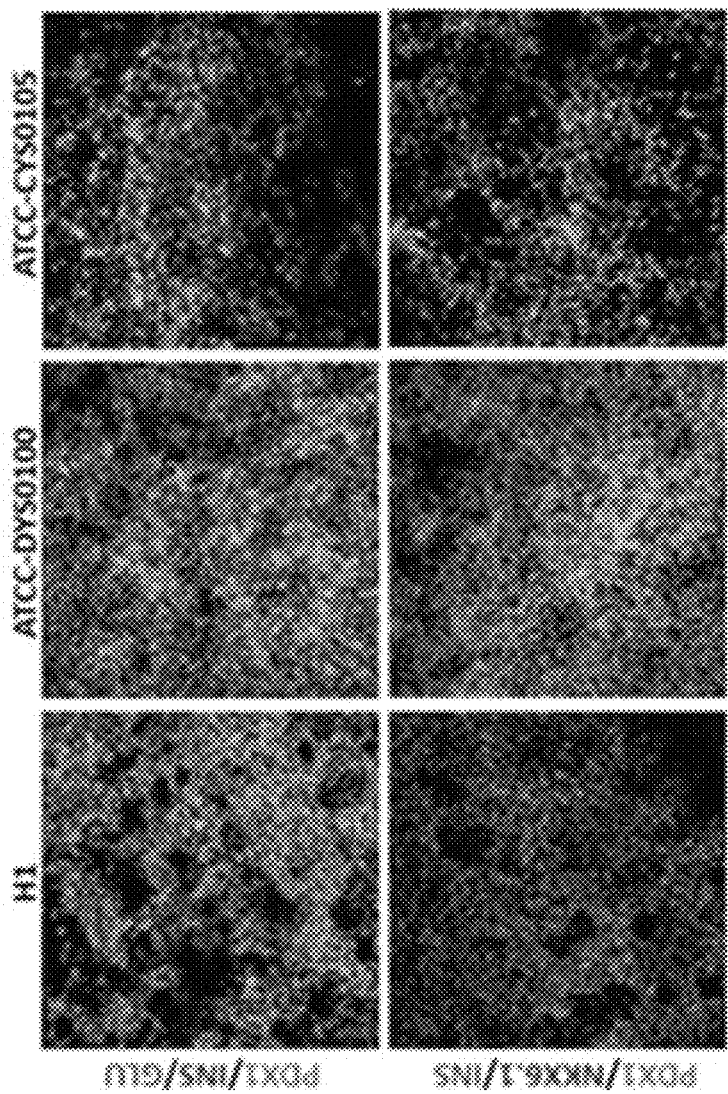
FIG. 10 shows immunostaining of PDX1, insulin (INS), NKX6.1 and glucagon (GLU) (day 18) of H1 hESCs and two hiPSC lines.

However, NKX6.1 gene expression was lower in the ATCC line-derived cultures compared to H1-derived cultures and human islets. Immunofluorescence staining for PDX1, insulin and glucagon of the ATCC lines compared to the H1 cell lines show primarily PDX1+insulin+glucagon− cells (FIG. 10).

Example 12

Results Using 96-Well Transwell Plates

Figure 11:
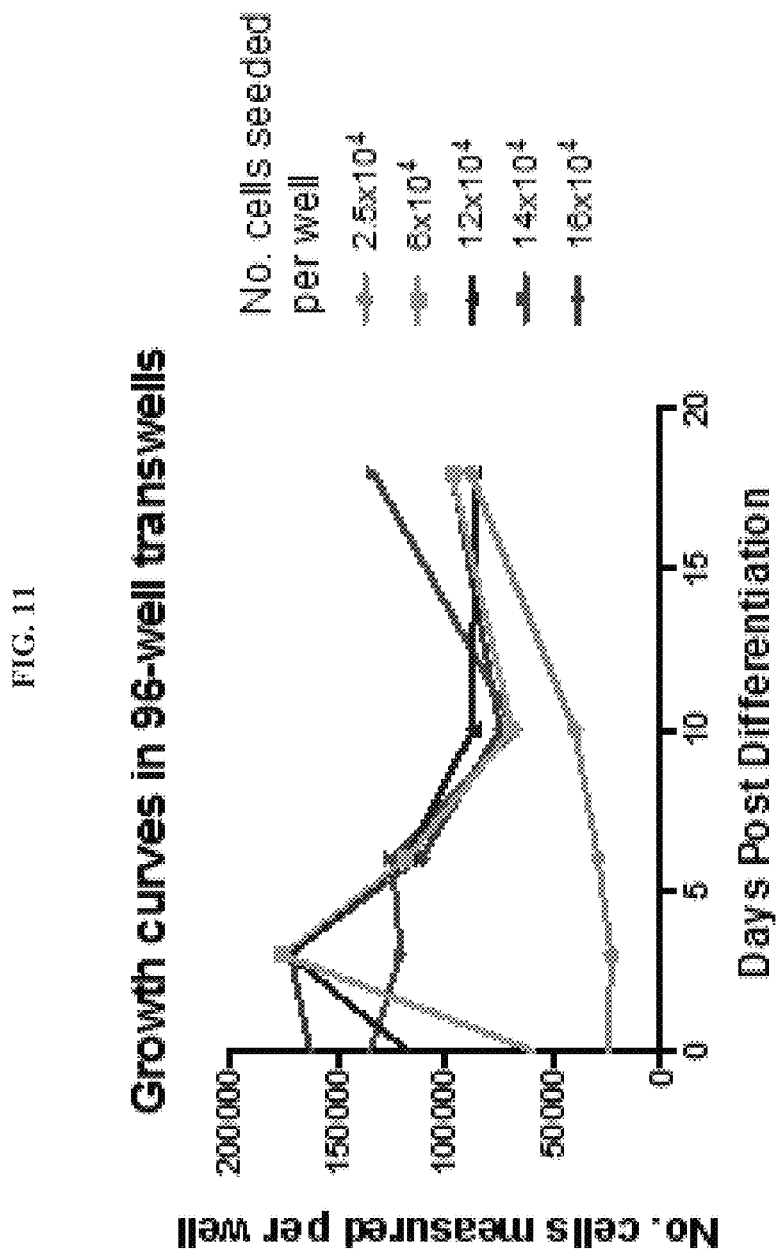
FIG. 11 shows a graph depicting post-differentiation growth curves.

H1 human embryonic stem cells were cultured at 5 different densities in 96-well Transwell plates and differentiated using the methods described herein (FIG. 11). The seeding density of $6.0 \times 10^4$ cells/well (42 cells/cm$^2$) is similar to typical seeding density in 12-well plates ($45 \times 10^4$ cells/cm$^2$). While the seeding cell numbers varied by 6.4-fold, the total number of cells after the 18 day differentiation process varied less than 1.5-fold. Interestingly, the average cell number at day 18 was similar for the different seeding densities. This finding contrasts with results using 12-well Transwell plates where the total cell number typically doubles over the 18-day differentiation period (see FIG. 8).

Figure 12:
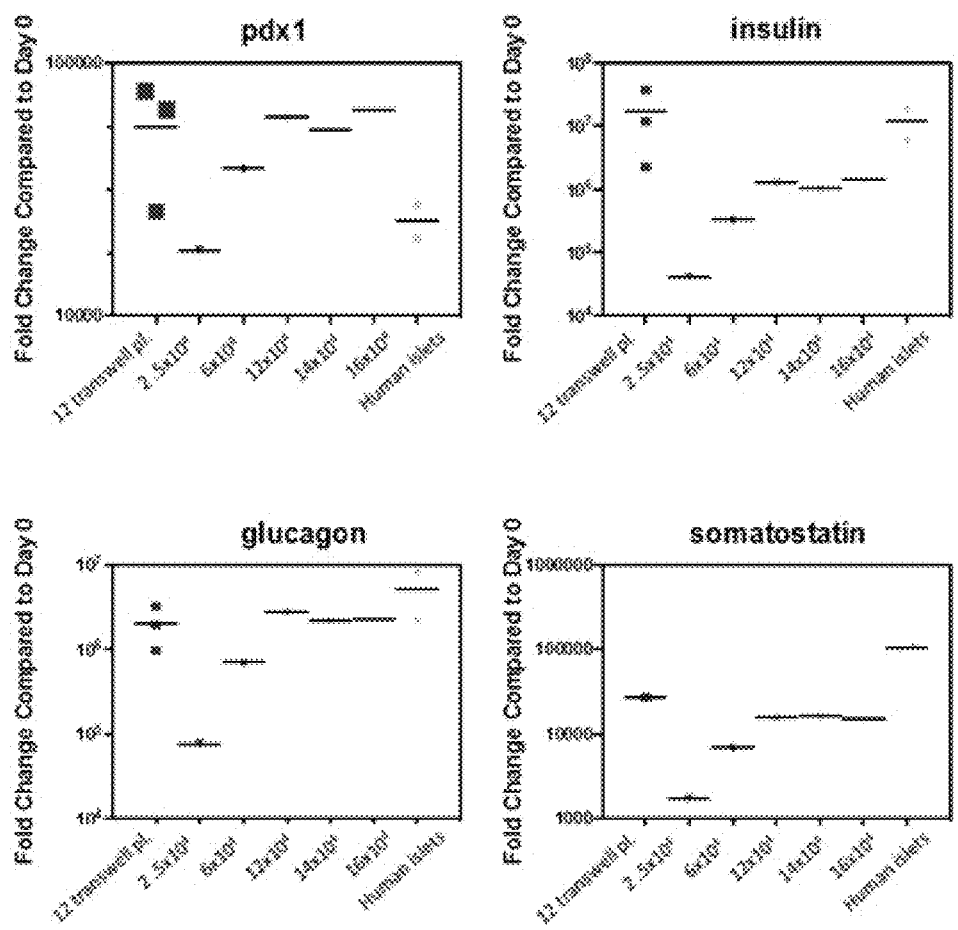
FIG. 12 shows graphs depicting the change in transcript expression at day 18 compared to day 0.
Figure 13:
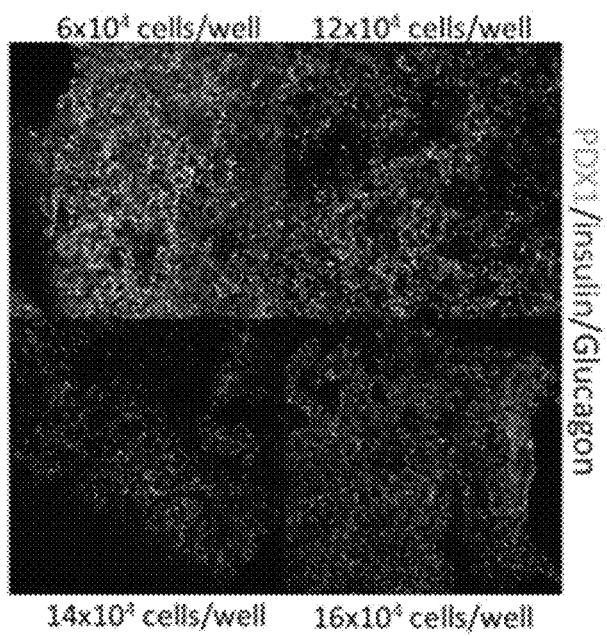
FIG. 13 shows immunostaining of PDX1, insulin and glucagon at day 18 for cells initially seeded at different densities.
Figure 14:
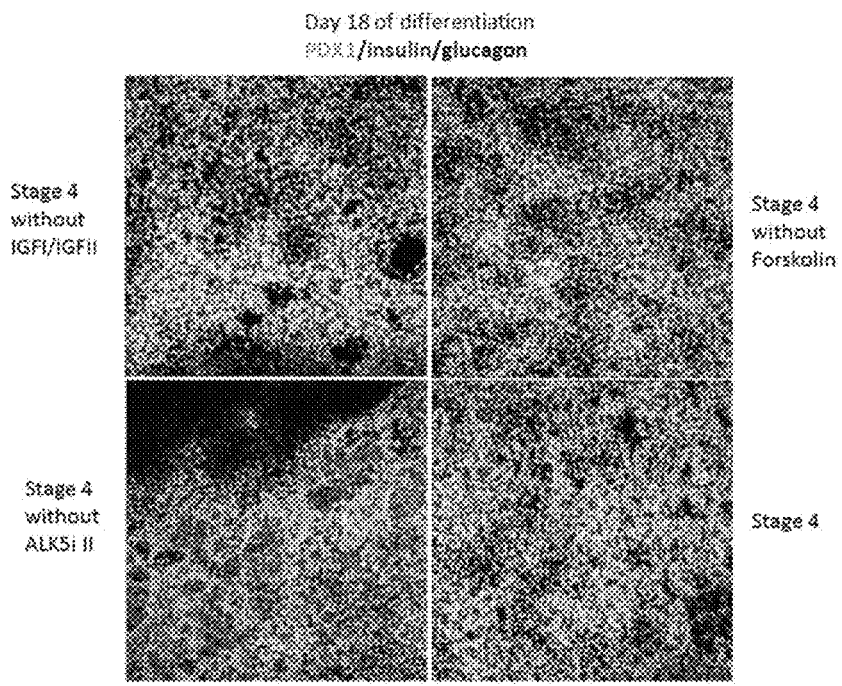
FIG. 14 shows immunostaining demonstrating that without IGFI/IGFII or forskolin or ALK5i II in stage 4 media, there was increased insulin and glucagon co-staining and decreased PDX1/insulin co-staining.

Day 18 gene expression patterns in the 96-well Transwell plates also differed relative to 12-well Transwell cultures (FIG. 12). While PDX1, glucagon and somatostatin levels were similar in 96- and 12-well plates at seeding densities $\geq 12 \times 10^4$ cells/well, insulin expression was less in the 96-well plates. Nevertheless, immunohistochemical staining of the day 18 cultures revealed many monohormonal insulin+ cells (FIG. 13).

Example 13

Formation of Islet-Like Clusters (ILCs)

Figure 15:
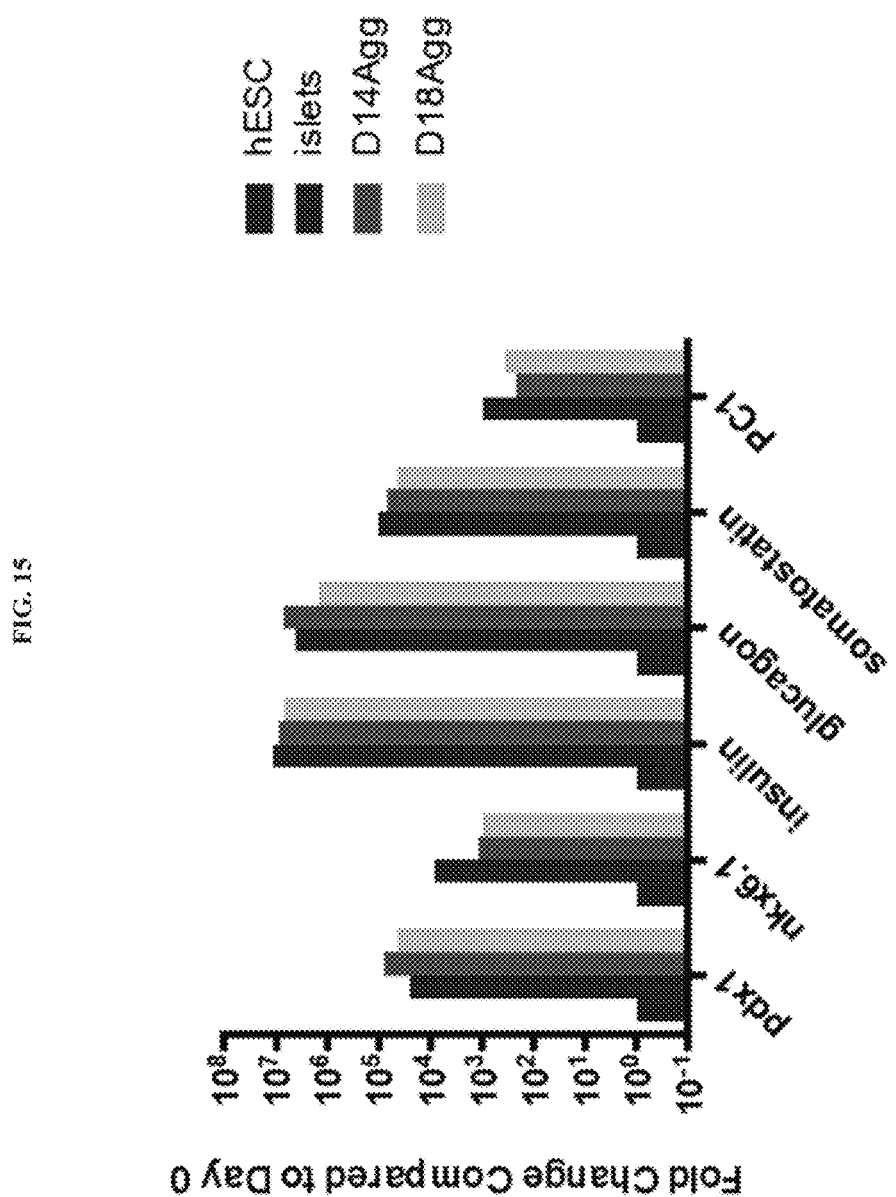
FIG. 15 shows a graph depicting gene expression, as determined by qPCR, in islet-like clusters.
Figure 16:
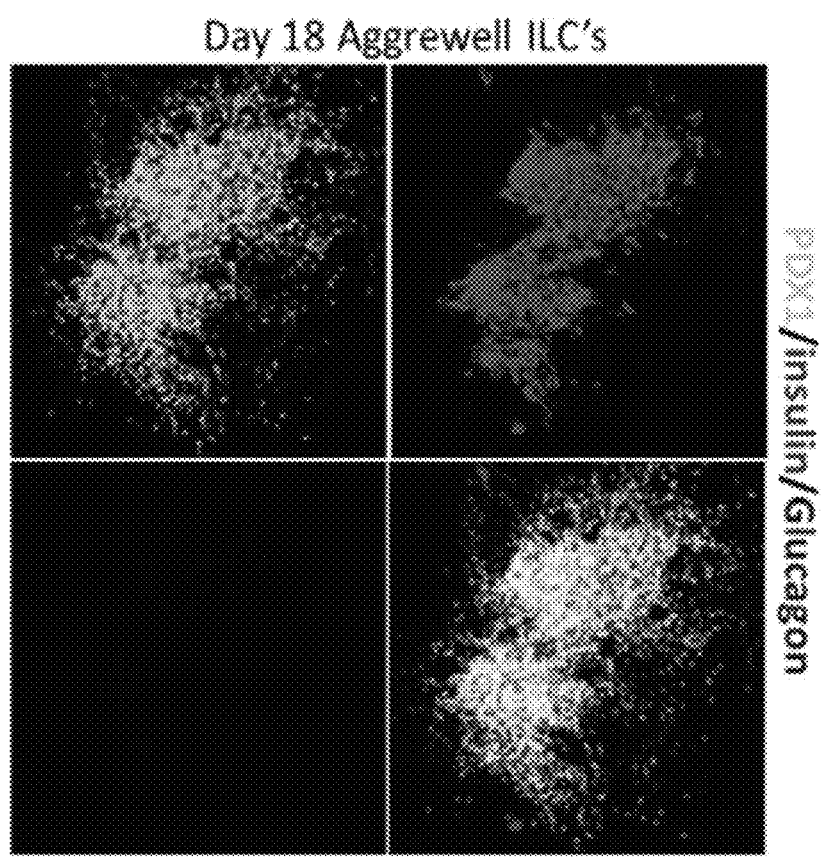
FIG. 16 shows immunostaining results depicting insulin and PDX1 expression with minimal glucagon coexpression in islet-like clusters at day 18.
Figure 17:
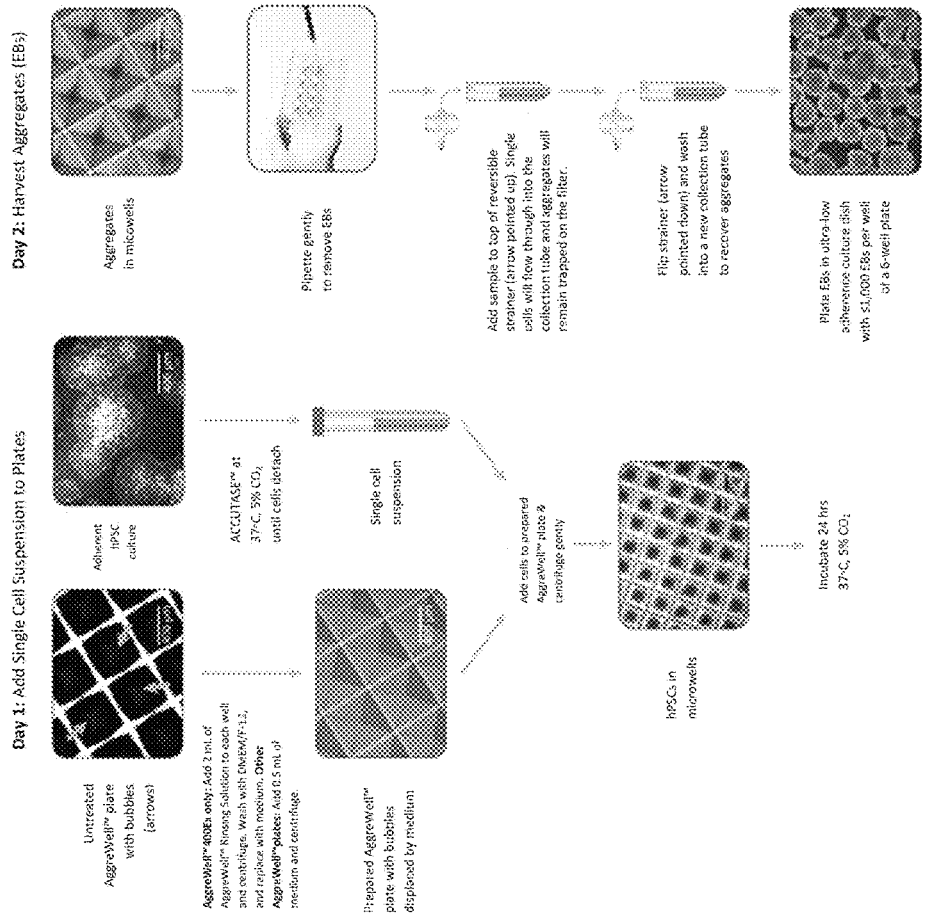
FIG. 17 shows an exemplary two-day cell aggregation procedure.
Figure 18:
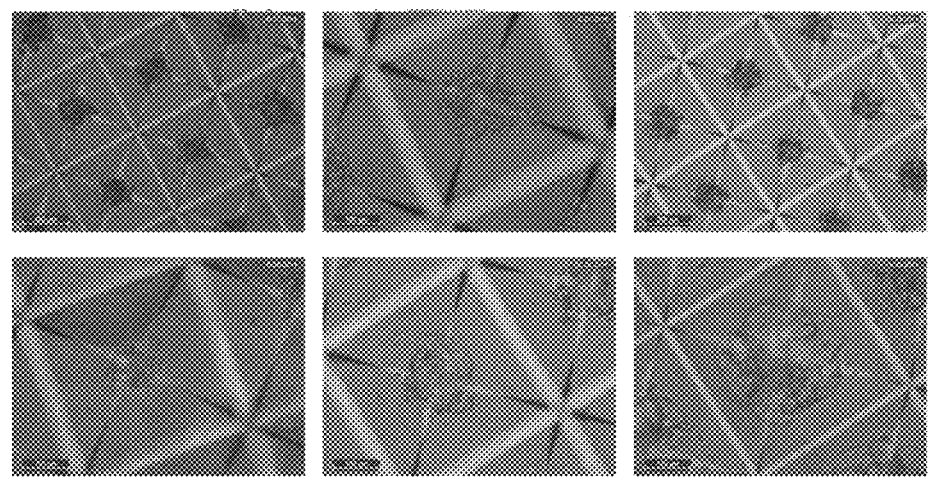
FIG. 18 shows images of islet-like cluster aggregates after two days in AggreWell.
Figure 19A:
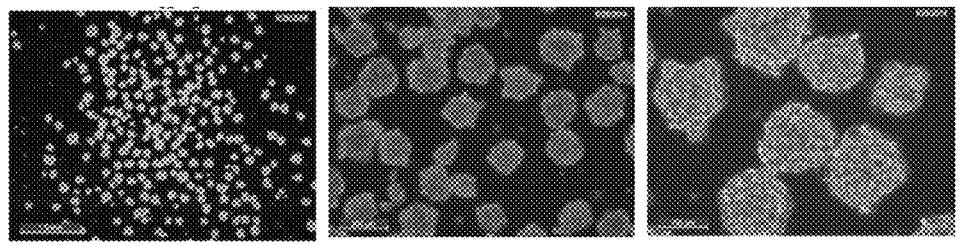
FIG. 19A-B shows images of (A) islet-like cluster aggregates after two days in AggreWell, and (B) islet-like cluster aggregates after two days in AggreWell followed by culturing.
Figure 19B:
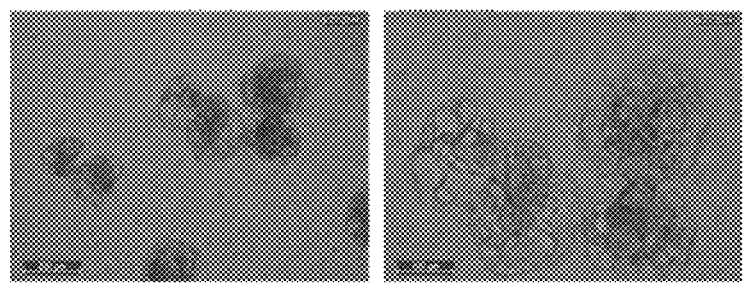

To convert differentiated pancreatic lineage cells (e.g., cells generated by methods described herein) into ILCs, cells are liberated from Transwell dishes using TrypLE™ Select dissociation reagent (Life Tech.) and allowed to spontaneously aggregate in AggreWell dishes (Stem Cell Technologies) (FIG. 17). These ILCs (FIG. 18-19), which contain approximately 800-1000 cells, measure 200 µM in diameter, express genes (qPCR) characteristic of human islets (FIG. 15), and exhibit co-expression of insulin and PDX1 with minimal glucagon coexpression (as measured by immunostaining), particularly at day 18 (FIG. 16).

The islet-like clusters exhibited classical characteristics of mature human β cells in pancreatic islets, including significant GSIS (See Table 1).

Example 14

Microencapsulation

Experiments are conducted to define parameters for combining pancreatic lineage cells (e.g., induced beta-like cells, cells produced by methods described herein) with immune protective alginate based encapsulation technology. The ability of the encapsulated cells to evade immune destruction and correct hyperglycemia (e.g., in a murine model of diabetes) is tested. The functionality of CXCL12/alginate encapsulated islet-like clusters is tested in vitro. Doses and ratio of components for use in humans are determined. The ability of encapsulated pancreatic cells and/or islet-like clusters with CXCL12 to restore euglycemia in an immune-competent streptozotocin-induced murine model of diabetes is demonstrated.

The efficacy of the chemokine, CXCL12, as an immuno-protective agent for transplanted islets has been demonstrated (Duncanson and Sambanis. Biotechnol Bioeng. 2013 August; 110(8):2292-300; herein incorporated by reference in its entirety). It has been demonstrated that high concentrations (1 µg/mL) of the chemokine act as a T cell chemorepellent in the context of alloislet transplantation in murine models of T1D (Dunussi-Joannopoulos et al. Blood 100, 1551-8 (2002); Nomura et al. Int. J. Cancer 91, 597-606 (2001); herein incorporated by reference in their entireties). It has been shown that insulin-producing cells, including islets secreting high levels of CXCL12, induced T-cell migration away from such cells in vitro (Papeta, N. et al. Transplantation 83, 174-83 (2007); herein incorporated by reference in its entirety). It has also shown that high levels of CXCL12 secretion by target cells (1 µg/ml) impaired the efficacy of cytotoxic T lymphocyte (CTL) killing (Papeta, N. et al. Transplantation 83, 174-83 (2007); Vianello, F. et al. J. Immunol. 175, 5115-25 (2005); herein incorporated by reference in its entirety). It was demonstrated that the principle effect of CXCL12 in vivo is on CD8+ T-cell chemorepulsion although an effect on CD4+ T-cells is also plausible (Guo, Z. et al. Transplantation 71, 1656-65 (2001); Friedman et al. Diabetes 48, 2340-8 (1999); herein incorporated by reference in their entireties). CXCL12 did not affect levels of CXCR4 expression, insulin production or the growth kinetics of islets in vitro and in immune naïve mice. High levels of CXCL12 did not appear to affect T cell apoptosis and activation or down-regulate expression of MHC-1 or MNC-II by target cells.

Experiments were conducted to explore the incorporation of CXCL12 into Ca-LVM based alginates (Ca-LVM-CXCL12) in order to provide a more sustained source of the chemokine to protect and preserve islets in vivo. It was

TABLE 1

GSIS Data: Insulin secretion from Islet-like clusters (ILCs) generated from H1 hES cells)

| 1 hour GSIS Low glucose (5 mM) insulin secretion (ng/ml) | ~0.5 × 10↑6 cells/well High glucose (25 mM) insulin secretion (ng/ml) | Ratio | 0.8 to 1.0 ml total volume Number of cells used to make clusters | 10 µl out of 1 ml assayed Total days in culture |
| --- | --- | --- | --- | --- |
| 0.75 | 2.07 | 2.77 | 1000 | 21 |
| 1.48 | 3.78 | 2.56 | 1000 | 21 |
| 0.38 | 1.44 | 3.79 | 500 | 18 |
| Ratio mean ± STDEV.P | | 3.04 | 0.54 | |

Method 1: Cells in 12-well Transwell plate trypsinized on day 14, in Aggrewell for 2 days, in suspension 1-4 days (6-well plate), islet GSIS protocol (cells transferred to a Millicell ® placed in a 24-well)

found that the incorporation of CXCL12 into Ca-LVM alginate significantly prolonged islet function and survival in the context of intraperitoneal encapsulated allogeneic islet transplantation into diabetic NOD mice in comparison to the unmodified Ca-LVM alginate. Survival and function of transplanted CXCL12-coated islets was shown to be associated with a significantly decreased infiltrate of effector T cells and an increase in the infiltration of regulatory T cells. The Ca-LVM based alginate encapsulant incorporating CXCL12 supported alloislet survival in vitro and long-term function in vivo in a STZ induced diabetic model. Immunohistochemical studies of retrieved CXCL12-capsules revealed intact islet morphology in comparison to unmodified capsules in which islets were necrotic (100-300 days post transplantation). The CXCL12 containing alginate also induced long-term protection of alloislets in diabetic mice with pre-existent humoral and cell mediated anti-islet responses in comparison to controls receiving encapsulated islets without CXCL12. Furthermore, an alginate-based micro-encapsulant incorporating CXCL12 was also capable of inducing longterm islet immune protection of porcine xenoislets, compared to controls. Removal of grafts at 100 days in euglycemic sensitized encapsulated alloislet recipients, and euglycemic encapsulated xenoislet recipients at 300 days post transplantation resulted in an immediate return to the diabetic state, thus confirming that the CXCL12 protected islets were functioning appropriately and maintaining the euglycemic state.

Pluripotent stem cells are subjected to conditions described herein to generate pancreatic linage cells (e.g., beta-like cells). Cells are then aggregated into ILCs using methods described herein. Cells differentiated and aggregated into ILCs are shipped overnight in the Stage 4 medium and allowed to recover for 24 hours prior to encapsulation. After a 24-hour recovery period, the ILCs are divided into two treatment groups and the control group: Ca-LVM encapsulated ILCs and Ca-LVM-CXCL12 encapsulated ILCs, and unencapsulated ILCs alone (control). For the Ca-LVM-CXCL12 encapsulated ILCs, the concentrations of CXCL12 are tested at 10 ng/ml, 100 ng/ml and 1 µg/ml. The cells are encapsulated with an Inotech encapsulator to generate alginate capsules of approximately 500-600 µm in diameter, each containing one ILC comprising 800-1000 cells. Following encapsulation, cells will be subjected to analysis as described below.

To test cell survival, each encapsulation condition is compared to the control group, assessing cell viability by dithizone staining, microscopic examination, caspase-3 activity by ELISA and the Bio-Rad TC20™ Automated Cell Counter) (Hanson et al. Transplantation, 89 (10), 1178-88 (2010); herein incorporated by reference in its entirety).

To test changes in ILC gene expression, conditions which do not negatively impact cell survival are further analyzed to determine the effect of the transportation and encapsulation process (with or without CXCL12) on the differentiation status of the ILCs based upon the expression of key marker genes including insulin, PDX1 and NKX6.1. Experiments are also extended to determine CXCL12 and CXCR4 expression by ILCs. CXCR4 is the cognate receptor for CXCL12, which have been shown to be present on insulin producing islet derived cells as assessed by immunofluorescence microscopy and to mediate CXCL12 induced prosurvival effects on this cell type (Liu & Habener. Diabetologia 52, 1589-98 (2009); Xu et al. Mech. Dev. 128, 412-27 (2011); herein incorporated by reference in their entireties).

To assess glucose responsiveness, the effect of the encapsulation process (+/−CXCL12) on the glucose-responsiveness of the ILCs is tested using a static glucose-stimulated insulin secretion assay in which the cells are incubated in either low- or high-glucose medium and insulin release into the supernatant is monitored by ELISA (Balamurugan et al. Diabetes Res. Clin. Prac. 66 (1), 13-21 (2004); herein incorporated by reference in its entirety). CXCL12 retention and release from the encapsulants is performed by solubilizing the capsules in sodium citrate at specific time points and the samples assayed by ELISA. Encapsulation conditions, which do not interfere with viability, differentiation status, and glucose responsiveness of the cells, are selected for in vivo testing. In this way optimal in vitro ILC encapsulation conditions are determined.

Each of the encapsulation conditions (Ca-LVM encapsulated ILCs, and Ca-LVM-CXCL12 (10 ng, 100 ng and 1 µg/ml) encapsulated ILCs) are compared to the control, unencapsulated ILCs, by assessing the survival and time matching outbreak. The intraperitoneal route of transplantation is used. Following establishment of an optimal encapsulation protocol for ILCs, the functional efficacy of the encapsulated cells is assessed in a normoglycemic SCID mouse model. A range of encapsulated ILCs are tested (200, 400 and 800) to define the one that produces functional levels of human insulin. The encapsulated ILCs (or unencapsulated controls) are transplanted intraperitoneally. Survival studies are performed for all treatment and control groups. Blood glucose is monitored until three sequential blood glucose recordings are made in each animal of >300 mg/dl at which point animals are sacrificed for immunological and immunohistochemical (IHC) studies.

Functional survival of the grafts is quantitated by monitoring random fed and glucosestimulated human insulin and CXCL12 levels in the blood of recipient mice on a weekly basis post transplantation, with pre-transplantation blood serving as a negative control.

Engrafted mice are maintained for 2, 6 and 12 weeks, at which time-points they are sacrificed and the graft removed for histological analysis, which includes staining for immunological and inflammation markers (F4/80 and S100A4, macrophage and fibroblast markers respectively) as well as for the pancreatic differentiation markers to confirm that the cellular differentiation function of the ILCs has been maintained throughout engraftment.

Encapsulated cells are transplanted into C57BL/6 mice rendered diabetic by streptozotocin (STZ) treatment. Six-week old C57BL/6 mice are rendered diabetic by intraperitoneal injection of 200 mg/kg streptozotocin. Mice are monitored for three consecutive times following treatment to ensure that stable hyperglycemia (≥250 mg/dl random blood glucose) has been established. Hyperglycemic mice are then randomized to receive either unencapsulated cells, Ca-LVM encapsulated cells, or cells encapsulated using the optimized application of CXCL12. Ca-LVM encapsulated cells.

Following transplantation, random fed mice blood glucose levels; human insulin and CXCL12 levels and GSIS are monitored on a weekly basis in all treatment groups and the control group. In the context of survival studies, blood glucose is monitored until three sequential blood glucose recordings are made in each animal of >300 mg/dl at which point animals are sacrificed for immunological and immunopathological studies. Survival studies are run up to 150 days post-transplant, and glucose tolerance tests are performed at days 10, 50 and 100-post transplantation.

Glycemic control and native pancreas insulin immunostaining is assessed post-graft removal to evaluate whether the graft was sustaining normoglycemia. Following explantation, the removed grafts are examined for cell capsule infiltration (F4/80 and S100A4) and insulin secretion is compared to the control.

Example 15

Differentiation Results

The differentiation protocols described above are modified with the addition of kinase inhibitors and antioxidants. Stage 6 culture medium is supplemented with the antioxidant glutathione (GSH) and the kinase inhibitor LY294002.

Islet-like clusters are generated in stage 6 of the differentiation protocol. The method comprises treating attached stage 5 cells with Dispase® I (neutral protease) or other dissociating agent such as Accutase and EDTA to lift cells off culture surfaces and disaggregating "sheets" of cells into small cell clusters by repeated pipetting. The dispersed cells are cultured in Corning ultra-low attachment flasks/plates (T25 & T75 flasks and 6-well plates) in stage 6 medium.

The components of stage 6 medium used are shown below.
B-27® supplement (Life Technologies cat. no. 17504-044) (without insulin): 50 fold dilution
ALK5i: 10
Forskolin: 25 µM
ZnSO4: 10 µM
T3: 1 µM
Heparin: 10 µg/ml
LY294002 (Life Technologies cat. no PHZ1144): 10 µM
Glutathione (GSH): 10 mM.

Figure 27:
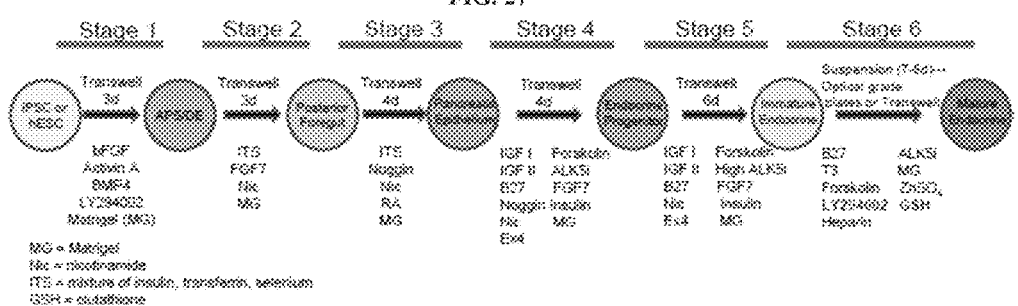
FIG. 27 shows a flow chart of an exemplary differentiation method of embodiments of the present disclosure.

FIG. 27 shows the complete differentiation protocol.

Figure 28:
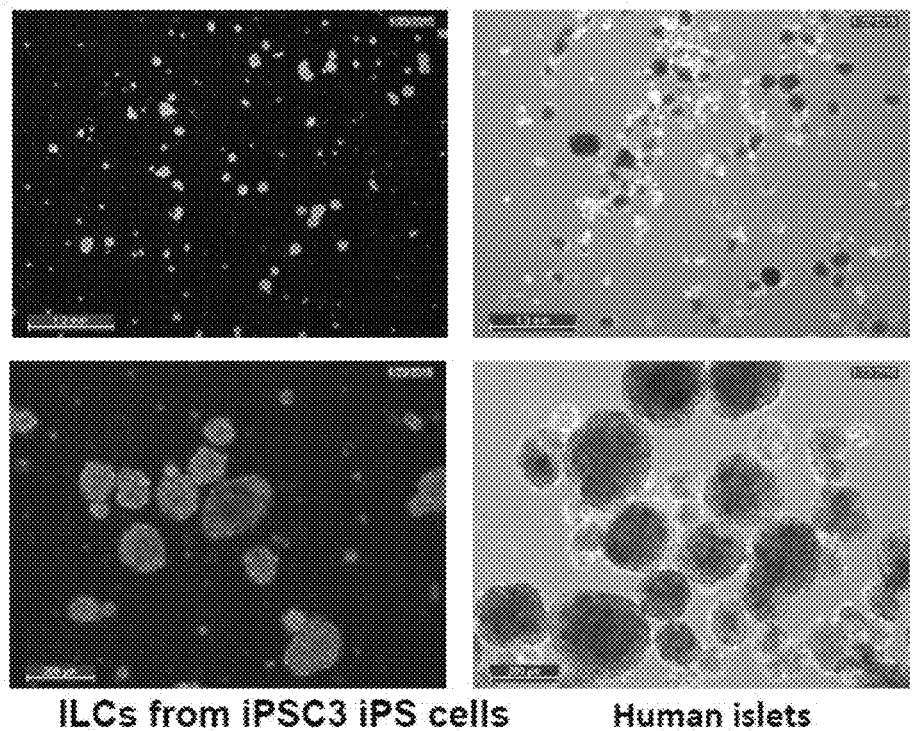
FIG. 28 shows images of islet cells and cells differentiated using the methods described herein.
Figure 29:
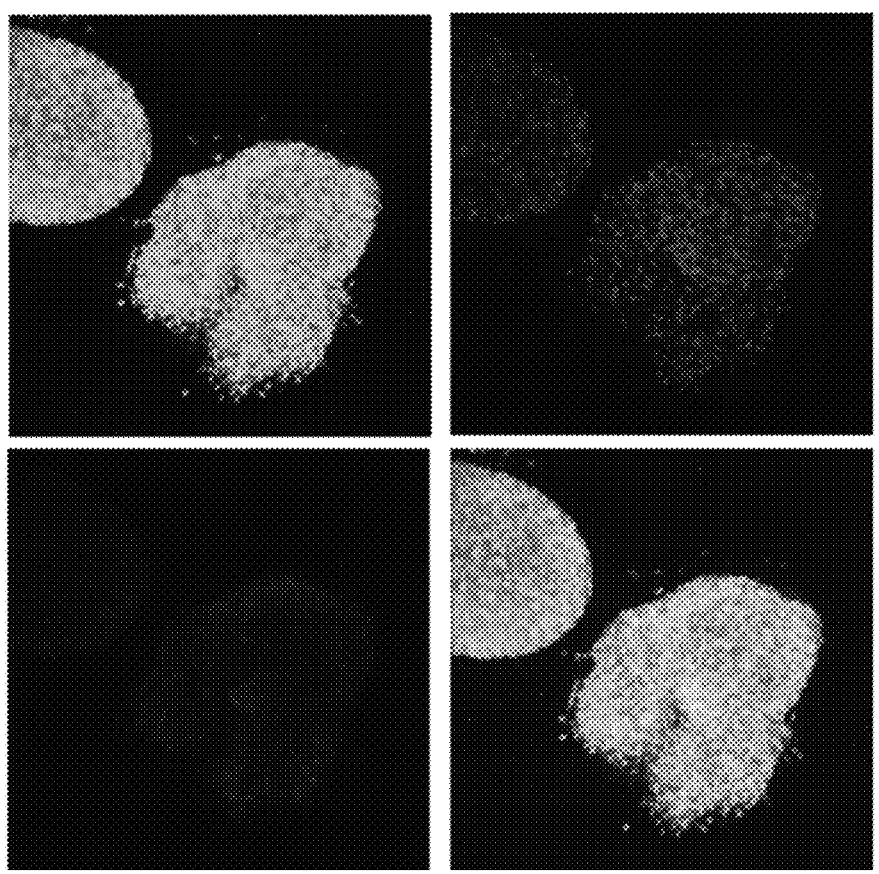
FIG. 29 shows expression of PDX1, insulin and glucagon expression in cell cells differentiated using the methods described herein.
Figure 30:
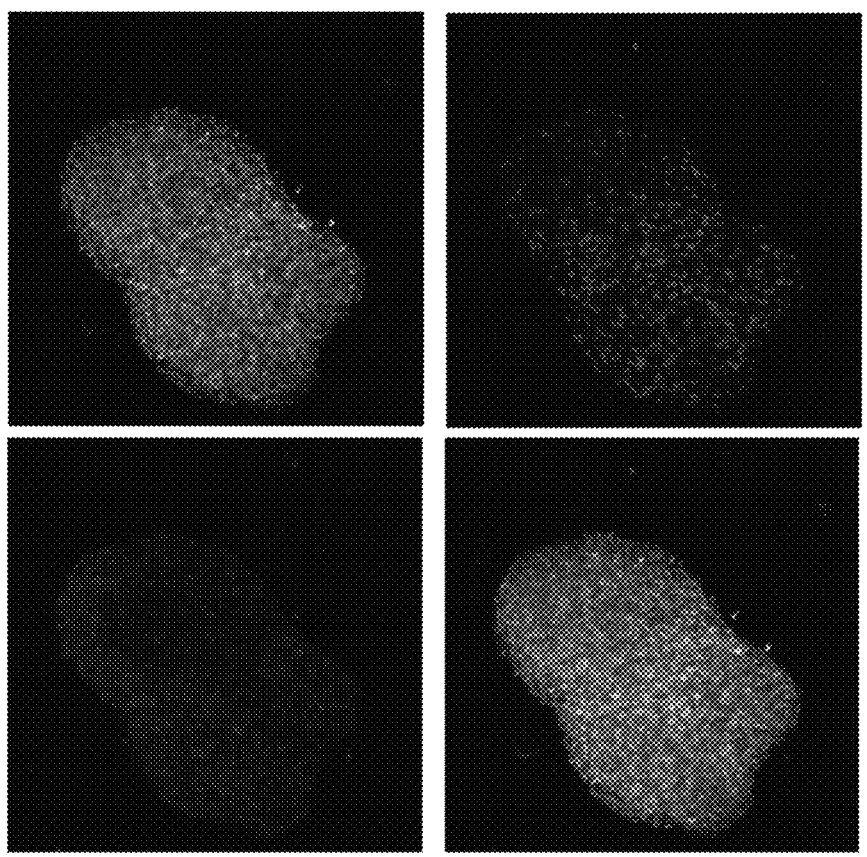
FIG. 30 shows expression of insulin and NKXX6.1 in cells differentiated using the methods described herein.
Figure 31:
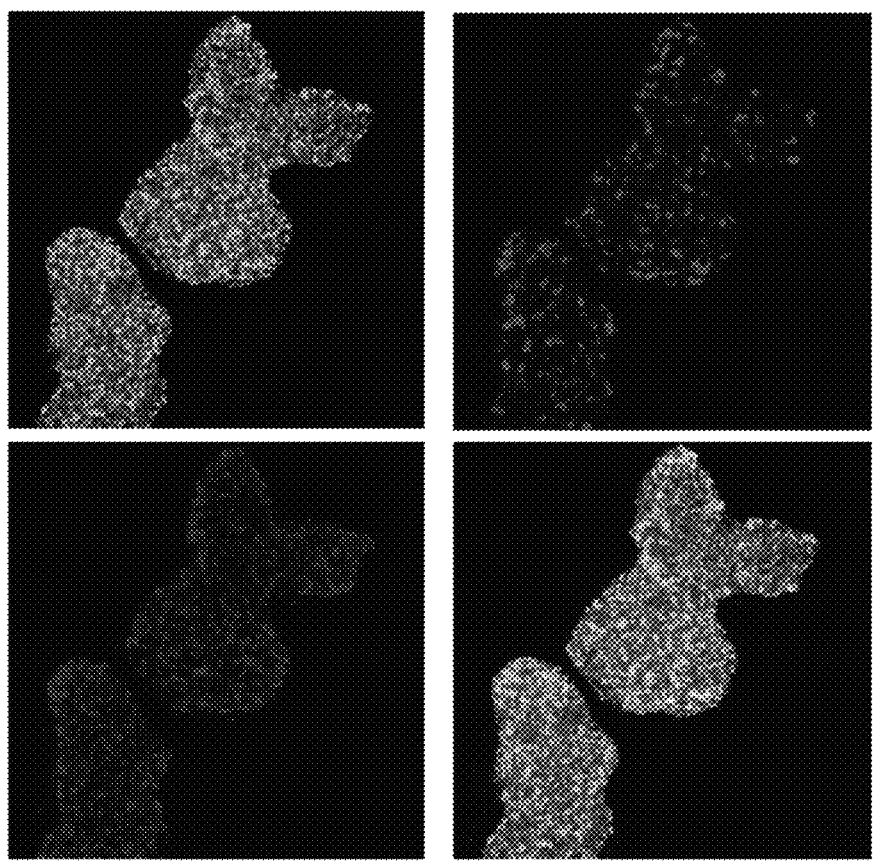
FIG. 31 shows expression of MafA in cells differentiated using the methods described herein.
Figure 32:
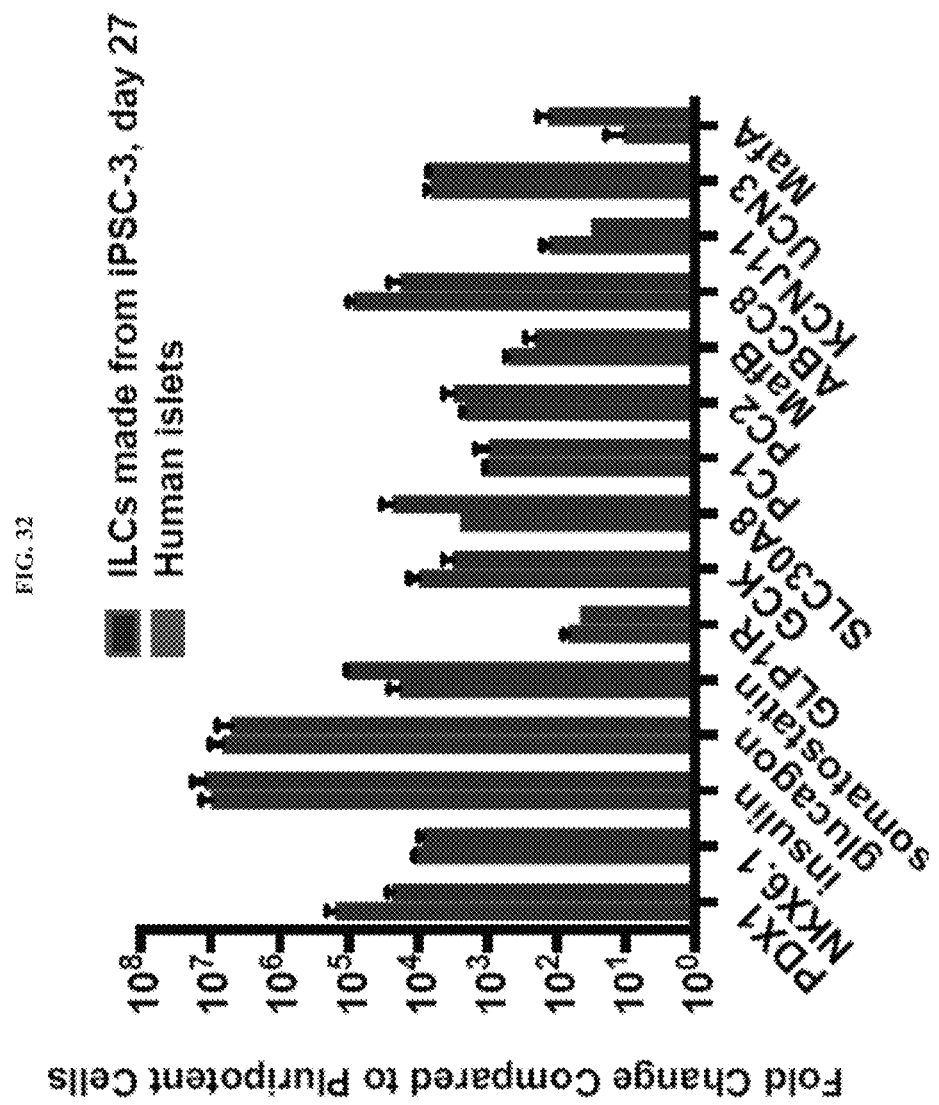
FIG. 32 shows expression of somatostatin in cells differentiated using the methods described herein.
Figure 33:
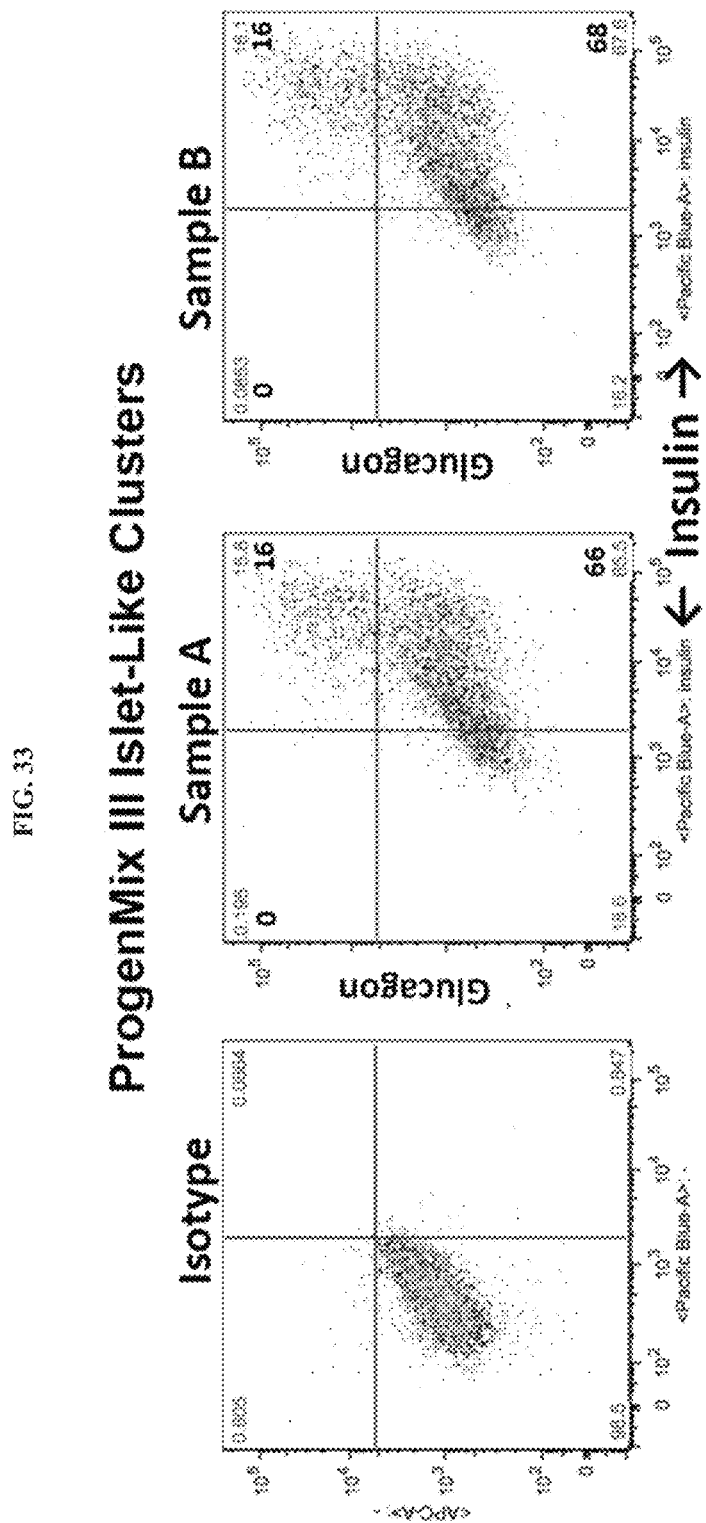
FIG. 33 shows gene expression profiles in cells differentiated using the methods described herein.
Figure 34:
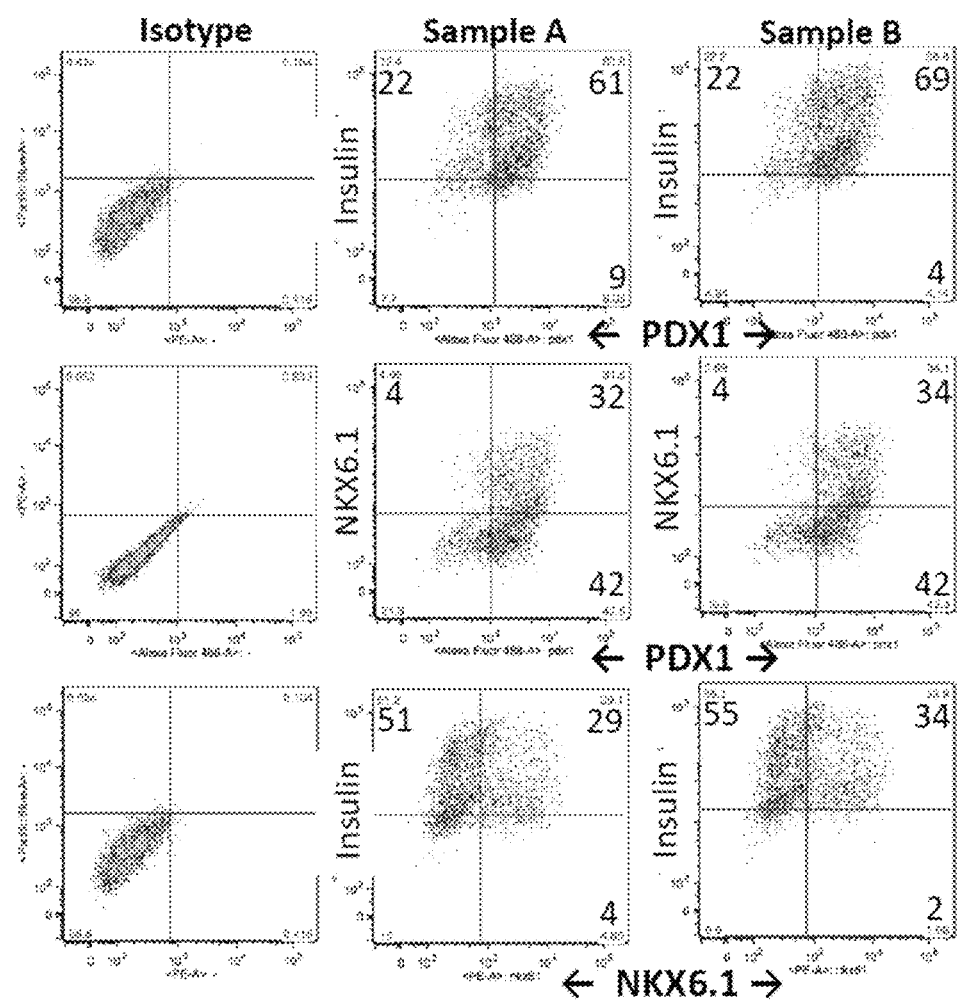
FIG. 34 shows that cells differentiated using the methods described herein are insulin+ and glucagon−.
Figure 36:
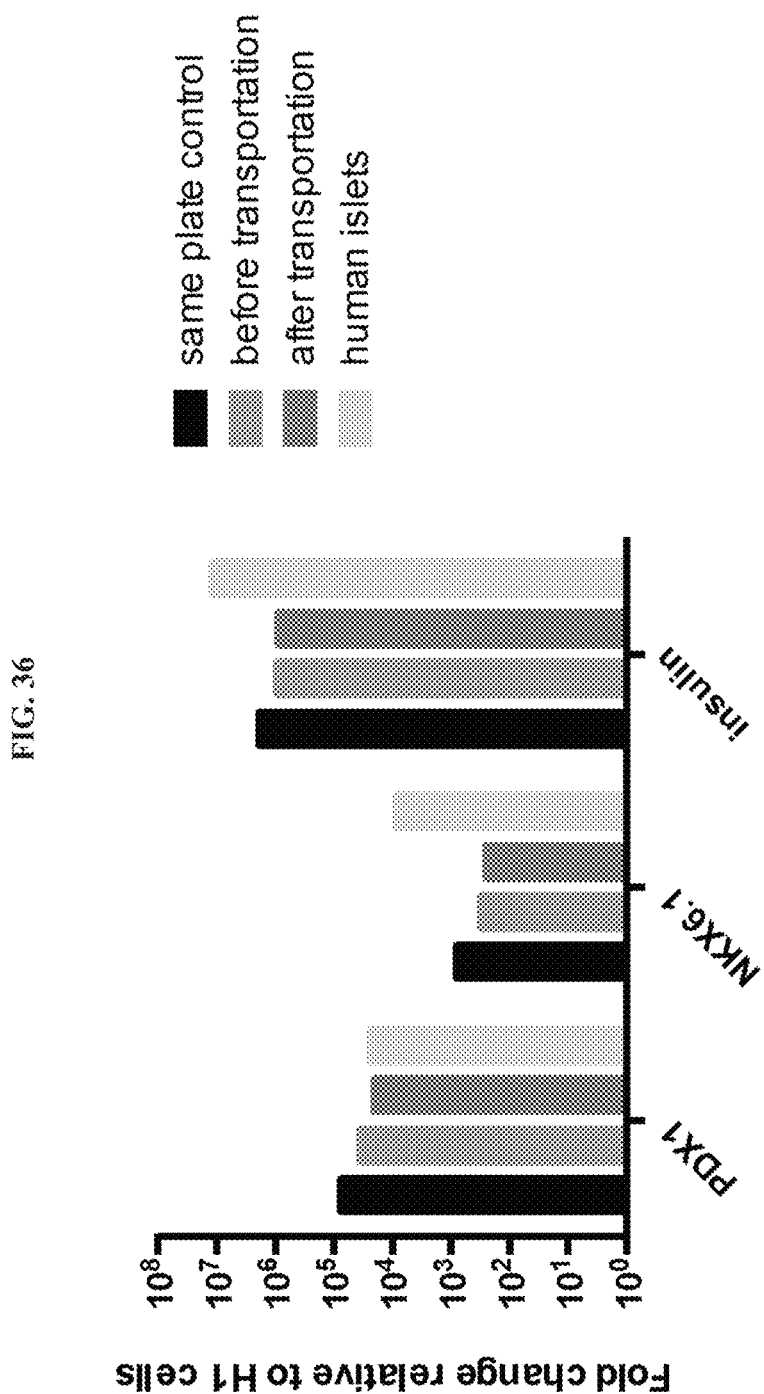
FIG. 36 shows GSIS of cells differentiated using the methods described herein.
Figure 37:
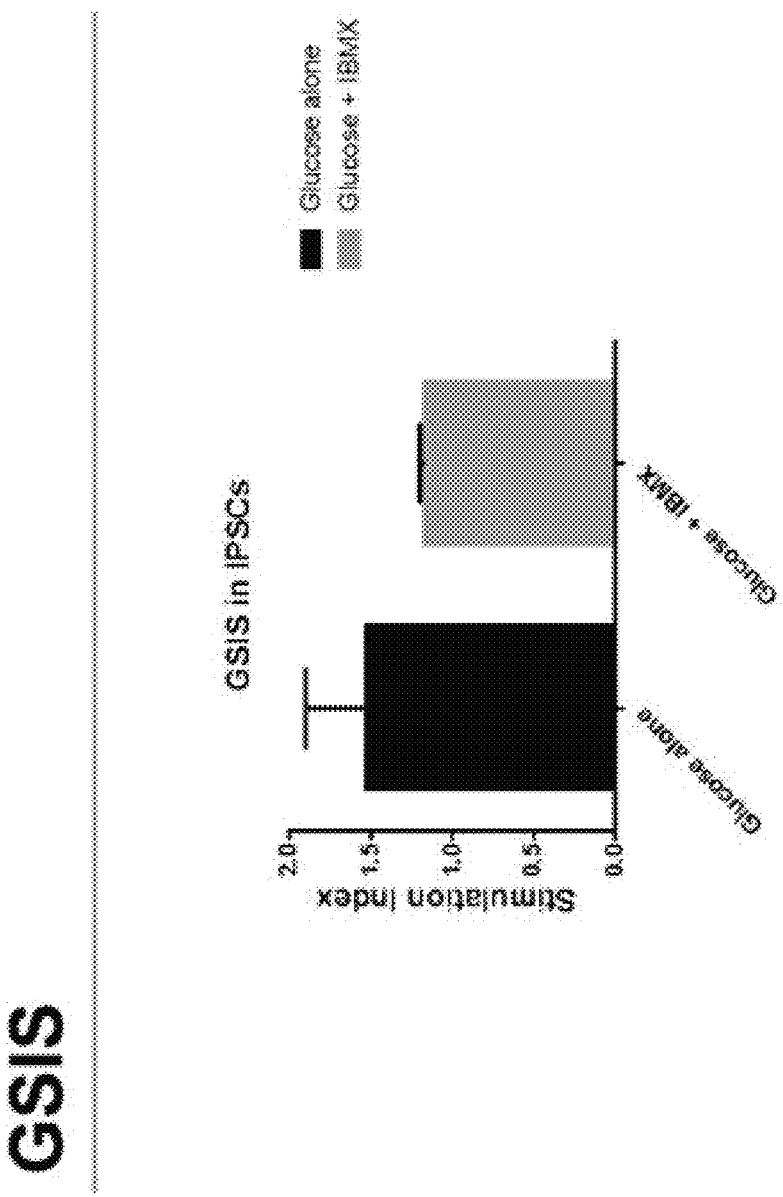
FIG. 37 shows expression of PDX1, NKX6.1, and insulin before and after shipment.
Figure 38:
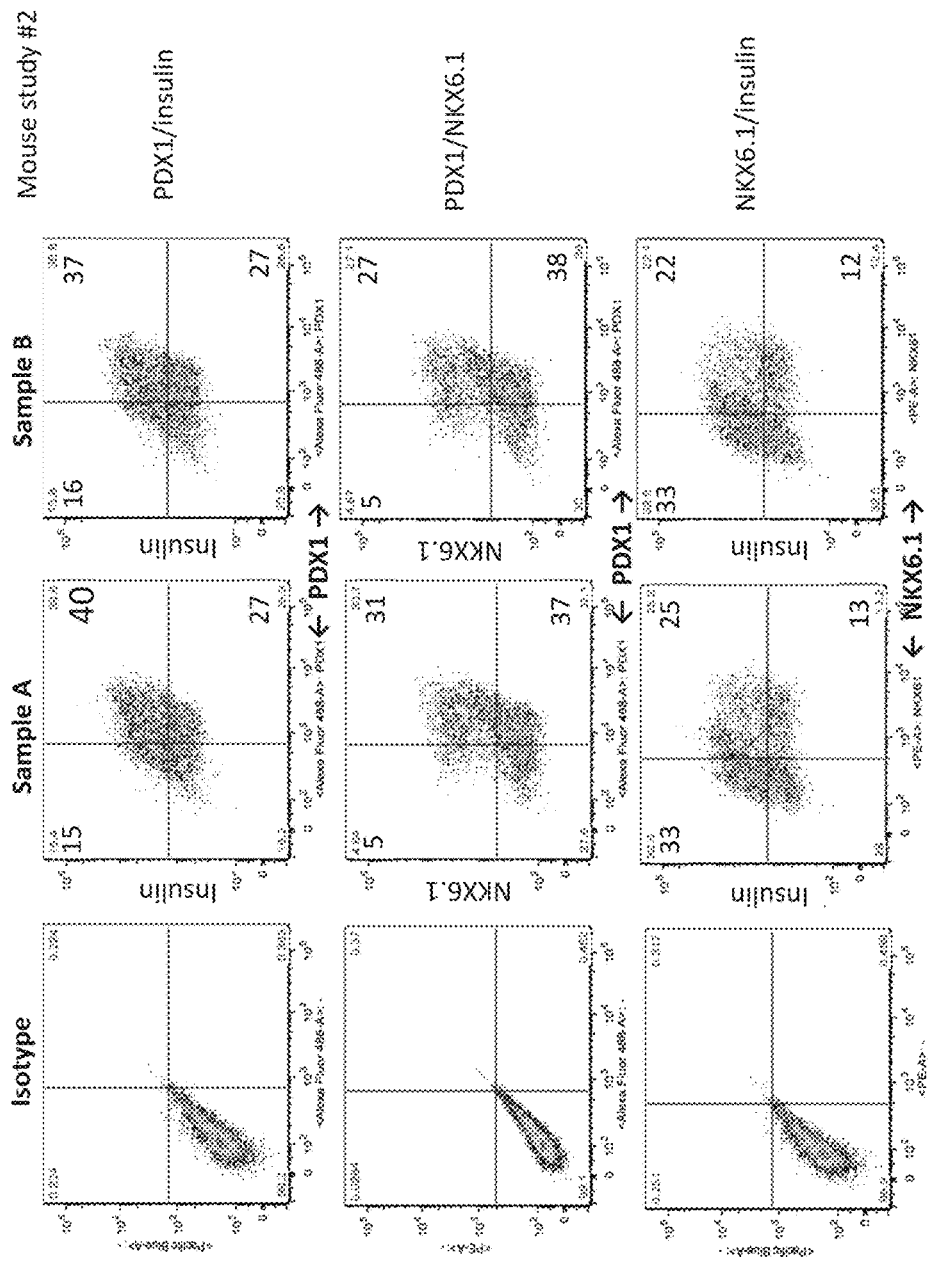
FIG. 38 shows GSIS before and after shipment.
Figure 39:
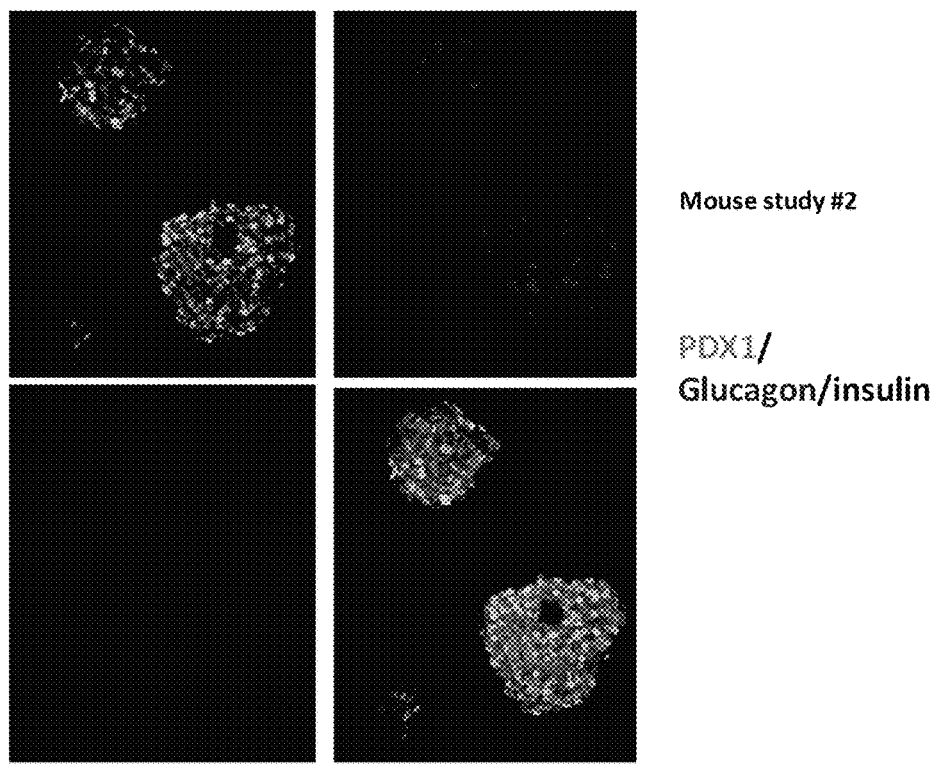
FIG. 39 shows expression of marker genes before and after shipment.
Figure 40:
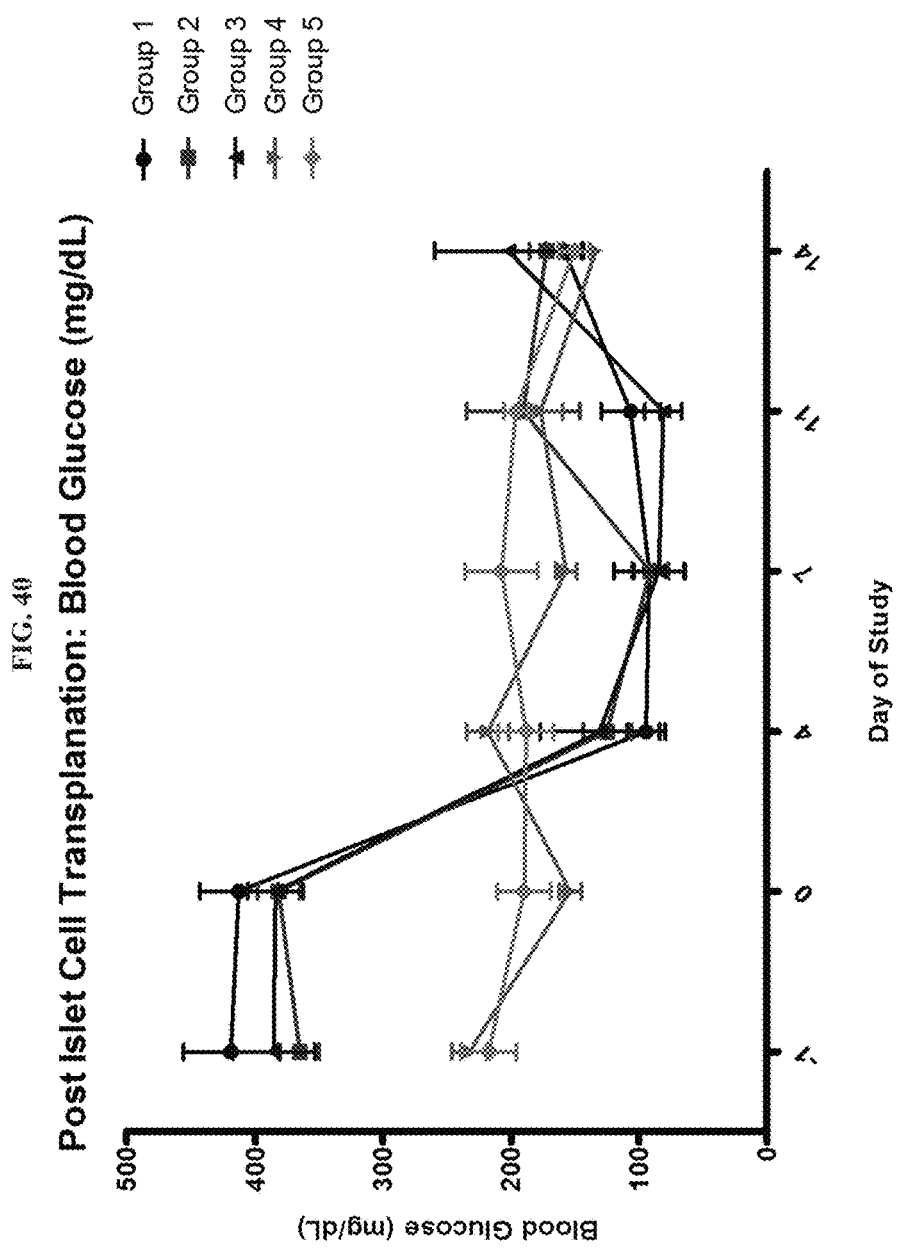
FIG. 40 shows PDX1, insulin and glucagon expression in mouse studies.
Figure 41:
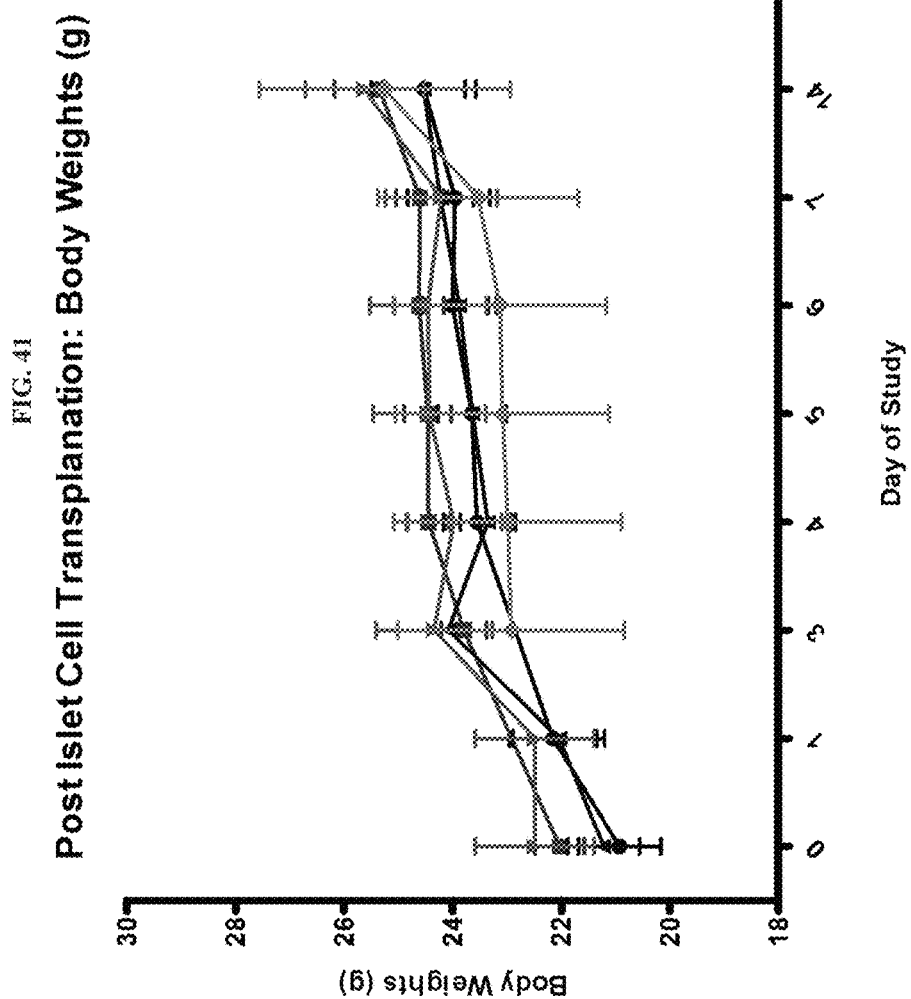
FIG. 41 shows blood glucose in mice administered cells differentiated using the methods described herein
Figure 42:
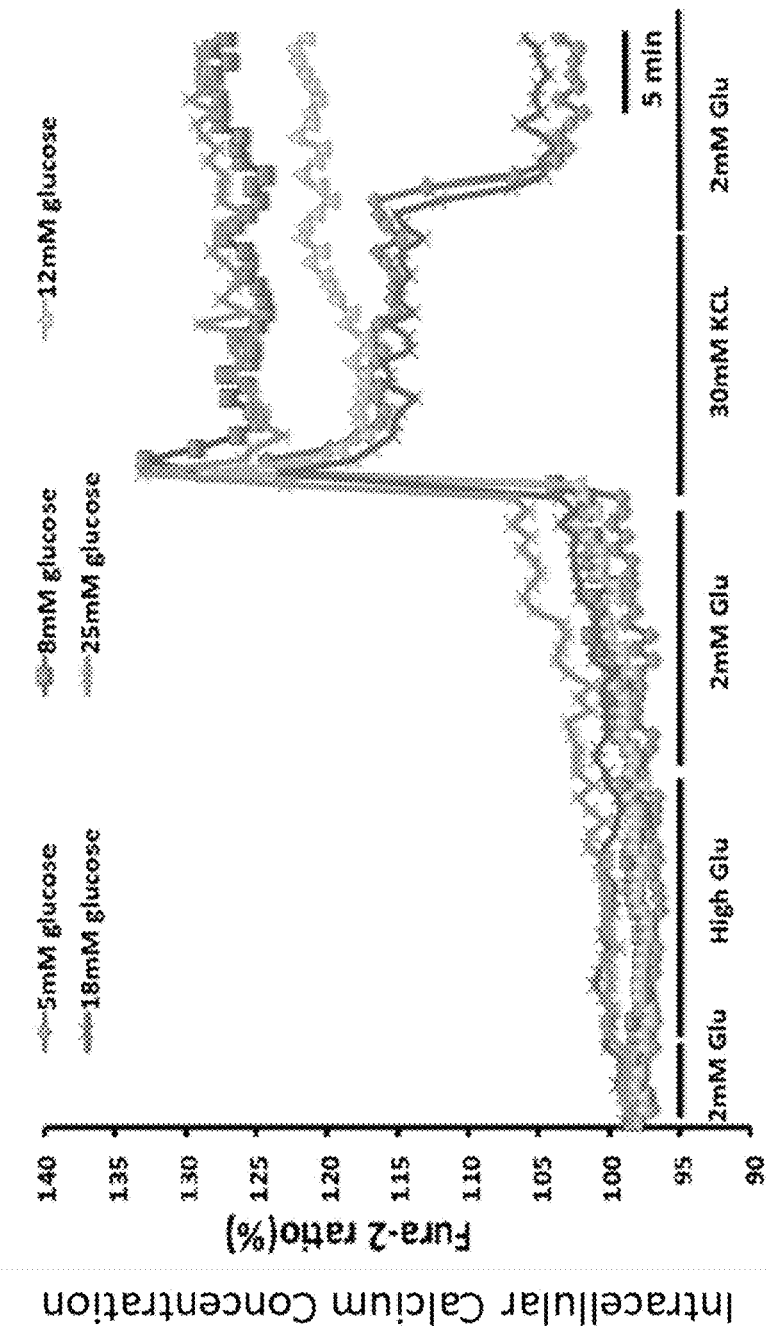
FIG. 42 shows body weight in mice administered cells differentiated using the methods described herein.
Figure 43:
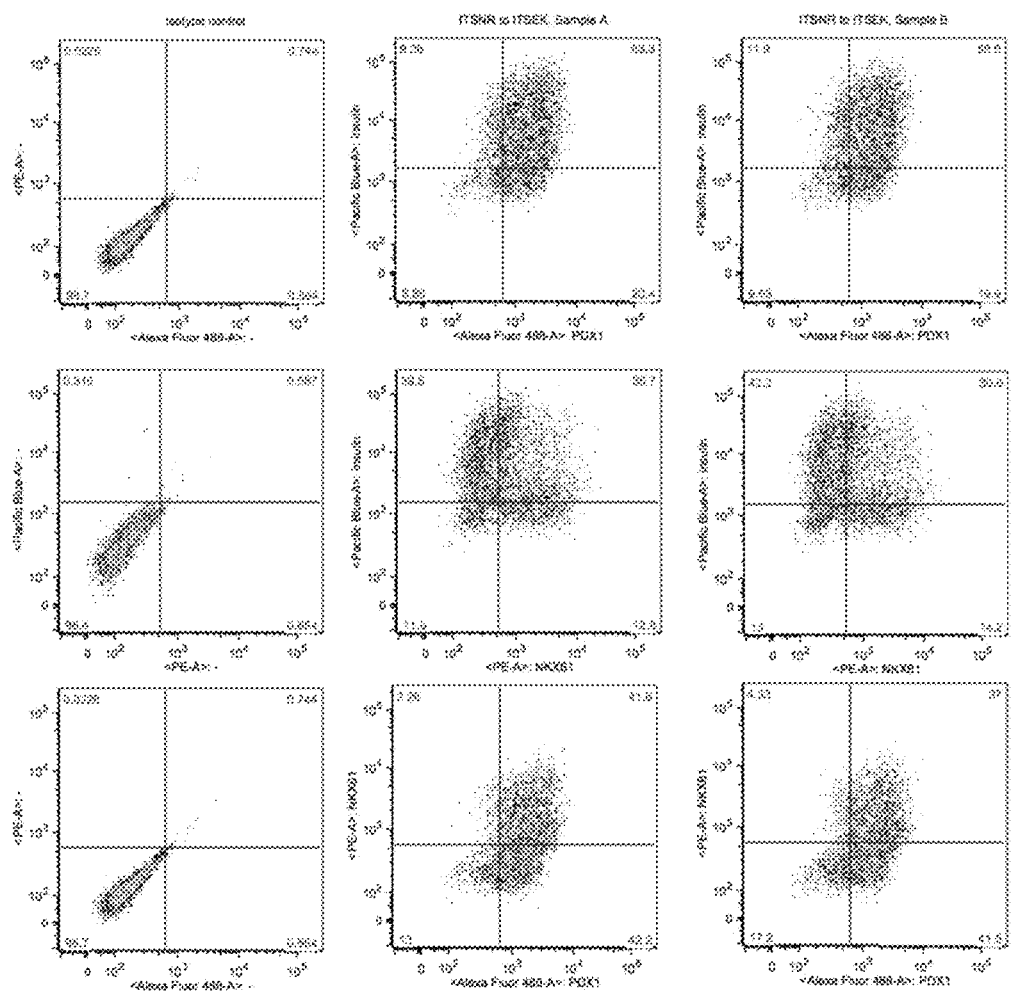
FIG. 43 shows differentiation results using exemplary methods described in Example 18.
Figure 44:
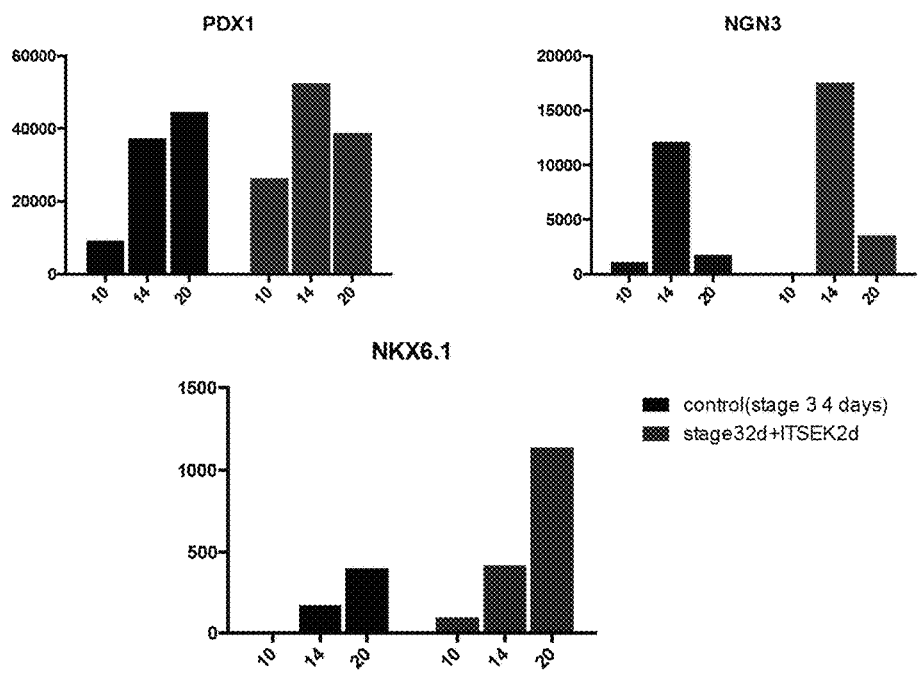
FIG. 44 shows expression of PDX1, NGN3, and NKX6.1 using exemplary differentiation methods described in Example 18.
Figure 45:
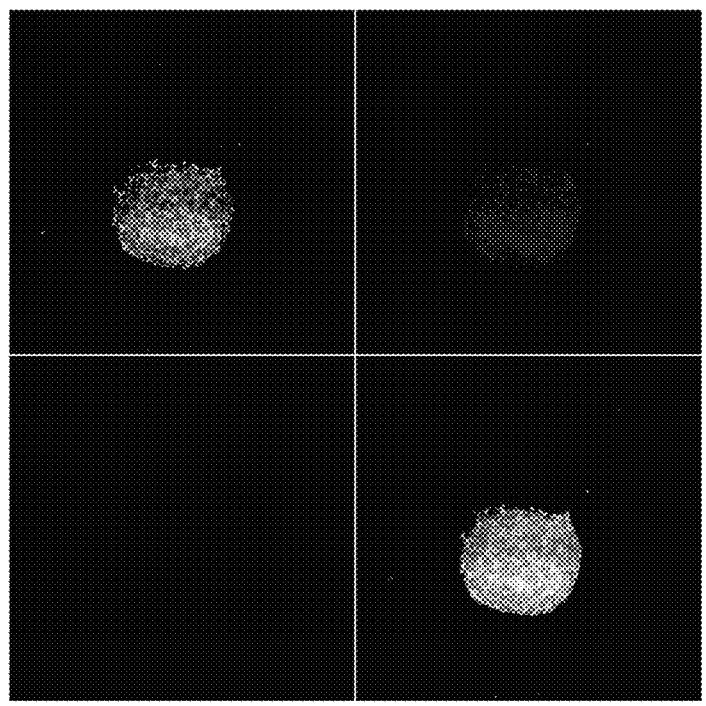
FIG. 45 shows expression of PDX1, insulin, and glucagon using exemplary differentiation methods described in Example 18.
Figure 46:
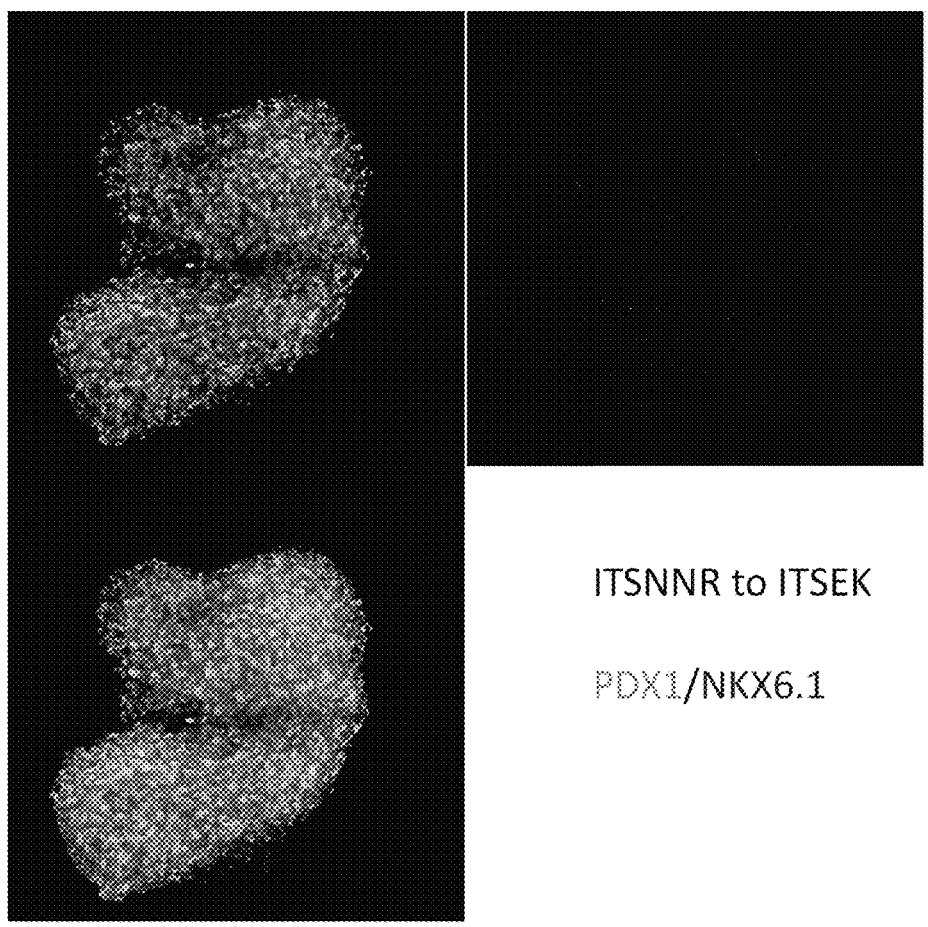
FIG. 46 shows expression of PDX1 and NKX6.1 using exemplary differentiation methods described in Example 18.

Cells were differentiated using the stage 6 protocol described above and in FIG. 27 and analyzed for islet cell markers. FIGS. 28 and 33 show that ILCs generated are similar to human islets and yield a high percentage of insulin+ and Glucagon− cells (FIG. 28). FIGS. 29, 30, and 34 show that the induced islet cells exhibit significant co-expression of insulin, NKKX6.1, and MafA. FIG. 31 shows that cells are somatostatin positive. FIG. 32 shows that cells exhibit increased expression of key genes to levels similar to that of islet cells. FIG. 35 shows that induced islet cells exhibit GSIS similar to human islet cells.

Cells developed using the described method were used in animal studies according to the protocol in the table below. Human C-peptide was detected in serum of treated mice CS10 was used as the freezing media. After the cells were thawed, the cells were moved from two wells (before thaw) into one well (after thaw).

Figure 20:
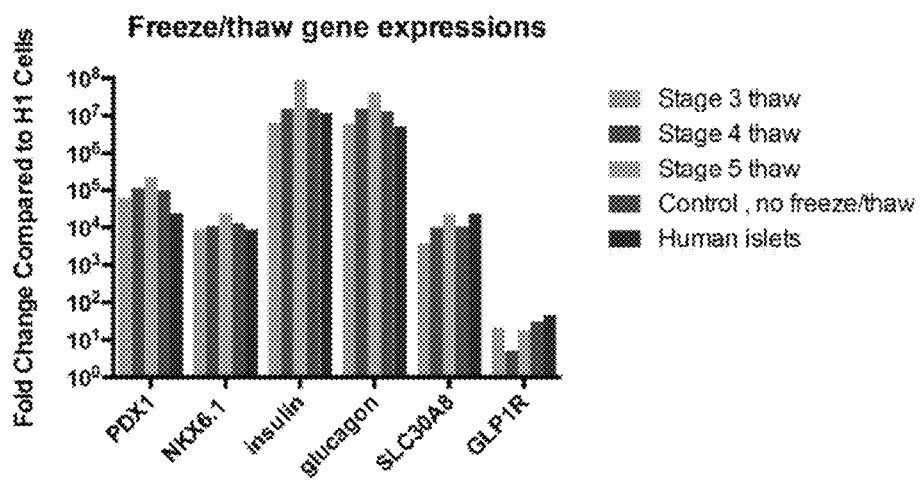
FIG. 20 shows gene expression after freeze-thaw experiments.
Figure 21:
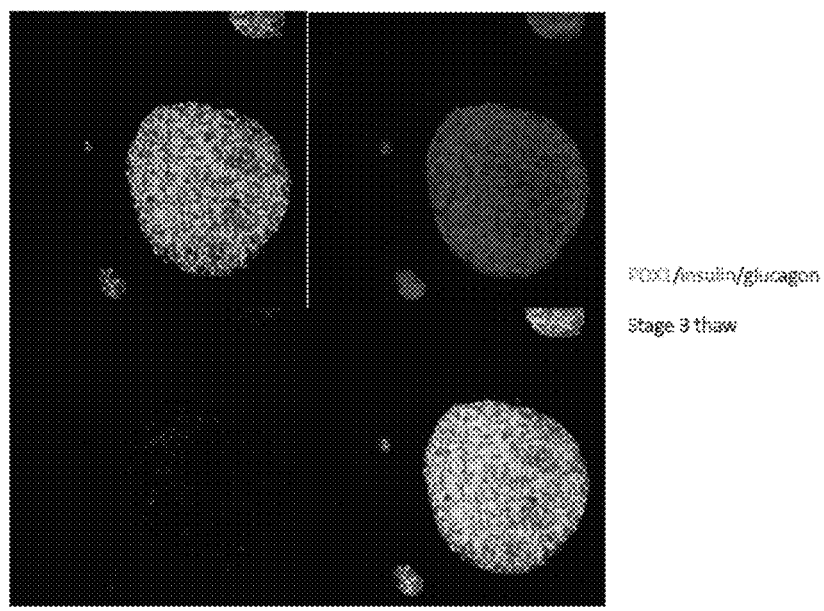
FIG. 21 shows PDX1, insulin and glucagon expression after stage 3 freeze-thaw experiments.
Figure 22:
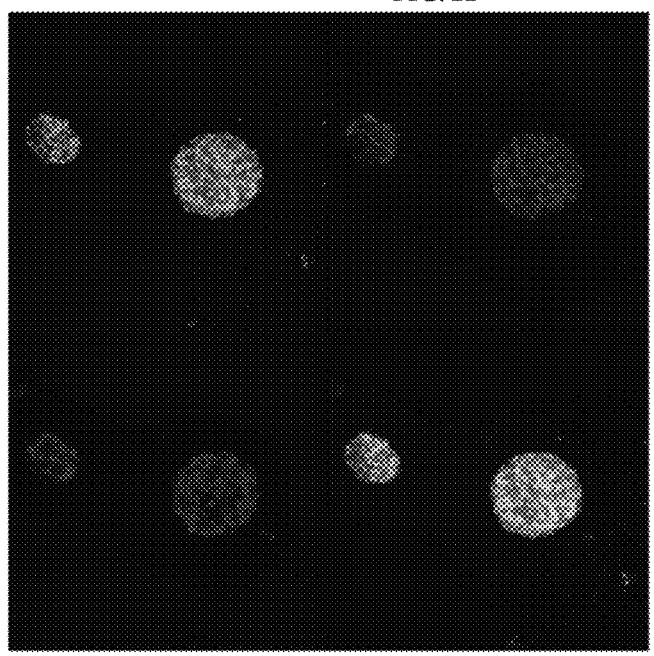
FIG. 22 shows PDX1, NXX6.1, and insulin expression after stage 3 freeze-thaw experiments.
Figure 23:
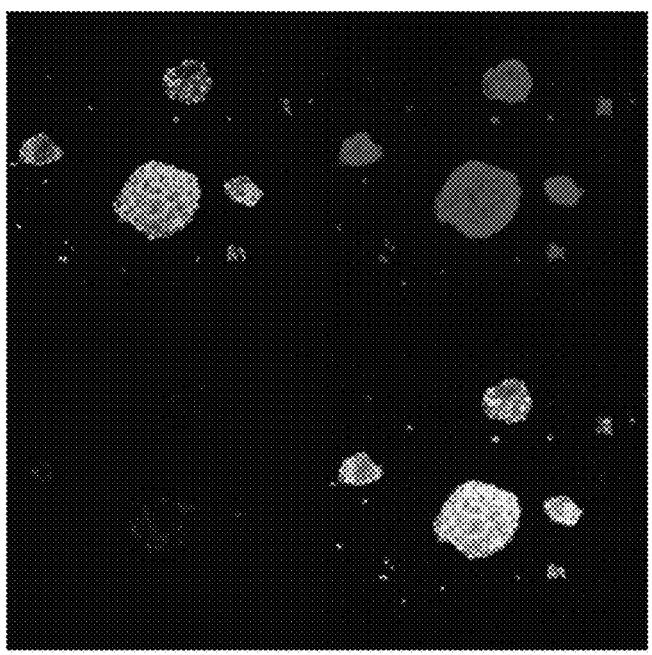
FIG. 23 shows PDX1, insulin and glucagon expression after stage 4 freeze-thaw experiments.
Figure 24:
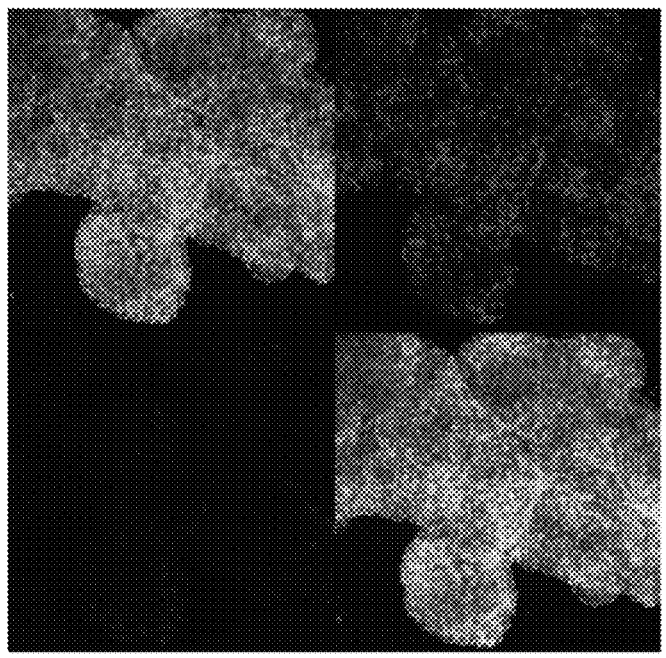
FIG. 24 shows PDX1, NXX6.1, and insulin expression after stage 4 freeze-thaw experiments.
Figure 25:
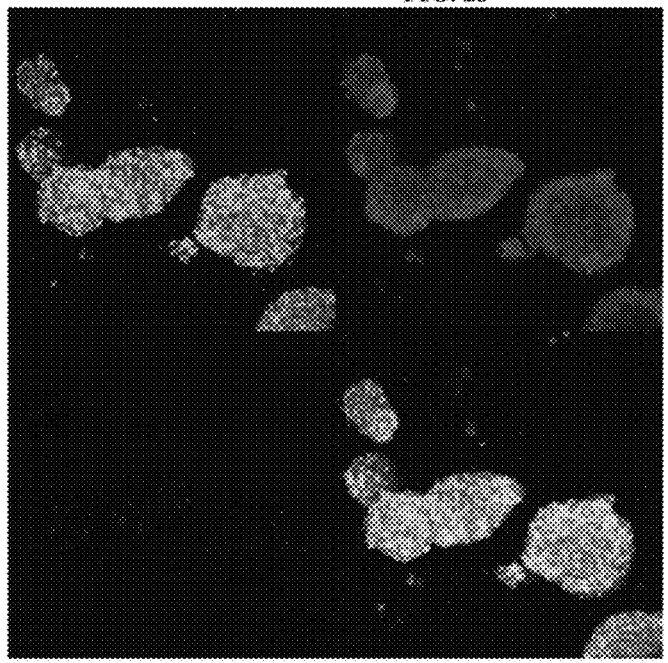
FIG. 25 shows PDX1, insulin and glucagon expression after stage 5 freeze-thaw experiments.
Figure 26:
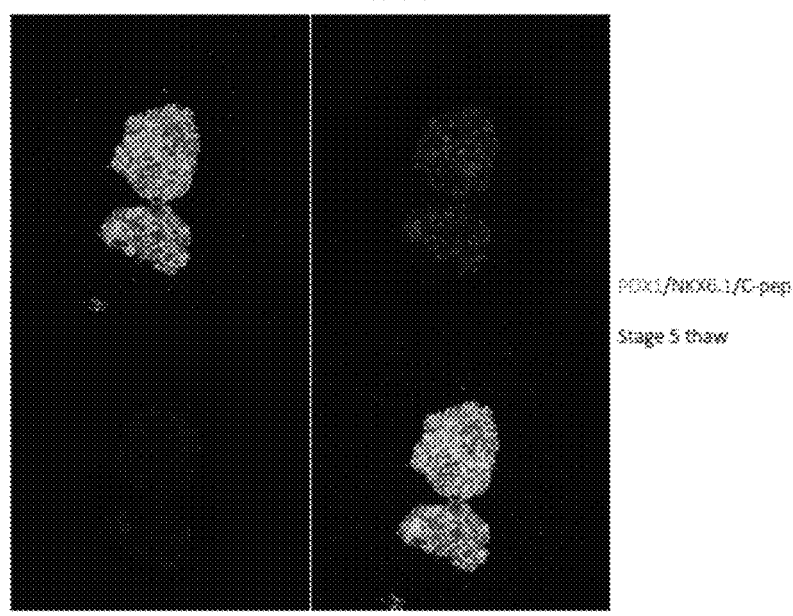
FIG. 26 shows PDX1, NXX6.1, and insulin expression after stage 5 freeze-thaw experiments.

The freeze/thaw experiment was successful. Freeze/thaw gene expression is shown in FIG. 20. Marker expression from stage 3 thaw is shown in FIGS. 21 and 22. Marker expression from stage 4 thaw is shown in FIGS. 23 and 24. Marker expression from stage 5 thaw is shown in FIGS. 25 and 26.

Cells from stage 3 freeze/thaw showed cytoplasmic NKX6.1 staining. Cells from stage 4 and 5 have good PDX1, NKX6.1, insulin and glucagon staining. GLP1R transcript expression was relatively low in stage 4 thawed cells. In some embodiments, the end of stage 5 is chosen as a stage for freeze/thaw.

Example 17

Shipping Experiments

Experiments were conducted to determine the effect of shipping induced islet cells on Transwells. Cells were differentiated according to the protocol described in Example 15. (ProgenMixIII). Total differentiation time was 27 days and the final product was islet-like-clusters (ILCs) in suspension. On the day of shipment, ILCs were counted and divided into individual mouse dosages: one mouse dosage per bottle. Cells were sent by FedEx overnight at 4° C. using cold packs. Leftover ILCs from shipment were used as controls.

Results are shown in FIGS. 36-42. iPS derived beta-cell clusters responded to glucose challenge and tolbutamide, a KATP channel closer. IBCs on Transwells shipped overnight via FedEx at room temperature exhibited gene expression patterns and GSIS similar to pre-shipment IBCs. Islet-Like Clusters (ILCs) shipped via FedEx and transplanted into mice yielded human c-peptide in mouse serum after 2 weeks. In addition, ILCs same-day exhibited intracellular calcium signals that were similar to calcium signals measured in human cadaveric islets.

Example 18

Differentiation Protocol

Experiments were performed to assess the performance of variations of the differentiation protocol described above.

| Groups | Dosage (ILCs) | Cells/Mouse | Streptozotocin (STZ) Treatment | Cell Transplantation | Number of mice (24 total) |
|---|---|---|---|---|---|
| 10K Group | 10K | ~5M | Yes | Yes | 8 mice |
| 6K Group | 6K | ~3M | Yes | Yes | 8 mice |
| 3K Group | 3K | ~1.5M | Yes | Yes | 8 mice |
| Control group | 6k | ~3M | No | Yes | 4 mice |
| Non-diabetic Group | None | 0 | No | No | 2 mice |

Example 16

Freeze Thaw

NCRM-1 cells at the end of stage 3, 4 and 5 were frozen at −80° C. in CS10, thawed the second day and allowed to continue the next stages of differentiation. QPCR and immunostaining were done at end of differentiation.

Stage 3 was split into two stages: The previous stage 3 formula was ITSNNR (ITS+Nicotinamide+Noggin+RA) for 4 days. The new version is ITS(N)NR (with or without nicotinamide) for 2 days, then switch to ITSEK (ITS+50 ng/ml EGF+50 ng/ml KGF(FGF7)) for 2 days. Splitting stage 3 into two separate stages inhibited NGN3 induction at stage 3 and enhanced PDX1 expression at end (see FIGS. 43-46 for results).

300 ng/ml Noggin was added in step 4 and 10 uM ALK5i was added in step 5. In the final step, cells were transferred from transwell to suspension culture (in low attachment wells or flasks). Final step media are: B27(50× dilution), 10 uM ALK5i, 25 uM Forskolin, 10 uM ZnSO4, 1 uM T3, 10 ug/ml heparin, 10 uM LY294002, 10 mM GSH and 5 uM Warfarin.

Figure 47:
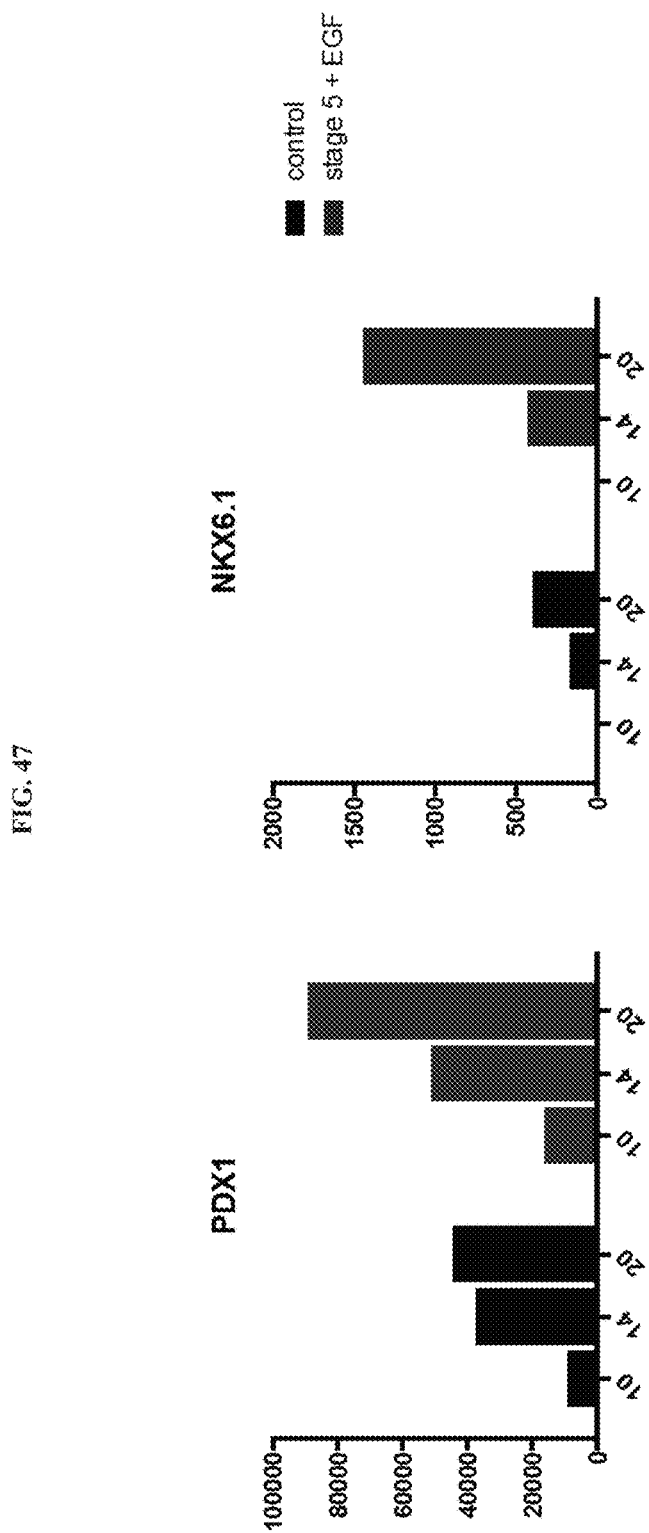
FIG. 47 shows expression of PDX1 and NKX6.1 using exemplary differentiation methods described in Example 18.

EGF was added at stage 5. Ten to fifty ng/ml EGF was added at stage 5 to enhance NKX6.1 expression at end (results are shown in FIG. 47).

Figure 48:
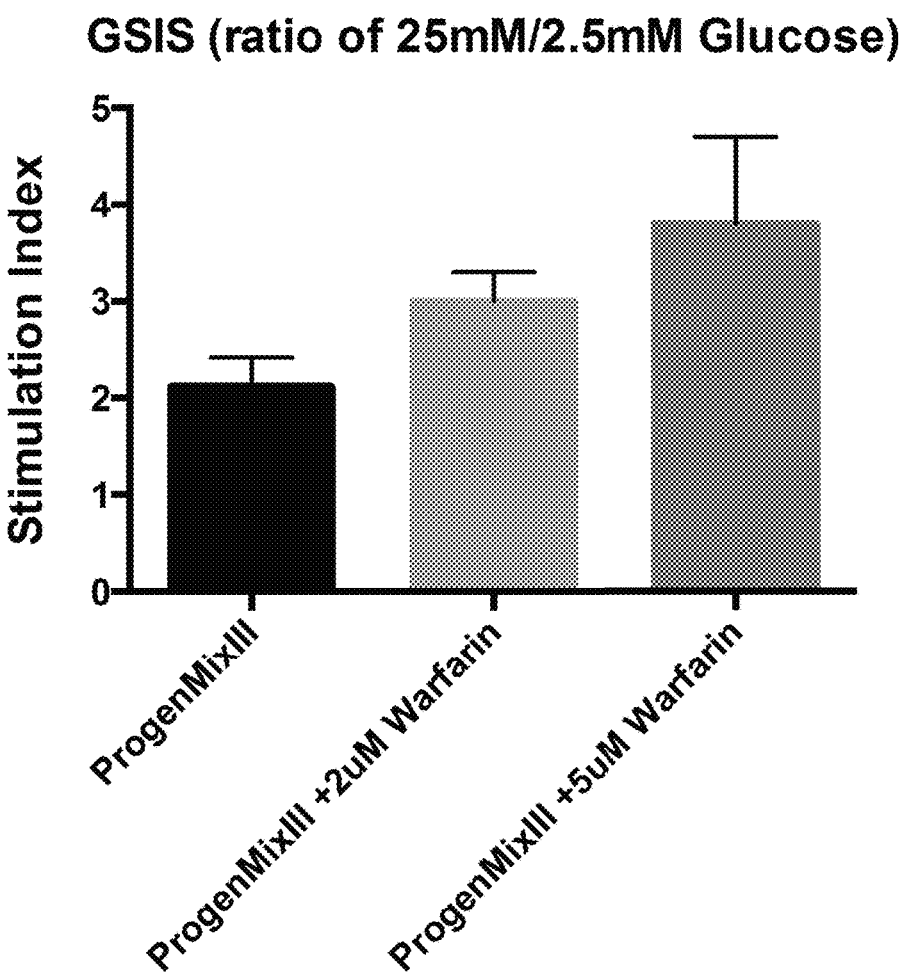
FIG. 48 shows GSIS results of differentiated cells in the presence and absence of Warfarin.

Warfarin was added at stage 6. It has been reported that warfarin inhibits the Axl signaling pathway (*Cancer Res* canres.2887.2014; Haase, T. N. et al. Diabetologia 56, 763-773(2013). Inhibition of this pathway is important in both inhibiting pancreatic cancer progression and promoting pancreatic beta cell maturation. Warfarin was added at 2 uM in stage 6 for 3 days. SI using 2 uM Warfarin in stage 6 was 3.0, SI using 5 uM Warfarin in stage 6 was 3.8, while SI for the control group was 2.1. In some embodiments, 1-10 um warfarin in stage 6 for 6 days is used. Addition of warfarin in the final media significantly increased stimulation index in GSIS test (See FIG. 48 for results).

The complete list of steps is:
(a) culturing the stem cells for 2-4 days in a chemically defined medium, basic fibroblast growth factor, Activin A, BMP4, LY294002, and Matrigel;
(b) culturing the cells from step (a) for 2-4 days in the presence of chemically defined ITS medium, FGF7, nicotinamide, and Matrigel;
(c) culturing the cells from step (b) for 2 days in the presence of a chemically defined ITS medium, retinoic acid, Noggin, nicotinamide, and Matrigel;
(d) culturing the cell of step (c) for 2 days in the presence of chemically defined ITS medium, EGF, and FGF7;
(e) culturing the cells from step (d) for 6-10 days in the presence of a B27 serum-free medium, IGF I, IGF II, FGF7, insulin, Noggin, nicotinamide, exendin-4, ALK5i II, forskolin, and Matrigel; and
(f) maintaining the cells of the pancreatic lineage for 1-50 days by culturing the cells from step (e) in a suspension culture in the presence of a serum-free medium, ALK5, Forskolin, ZnSO4, T3, B27, heparin, and antioxidant, Warfarin, and a P13 kinase inhibitor.

All publications and patents mentioned in the present application and/or listed below are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

The invention claimed is:

1. A method of screening an agent, comprising:
a) contacting a composition comprising cluster aggregates of pancreatic β-like cells, wherein said pancreatic β-like cells are generated by a method comprising:
(i) culturing human pluripotent stem cells on an extracellular matrix for 2-4 days in a chemically defined medium, basic fibroblast growth factor, Activin A, and BMP4;
(ii) culturing the cells on an extracellular matrix from step (a) for 2-4 days in the presence of chemically defined insulin, transferrin and selenium (ITS) medium, FGF7, and nicotinamide;
(iii) culturing the cells on an extracellular matrix from step (b) for 3-5 days in the presence of a chemically defined ITS medium; retinoic acid; Noggin; and nicotinamide; and
(iv) culturing the cells on an extracellular matrix from step (c) for 6-10 days in the presence of a B27 serum-free medium, IGF I, IGF II, FGF7, insulin, nicotinamide, exendin-4, an ALK5i II, and forskolin, thereby producing cluster aggregates of insulin+ glucagon pancreatic β-like cells that exhibit in vitro glucose stimulated insulin secretion with said agent; and
b) assaying the effect of said agent on one or more properties or activities of said cluster aggregates by comparing said effect to the effect in the absence of said agent.

2. The method of claim 1, wherein said composition is in a reaction vessel.

3. The method of claim 2, wherein said reaction vessel is a multiwell plate.

4. The method of claim 1, wherein said agent is a library of compounds.

5. The method of claim 1, wherein said method is high-throughput.

6. The method of claim 5, wherein said method is automated.

7. The method of claim 1, wherein said agent is selected from the group consisting of a small molecule, a peptide, and a polynucleotide.

8. The method of claim 1, wherein said effect or properties are selected from the group consisting of a change in morphology, a marker phenotype, metabolic activity, and cytotoxicity.

9. The method of claim 8, wherein said effect is level of insulin secretion.

10. The method of claim 1, wherein said method further comprises:
(v) maintaining the cells from step (iv) for 1-14 days by culturing the cells in the presence of B27 serum-free medium, IGF I, FGF7, insulin, nicotinamide, exendin-4, and forskolin.

11. The method of claim 10, wherein said step (v) further comprises Warfarin.

12. The method of claim 1, wherein said step (iii) is performed in two steps.

13. The method of claim 12, wherein said first step of step (iii) comprises culturing in the presence of chemically defined ITS medium; retinoic acid; and Noggin for 2 days and then culturing in in the presence of chemically defined ITS medium, EGF, and FGF7 for two days.

14. The method of claim 1, wherein said step (iv) further comprises EGF.

15. The method of claim 1, wherein said cluster aggregates comprise 500-1000 cells.

16. The method of claim 1, wherein said cluster aggregates are 200 µM in diameter.

17. A method of screening an agent, comprising:
a) contacting a composition comprising cluster aggregates of pancreatic β-like cells, wherein said pancreatic β-like cells are generated by a method comprising:
  (i) culturing human pluripotent stem cells on an extracellular matrix for 2-4 days in a chemically defined medium, basic fibroblast growth factor, Activin A, BMP4, LY294002;
  (ii) culturing the cells from step (i) on an extracellular matrix for 2-4 days in the presence of chemically defined insulin, transferrin and selenium (ITS) medium, FGF7, nicotinamide;
  (iii) culturing the cells from step (ii) on an extracellular matrix for 2 days in the presence of a chemically defined ITS medium, retinoic acid, Noggin, nicotinamide;
  (iv) culturing the cell of step (iii) for 2 days in the presence of chemically defined ITS medium, EGF, and FGF7;
  (v) culturing the cells from step (iv) on an extracellular matrix for 6-10 days in the presence of a B27 serum-free medium, IGF I, IGF II, FGF7, insulin, Noggin, nicotinamide, exendin-4, ALK5i II, forskolin, thereby producing cluster aggregates of insulin+glucagon-pancreatic β-like cells that exhibit in vitro glucose stimulated insulin secretion; and
  (vi) maintaining the cells of step (v) for 1-50 days by culturing the cells in a suspension culture in the presence of a serum-free medium, ALK5, Forskolin, ZnSO4, T3, B27, heparin, and antioxidant, Warfarin, and a P13 kinase inhibitor
with said agent; and
b) assaying the effect of said agent on one or more properties or activities of said cluster aggregates by comparing said effect to the effect in the absence of said agent.

18. The method of claim 17, wherein said agent is selected from the group consisting of a small molecule, a peptide, and a polynucleotide.

19. The method of claim 17, wherein said effect or properties are selected from the group consisting of a change in morphology, a marker phenotype, metabolic activity, and cytotoxicity.

20. The method of claim 17, wherein said effect is level of insulin secretion.

* * * * *